US010206738B2

(12) United States Patent
Parihar et al.

(10) Patent No.: US 10,206,738 B2
(45) Date of Patent: Feb. 19, 2019

(54) ROBOTIC ELECTROSURGICAL DEVICE WITH DISPOSABLE SHAFT

(71) Applicant: Ethicon Endo-Surgery, LLC, Guaynabo, PR (US)

(72) Inventors: Shailendra K. Parihar, Mason, OH (US); Barry C. Worrell, Centerville, OH (US)

(73) Assignee: Ethicon LLC, Guaynabo, PR (US)

( * ) Notice: Subject to any disclaimer, the term of this patent is extended or adjusted under 35 U.S.C. 154(b) by 34 days.

(21) Appl. No.: 15/204,101

(22) Filed: Jul. 7, 2016

(65) Prior Publication Data
US 2016/0310209 A1 Oct. 27, 2016

Related U.S. Application Data

(63) Continuation of application No. 13/798,634, filed on Mar. 13, 2013, now Pat. No. 9,402,687.

(51) Int. Cl.
*A61B 17/00* (2006.01)
*A61B 18/14* (2006.01)
(Continued)

(52) U.S. Cl.
CPC .... *A61B 18/1447* (2013.01); *A61B 17/07207* (2013.01); *A61B 18/1445* (2013.01); *A61B 34/30* (2016.02); *A61B 34/37* (2016.02); *A61B 17/320092* (2013.01); *A61B 2017/0023* (2013.01); *A61B 2017/00398* (2013.01); *A61B 2017/00473* (2013.01); *A61B 2017/00477* (2013.01); *A61B 2017/2903* (2013.01); *A61B 2017/2905* (2013.01);
(Continued)

(58) Field of Classification Search
CPC ............ A61B 18/1442; A61B 18/1447; A61B 2018/00053; A61B 2018/1442; A61B 34/30; A61B 17/00
See application file for complete search history.

(56) References Cited

U.S. PATENT DOCUMENTS 5,792,135 A 8/1998 Madhani et al.
5,810,880 A 9/1998 Jensen et al.
(Continued)

FOREIGN PATENT DOCUMENTS

WO WO 2004/016196 2/2004

OTHER PUBLICATIONS

International Search Report and Written Opinion dated Jun. 2, 2014 for Application No. PCT/US2014/016403, 12 pgs.
(Continued)

*Primary Examiner* — Allen Porter, Jr.
(74) *Attorney, Agent, or Firm* — Frost Brown Todd LLC

(57) ABSTRACT

An apparatus includes an interface assembly and a shaft assembly. The interface assembly is for use with a robotic system and includes a first drive assembly. The first drive assembly includes a first slot having a distal recess and a transverse recess. The shaft assembly is removably couplable with the interface assembly and includes an end effector and a first coupling feature. The first drive assembly of the interface assembly actuates the end effector of the shaft assembly. The first coupling feature is couplable with the first slot of the first drive assembly to longitudinally fix the shaft assembly relative to the interface assembly.

19 Claims, 46 Drawing Sheets

(51) Int. Cl.
- *A61B 17/072* (2006.01)
- *A61B 34/30* (2016.01)
- *A61B 34/37* (2016.01)
- *A61B 17/29* (2006.01)
- *A61B 17/32* (2006.01)
- *A61B 90/00* (2016.01)
- *A61B 18/00* (2006.01)
- *A61B 18/12* (2006.01)

(52) U.S. Cl.
CPC ........... *A61B 2017/2923* (2013.01); *A61B 2017/2927* (2013.01); *A61B 2018/0063* (2013.01); *A61B 2018/126* (2013.01); *A61B 2018/1455* (2013.01); *A61B 2034/305* (2016.02); *A61B 2090/035* (2016.02); *Y10T 29/49002* (2015.01)

(56) References Cited

U.S. PATENT DOCUMENTS

| | | | |
|---|---|---|---|
| 5,817,084 A | 10/1998 | Jensen | |
| 5,878,193 A | 3/1999 | Wang et al. | |
| 6,231,565 B1 | 5/2001 | Tovey et al. | |
| 6,364,888 B1 | 4/2002 | Niemeyer et al. | |
| 6,500,176 B1 | 12/2002 | Truckai et al. | |
| 6,783,524 B2 | 8/2004 | Anderson et al. | |
| 7,112,201 B2 | 9/2006 | Truckai et al. | |
| 7,125,409 B2 | 10/2006 | Truckai et al. | |
| 7,169,146 B2 | 1/2007 | Truckai et al. | |
| 7,186,253 B2 | 3/2007 | Truckai et al. | |
| 7,189,233 B2 | 3/2007 | Truckai et al. | |
| 7,220,951 B2 | 5/2007 | Truckai et al. | |
| 7,306,597 B2 | 12/2007 | Manzo | |
| 7,309,849 B2 | 12/2007 | Truckai et al. | |
| 7,311,709 B2 | 12/2007 | Truckai et al. | |
| 7,354,440 B2 | 4/2008 | Truckai et al. | |
| 7,380,696 B2 | 6/2008 | Shelton, IV et al. | |
| 7,381,209 B2 | 6/2008 | Truckai et al. | |
| 7,404,508 B2 | 7/2008 | Smith et al. | |
| 7,455,208 B2 | 11/2008 | Wales et al. | |
| 7,506,790 B2 | 3/2009 | Shelton, IV et al. | |
| 7,524,320 B2 | 4/2009 | Tierney et al. | |
| 7,549,564 B2 | 6/2009 | Boudreaux | |
| 7,559,450 B2 | 7/2009 | Wales et al. | |
| 7,654,431 B2 | 2/2010 | Hueil et al. | |
| 7,691,098 B2 | 4/2010 | Wallace et al. | |
| 7,780,054 B2 | 8/2010 | Wales | |
| 7,784,662 B2 | 8/2010 | Wales et al. | |
| 7,798,386 B2 | 9/2010 | Schall et al. | |
| 7,806,891 B2 | 10/2010 | Nowlin et al. | |
| 7,824,401 B2 | 11/2010 | Manzo et al. | |
| 8,461,744 B2 | 6/2013 | Wiener et al. | |
| 8,475,482 B2 | 7/2013 | Palmer et al. | |
| 8,479,969 B2 | 7/2013 | Shelton, IV et al. | |
| 8,573,461 B2 | 11/2013 | Shelton, IV et al. | |
| 8,573,465 B2 | 11/2013 | Shelton, IV | |
| 8,602,288 B2 | 12/2013 | Shelton, IV et al. | |
| 8,616,431 B2 | 12/2013 | Timm et al. | |
| 8,783,541 B2 | 7/2014 | Shelton, IV et al. | |
| 8,800,838 B2 | 8/2014 | Shelton, IV et al. | |
| 8,820,605 B2 | 9/2014 | Shelton, IV et al. | |
| 8,844,789 B2 | 9/2014 | Shelton, IV et al. | |
| 8,939,974 B2 | 1/2015 | Boudreaux et al. | |
| 8,951,248 B2 | 2/2015 | Messerly et al. | |
| 8,956,349 B2 | 2/2015 | Aldridge et al. | |
| 8,986,302 B2 | 3/2015 | Aldridge et al. | |
| 9,023,071 B2 | 5/2015 | Miller et al. | |
| 9,039,695 B2 | 5/2015 | Giordano et al. | |
| 9,050,093 B2 | 6/2015 | Aldridge et al. | |
| 9,060,776 B2 | 6/2015 | Yates et al. | |
| 9,089,327 B2 | 7/2015 | Worrell et al. | |
| 9,089,360 B2 | 7/2015 | Messerly et al. | |
| 9,161,803 B2 | 10/2015 | Yates et al. | |
| 9,220,559 B2 | 12/2015 | Worrell et al. | |
| 9,301,759 B2 | 4/2016 | Spivey et al. | |
| 9,386,983 B2 | 7/2016 | Swensgard et al. | |
| 9,402,682 B2 | 8/2016 | Worrell et al. | |
| 9,402,687 B2 | 8/2016 | Parihar et al. | |
| 2004/0049205 A1* | 3/2004 | Lee | A61B 34/71 606/130 |
| 2006/0079874 A1 | 4/2006 | Faller et al. | |
| 2007/0191713 A1 | 8/2007 | Eichmann et al. | |
| 2007/0282333 A1 | 12/2007 | Fortson et al. | |
| 2008/0200940 A1 | 8/2008 | Eichmann et al. | |
| 2011/0118754 A1* | 5/2011 | Dachs, II | A61B 19/2203 606/130 |
| 2011/0295295 A1 | 12/2011 | Shelton, IV et al. | |
| 2012/0078243 A1 | 3/2012 | Worrell et al. | |
| 2013/0023868 A1 | 1/2013 | Worrell et al. | |
| 2013/0267969 A1 | 10/2013 | Martin et al. | |

OTHER PUBLICATIONS

U.S. Appl. No. 61/550,768, filed Oct. 24, 2011.
U.S. Appl. No. 61/597,603, filed Feb. 10, 2012.

* cited by examiner

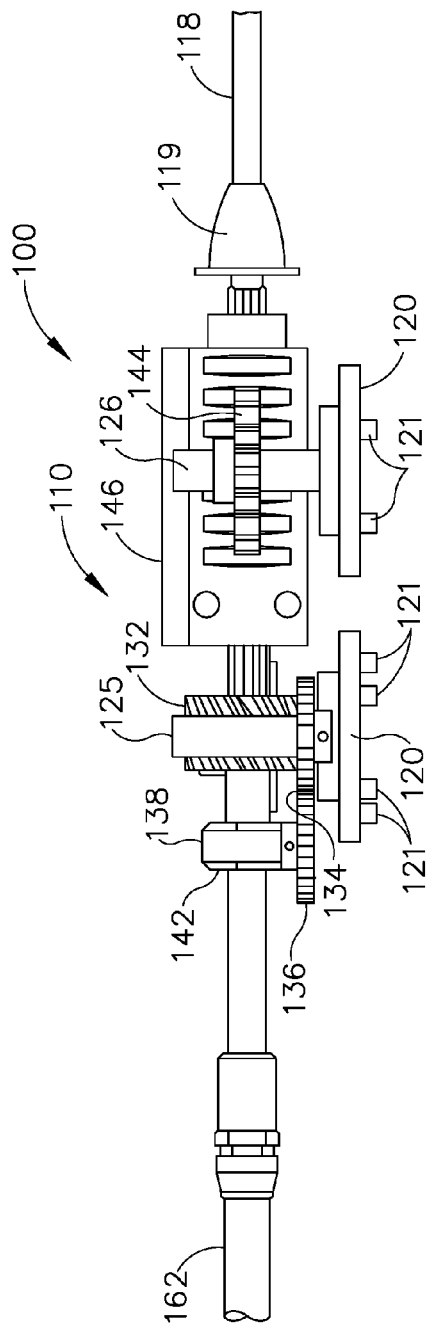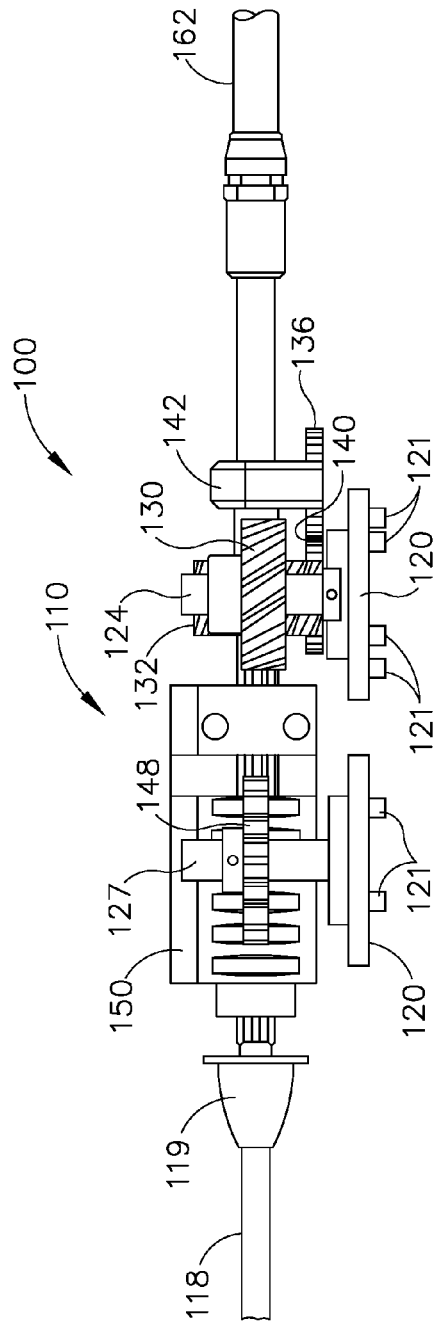
Fig. 12
Fig. 13

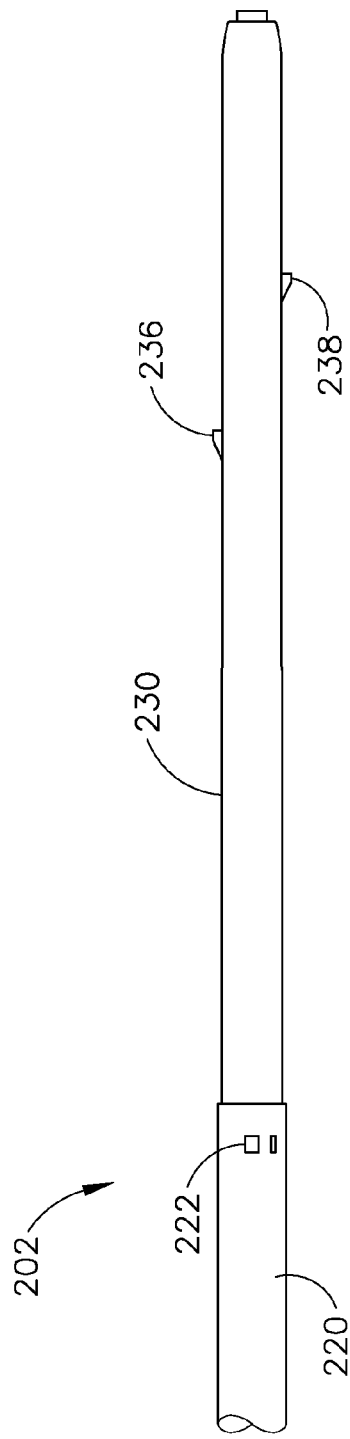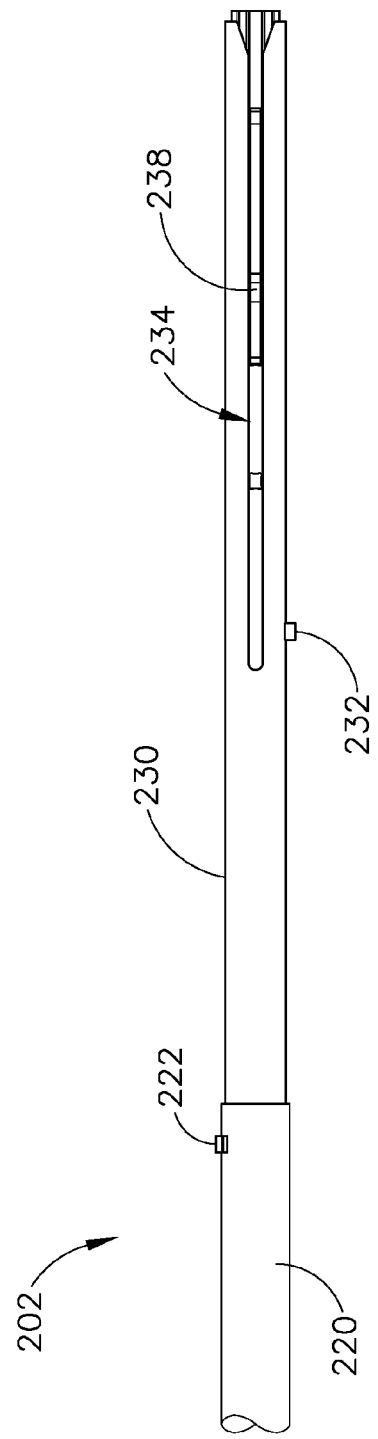
Fig. 16
Fig. 17

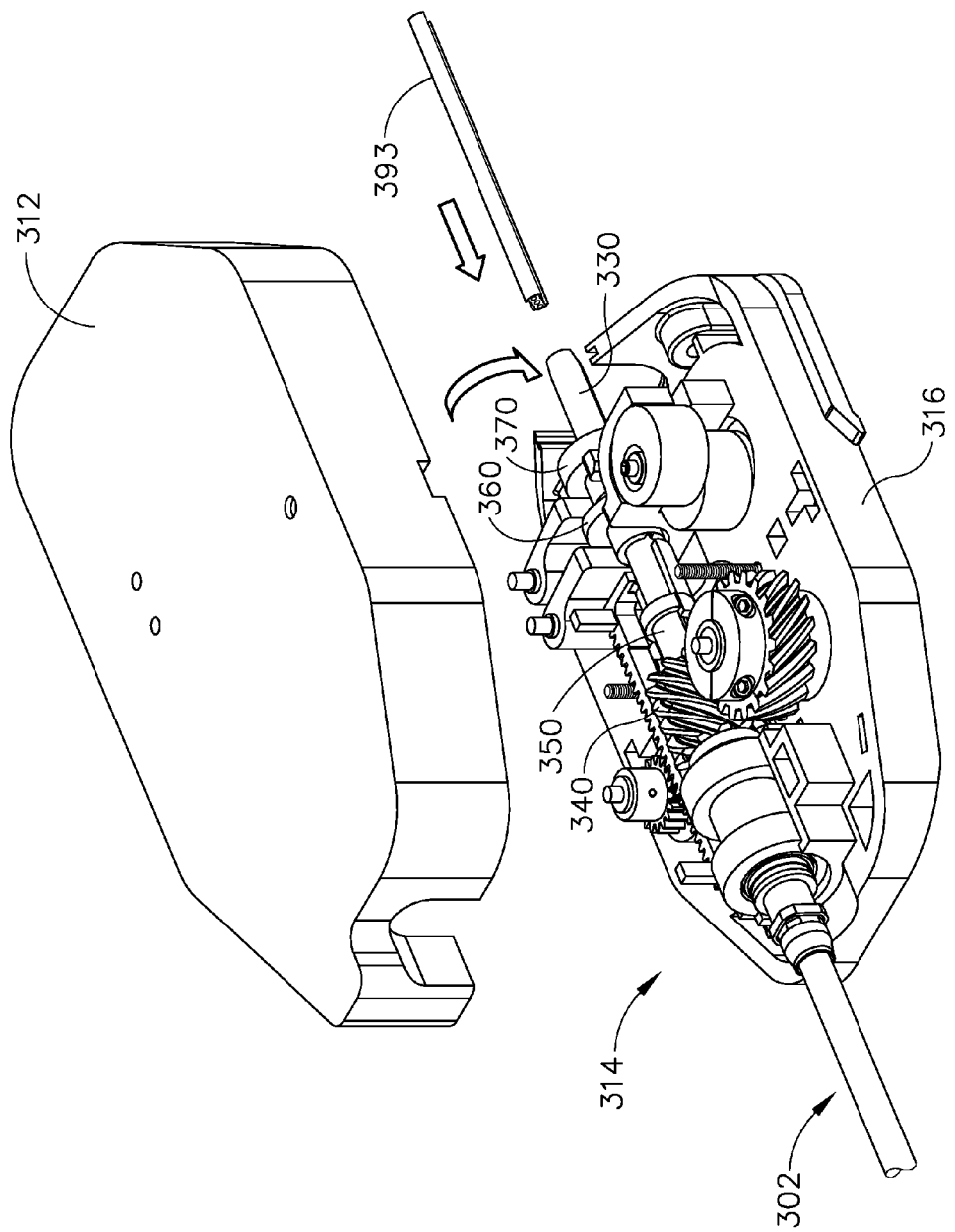

ROBOTIC ELECTROSURGICAL DEVICE WITH DISPOSABLE SHAFT

This application is a continuation application of U.S. Non-provisional application Ser. No. 13/798,634, filed Mar. 13, 2013, entitled "Robotic Electrosurgical Device with Disposable Shaft," issued as U.S. Pat. No. 9,402,687 on Aug. 2, 2016.

BACKGROUND

A variety of surgical instruments include a tissue cutting element and one or more elements that transmit radio frequency (RF) energy to tissue (e.g., to coagulate or seal the tissue). An example of an RF electrosurgical instrument is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical cutting instruments and related concepts are disclosed in U.S. Pub. No. 2011/0087218, entitled "Surgical Instrument Comprising First and Second Drive Systems Actuatable by a Common Trigger Mechanism," published Apr. 14, 2011, issued as U.S. Pat. No. 8,939,974 on Jan. 27, 2015, the disclosure of which is incorporated by reference herein; U.S. Pub. No. 2012/0116379, entitled "Motor Driven Electrosurgical Device with Mechanical and Electrical Feedback," published May 10, 2012, now U.S. Pat. No. 9,161,803, issued Oct. 20, 2015, the disclosure of which is incorporated by reference herein; U.S. Pub. No. 2012/0078243, issued as U.S. Pat. No. 9,877,720 on Jan. 30, 2018, entitled "Control Features for Articulating Surgical Device," published Mar. 29, 2012, the disclosure of which is incorporated by reference herein; U.S. Pub. No. 2012/0078247, issued as U.S. Pat. No. 9,402,682 on Aug. 2, 2016, entitled "Articulation Joint Features for Articulating Surgical Device," published Mar. 29, 2012, the disclosure of which is incorporated by reference herein; U.S. Pub. No. 2013/0030428, entitled "Surgical Instrument with Multi-Phase Trigger Bias," published Jan. 31, 2013, now U.S. Pat. No. 9,089,327, issued Jul. 28, 2015, the disclosure of which is incorporated by reference herein; and U.S. Pub. No. 2013/0023868, issued as U.S. Pat. No. 9,545,253 on Jan. 17, 2017, entitled "Surgical Instrument with Contained Dual Helix Actuator Assembly," published Jan. 31, 2013, the disclosure of which is incorporated by reference herein.

In addition, a variety of surgical instruments include a shaft having an articulation section, providing enhanced positioning capabilities for an end effector that is located distal to the articulation section of the shaft. Examples of such devices include various models of the ENDOPATH® endocutters by Ethicon Endo-Surgery, Inc., of Cincinnati, Ohio. Further examples of such devices and related concepts are disclosed in U.S. Pat. No. 7,380,696, entitled "Articulating Surgical Stapling Instrument Incorporating a Two-Piece E-Beam Firing Mechanism," issued Jun. 3, 2008, the disclosure of which is incorporated by reference herein; U.S. Pat. No. 7,404,508, entitled "Surgical Stapling and Cutting Device," issued Jul. 29, 2008, the disclosure of which is incorporated by reference herein; U.S. Pat. No. 7,455,208, entitled "Surgical Instrument with Articulating Shaft with Rigid Firing Bar Supports," issued Nov. 25, 2008, the disclosure of which is incorporated by reference herein; U.S. Pat. No. 7,506,790, entitled "Surgical Instrument Incorporating an Electrically Actuated Articulation Mechanism," issued Mar. 24, 2009, the disclosure of which is incorporated by reference herein; U.S. Pat. No. 7,549,564, entitled "Surgical Stapling Instrument with an Articulating End Effector," issued Jun. 23, 2009, the disclosure of which is incorporated by reference herein; U.S. Pat. No. 7,559,450, entitled "Surgical Instrument Incorporating a Fluid Transfer Controlled Articulation Mechanism," issued Jul. 14, 2009, the disclosure of which is incorporated by reference herein; U.S. Pat. No. 7,654,431, entitled "Surgical Instrument with Guided Laterally Moving Articulation Member," issued Feb. 2, 2010, the disclosure of which is incorporated by reference herein; U.S. Pat. No. 7,780,054, entitled "Surgical Instrument with Laterally Moved Shaft Actuator Coupled to Pivoting Articulation Joint," issued Aug. 24, 2010, the disclosure of which is incorporated by reference herein; U.S. Pat. No. 7,784,662, entitled "Surgical Instrument with Articulating Shaft with Single Pivot Closure and Double Pivot Frame Ground," issued Aug. 31, 2010, the disclosure of which is incorporated by reference herein; and U.S. Pat. No. 7,798,386, entitled "Surgical Instrument Articulation Joint Cover," issued Sep. 21, 2010, the disclosure of which is incorporated by reference herein.

Some surgical systems provide robotic control of a surgical instrument. With minimally invasive robotic surgery, surgical operations may be performed through a small incision in the patient's body. A robotic surgical system may be used with various types of surgical instruments, including but not limited to surgical staplers, ultrasonic instruments, electrosurgical instruments, and/or various other kinds of instruments, as will be described in greater detail below. An example of a robotic surgical system is the DAVINCI™ system by Intuitive Surgical, Inc., of Sunnyvale, Calif. By way of further example, one or more aspects of robotic surgical systems are disclosed in the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; and U.S. Pat. No. 7,824,401, entitled "Surgical Tool With Writed Monopolar Electrosurgical End Effectors," issued Nov. 2, 2010, the disclosure of which is incorporated by reference herein.

Additional examples of instruments that may be incorporated with a robotic surgical system are described in U.S. Pub. No. 2013/0012957, entitled "Automated End Effector Component Reloading System for Use with a Robotic System, published Jan. 10, 2013, issued as U.S. Pat. No. 8,844,789 on Sep. 30, 2014, the disclosure of which is incorporated by reference herein; U.S. Pub. No. 2012/0199630, entitled "Robotically-Controlled Surgical Instrument with Force-Feedback Capabilities," published Aug. 9, 2012, issued as U.S. Pat. No. 8,820,605 on Sep. 20, 2014, the disclosure of which is incorporated by reference herein; U.S. Pub. No. 2012/0132450, entitled "Shiftable Drive Interface for Robotically-Controlled Surgical Tool," published May 31, 2012, issued as U.S. Pat. No. 8,616,431 on Dec. 31, 2013, the disclosure of which is incorporated by reference herein; U.S. Pub. No. 2012/0199633, entitled "Surgical Stapling Instruments with Cam-Driven Staple Deployment Arrangements," published Aug. 9, 2012, issued as U.S. Pat. No. 8,573,461 on Nov. 5, 2013, the disclosure of which is incorporated by reference herein; U.S. Pub. No. 2012/0199631, entitled "Robotically-Controlled Motorized Surgical End Effector System with Rotary Actuated Closure Systems Having Variable Actuation Speeds," published Aug. 9, 2012, issued as U.S. Pat. No. 8,602,288 on Dec. 10, 2013, the disclosure of which is incorporated by reference herein; U.S. Pub. No. 2012/0199632, entitled "Robotically-Controlled Surgical Instrument with Selectively Articulatable End Effector," published Aug. 9, 2012, issued as U.S. Pat. No. 9,301,759 on Apr. 5, 2016, the disclosure of which is incorporated by reference herein; U.S. Pub. No. 2012/0203247, entitled "Robotically-Controlled Surgical End Effector System," published Aug. 9, 2012, issued as U.S. Pat. No. 8,783,541 on Jul. 22, 2014, the disclosure of which is incorporated by reference herein; U.S. Pub. No. 2012/0211546, entitled "Drive Interface for Operably Coupling a Manipulatable Surgical Tool to a Robot," published Aug. 23, 2012; issued as U.S. Pat. No. 8,479,969 on Jul. 9, 2013, the disclosure of which is incorporated by reference herein; U.S. Pub. No. 2012/0138660, entitled "Robotically-Controlled Cable-Based Surgical End Effectors," published Jun. 7, 2012, issued as U.S. Pat. No. 8,800,838 on Aug. 12, 2014 the disclosure of which is incorporated by reference herein; U.S. Pub. No. 2012/0205421, entitled "Robotically-Controlled Surgical End Effector System with Rotary Actuated Closure Systems," published Aug. 16, 2012, issued as U.S. Pat. No. 8,573,465 on Nov. 5, 2013, the disclosure of which is incorporated by reference herein; U.S. patent application Ser. No. 13/443,101, entitled "Control Interface for Laparoscopic Suturing Instrument," filed Apr. 10, 2012, published as U.S. Pub. No. 2013/0267969 on Oct. 10, 2013, issued as U.S. Pat. No. 9,814,457 on Nov. 14, 2017, the disclosure of which is incorporated by reference herein; and U.S. Provisional Pat. App. No. 61/597,603, entitled "Robotically Controlled Surgical Instrument," filed Feb. 10, 2012, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 12 depicts a left side elevational view of the instrument of FIG. 4, with the top cover removed;

FIG. 13 depicts a right side elevational view of the instrument of FIG. 4, with the top cover removed;

FIG. 16 depicts a partial top plan view of the shaft assembly of FIG. 15;

FIG. 17 depicts a partial side elevational view of the shaft assembly of FIG. 15;

FIG. 46B depicts a partial perspective view of the instrument of FIG. 37, showing the shaft assembly coupled with the interface assembly;

Figure 1:
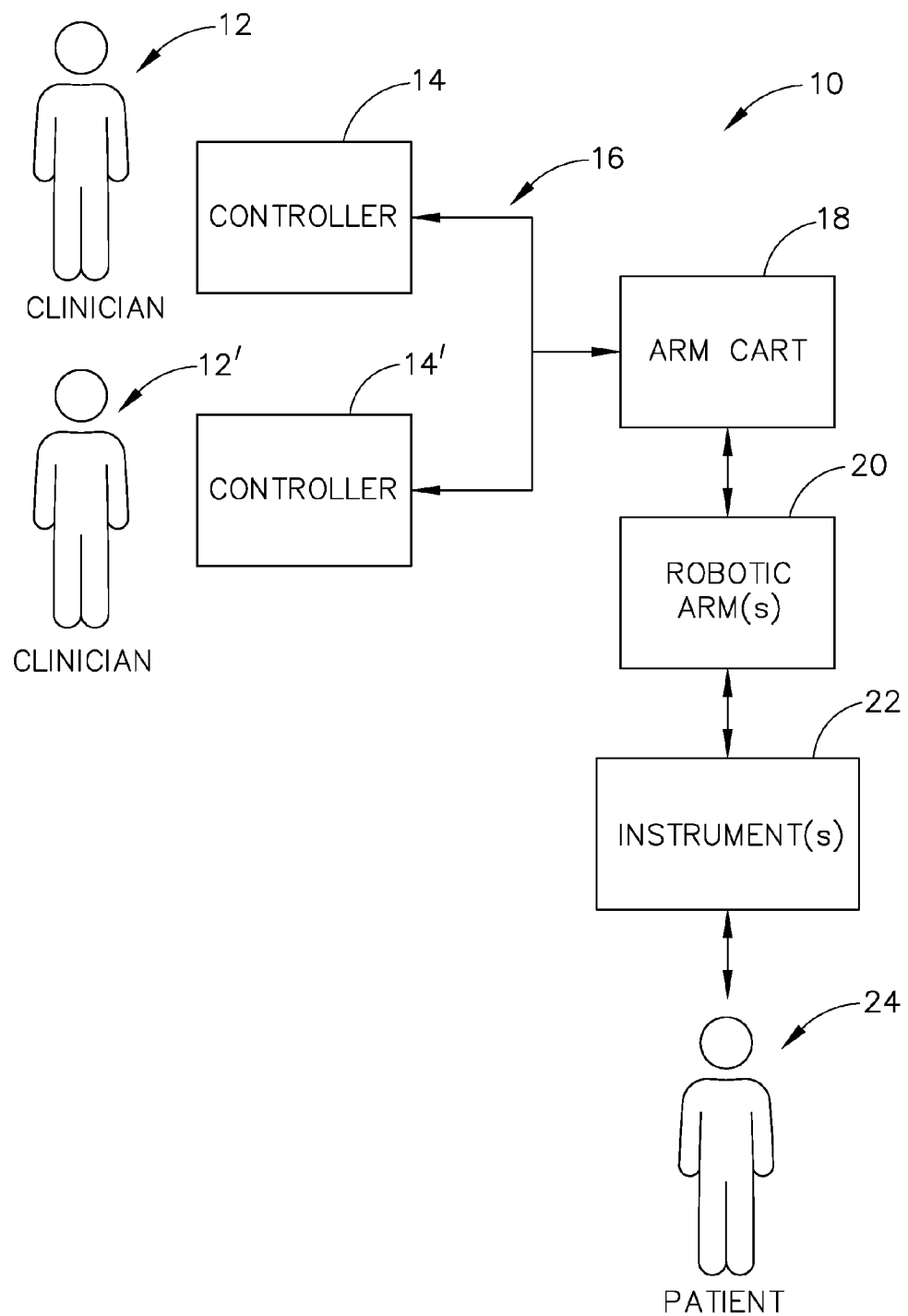
FIG. 1 depicts a block diagram of an exemplary robotic surgical system.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a robotic surgical driver comprising a proximal housing having an interface that mechanically and electrically couples with a surgical instrument having a distal surgical end effector. The term "proximal" refers the position of an element closer to the robotic surgical driver housing and the term "distal" refers to the position of an element closer to the surgical end effector of the surgical instrument and further away from the housing.

I. Exemplary Robotic Surgical System Overview

FIG. 1 illustrates an exemplary robotic surgical system (10). System (10) comprises at least one controller (14) and at least one arm cart (18). Arm cart (18) is mechanically and/or electrically coupled to one or more robotic manipulators or arms (20). Each robotic arm (20) comprises one or more surgical instruments (22) for performing various surgical tasks on a patient (24). Operation of arm cart (18), including arms (20) and instruments (22), may be directed by a clinician (12) from controller (14). In some examples, a second controller (14'), operated by a second clinician (12'), may also direct operation of the arm cart (18) in conjunction with the first clinician (12'). For example, each of the clinicians (12, 12') may control different arms (20) of the cart or, in some cases, complete control of arm cart (18) may be passed between the clinicians (12, 12'). In some examples, additional arm carts (not shown) may be utilized on the patient (24). These additional arm carts may be controlled by one or more of the controllers (14, 14').

Arm cart(s) (18) and controllers (14, 14') may be in communication with one another via a communications link (16), which may be any suitable type of wired and/or wireless communications link carrying any suitable type of signal (e.g., electrical, optical, infrared, etc.) according to any suitable communications protocol. Communications link (16) may be an actual physical link or it may be a logical link that uses one or more actual physical links. When the link is a logical link the type of physical link may be a data link, uplink, downlink, fiber optic link, point-to-point link, for example, as is well known in the computer networking art to refer to the communications facilities that connect nodes of a network.

Figure 2:
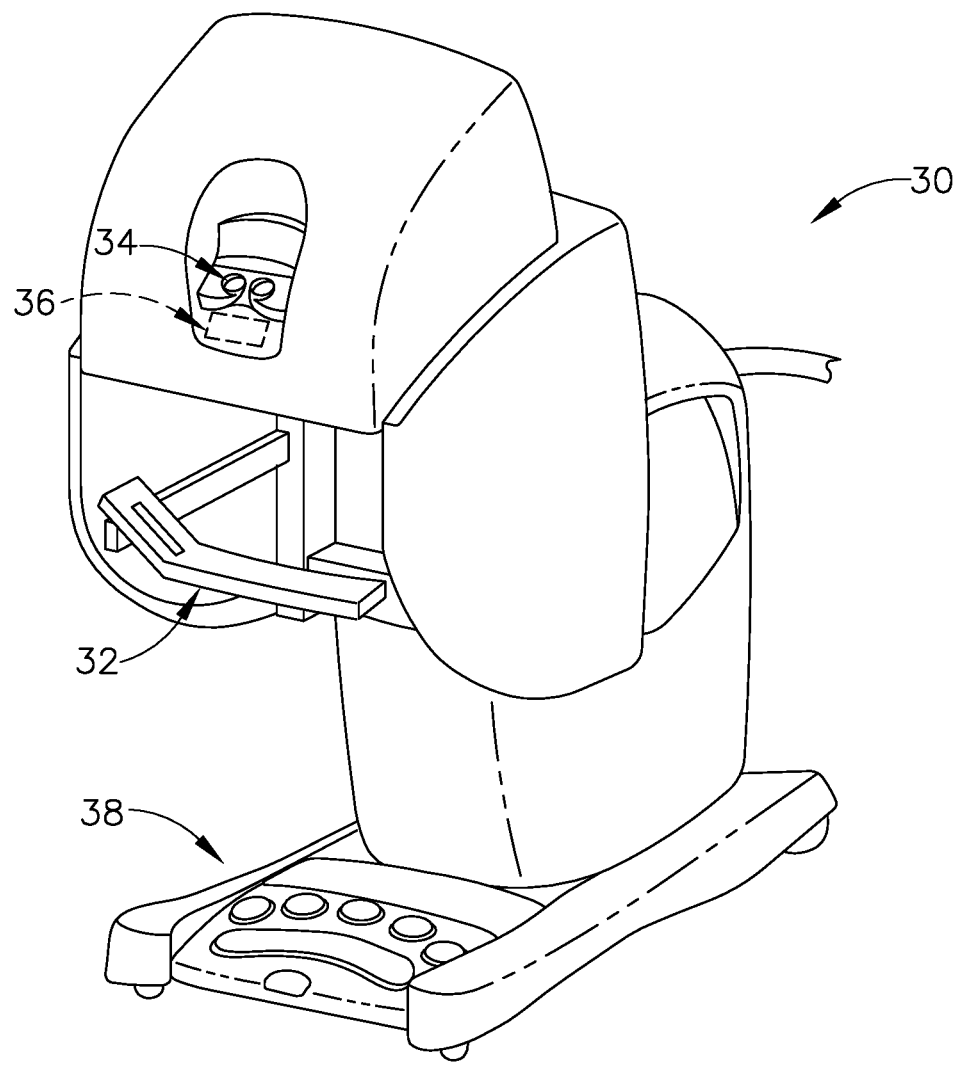
FIG. 2 depicts a perspective view of an exemplary controller of the system of FIG. 1.

FIG. 2 shows an exemplary controller (30) that may serve as a controller (14) of system (10). In this example, controller (30) generally includes user input assembly (32) having precision user input features (not shown) that are grasped by the surgeon and manipulated in space while the surgeon views the surgical procedure via a stereo display (34). The user input features of user input assembly (32) may include manual input devices that move with multiple degrees of freedom; and that include an actuatable handle for intuitively actuating tools (e.g., for closing grasping saws, applying an electrical potential to an electrode, etc). Controller (30) of the present example also includes an array of footswitches (38) providing additional control of arms (20) and instruments (22) to the surgeon. Display (34) may show views from one or more endoscopes viewing the surgical site within the patient and/or any other suitable view(s). In addition, a feedback meter (36) may be viewed through the display (34) and provide the surgeon with a visual indication of the amount of force being applied to a component of instrument (22) (e.g., a cutting member or clamping member, etc.). Other sensor arrangements may be employed to provide controller (30) with an indication as to whether a staple cartridge has been loaded into an end effector of instrument (22), whether an anvil of instrument (22) has been moved to a closed position prior to firing, and/or some other operational condition of instrument (22).

Figure 3:
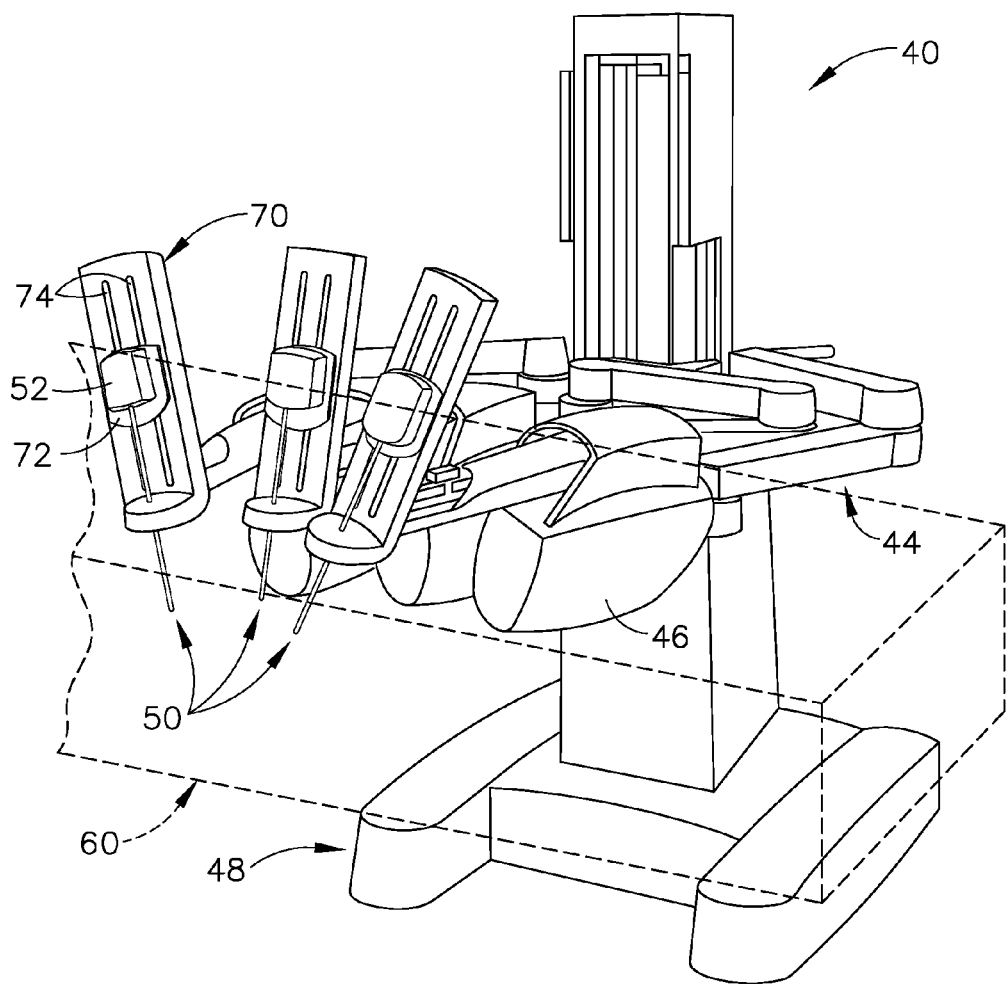
FIG. 3 depicts a perspective view of an exemplary robotic arm cart of the system of FIG. 1.
Figure 4:
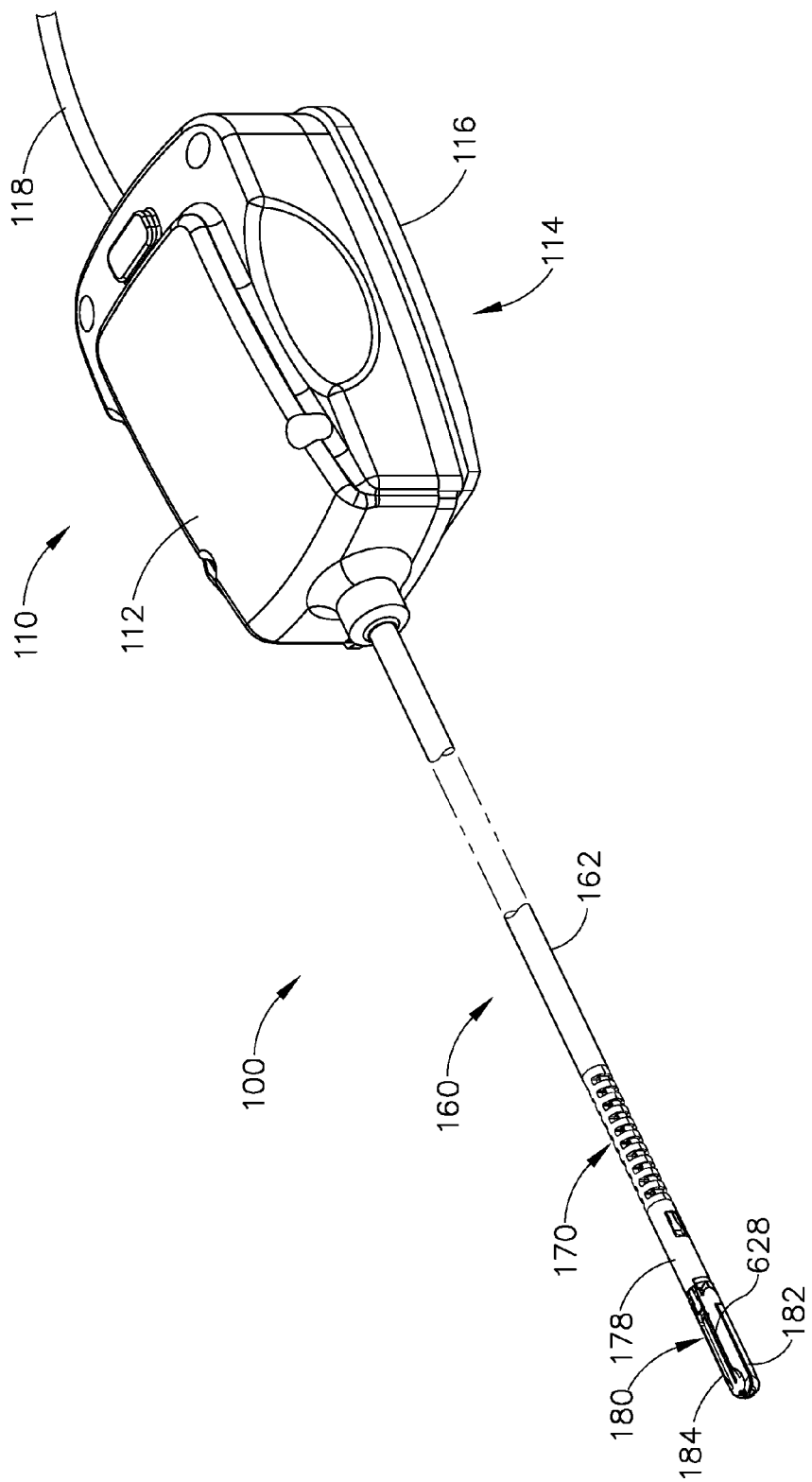
FIG. 4 depicts a perspective view of an exemplary surgical instrument suitable for incorporation with the system of FIG. 1.

FIG. 3 shows an exemplary robotic arm cart (40) that may serve as of arm cart (18) of system (10). In this example, arm cart (40) is operable to actuate a plurality of surgical instruments (50). While three instruments (50) are shown in this example, it should be understood that arm cart (40) may be operable to support and actuate any suitable number of surgical instruments (50). Surgical instruments (50) are each supported by a series of manually articulatable linkages, generally referred to as set-up joints (44), and a robotic manipulator (46). These structures are herein illustrated with protective covers extending over much of the robotic linkage. These protective covers may be optional, and may be limited in size or entirely eliminated in some versions to minimize the inertia that is encountered by the servo mechanisms used to manipulate such devices, to limit the volume of moving components so as to avoid collisions, and to limit the overall weight of cart (40).

Each robotic manipulator (46) terminates at an instrument platform (70), which is pivotable, rotatable, and otherwise movable by manipulator (46). Each platform includes an instrument dock (72) that is slidable along a pair of tracks (74) to further position instrument (50). Such sliding is motorized in the present example. Each instrument dock (72) includes mechanical and electrical interfaces that couple with an interface assembly (52) of instrument (50). By way of example only, dock (72) may include four rotary outputs that couple with complementary rotary inputs of interface assembly (52). Such rotary drive features may drive various functionalities in instrument (50), such as is described in various references cited herein and/or as is described in greater detail below. Electrical interfaces may establish communication via physical contact, inductive coupling, and/or otherwise; and may be operable to provide electrical power to one or more features in instrument (50), provide commands and/or data communication to instrument (50), and/or provide commands and/or data communication from instrument (50). Various suitable ways in which an instrument dock (72) may mechanically and electrically communicate with an interface assembly (52) of an instrument (50) will be apparent to those of ordinary skill in the art in view of the teachings herein. It should also be understood that instrument (50) may include one or more cables that couple with a separate power source and/or control unit, to provide communication of power and/or commands/data to/from instrument (50).

Arm cart (40) of the present example also includes a base (48) that is movable (e.g., by a single attendant) to selectively position arm cart (40) in relation to a patient. Cart (40) may generally have dimensions suitable for transporting the cart (40) between operating rooms. Cart (40) may be configured to fit through standard operating room doors and onto standard hospital elevators. In some versions, an automated instrument reloading system (not shown) may also be positioned in or near the work envelope (60) of arm cart (40), to selectively reload components (e.g., staple cartridges, etc.) of instruments (50).

In addition to the foregoing, it should be understood that one or more aspects of system (10) may be constructed in accordance with at least some of the teachings of U.S. Pat. No. 5,792,135; U.S. Pat. No. 5,817,084; U.S. Pat. No. 5,878,193; U.S. Pat. No. 6,231,565; U.S. Pat. No. 6,783,524; U.S. Pat. No. 6,364,888; U.S. Pat. No. 7,524,320; U.S. Pat. No. 7,691,098; U.S. Pat. No. 7,806,891; U.S. Pat. No. 7,824,401; and/or U.S. Pub. No. 2013/0012957. Issued as U.S. Pat. No. 8,844,789 on Sep. 30, 2014. The disclosures of each of the foregoing U.S. Patents and U.S. Patent Publication are incorporated by reference herein. Still other suitable features and operabilities that may be incorporated into system (10) will be apparent to those of ordinary skill in the art in view of the teachings herein.

II. Exemplary Electrosurgical Instrument with Articulation Feature

FIGS. 4-13 show an exemplary electrosurgical instrument (100) that may be used as at least one instrument (50) within system (10). At least part of instrument (100) may be constructed and operable in accordance with at least some of the teachings of U.S. Pat. No. 6,500,176; U.S. Pat. No. 7,112,201; U.S. Pat. No. 7,125,409; U.S. Pat. No. 7,169,146; U.S. Pat. No. 7,186,253; U.S. Pat. No. 7,189,233; U.S. Pat. No. 7,220,951; U.S. Pat. No. 7,309,849; U.S. Pat. No. 7,311,709; U.S. Pat. No. 7,354,440; U.S. Pat. No. 7,381,209; U.S. Pub. No. 2011/0087218, issued as U.S. Pat. No. 8,939,974 on Jan. 27, 2015; U.S. Pub. No. 2012/0116379, issued as U.S. Pat. No. 9,161,803 on Oct. 20, 2015; U.S. Pub. No. 2012/0078243, issued as U.S. Pat. No. 9,877,720 on Jan. 30, 2018; U.S. Pub. No. 2012/0078247, issued as U.S. Pat. No. 9,402,682 on Aug. 2, 2016; U.S. Pub. No. 2013/0030428, issued as U.S. Pat. No. 9,089,327 on Jul. 28, 2015; and/or U.S. Pub. No. 2013/0023868, issued as U.S. Pat. No. 9,545,243 on Jan. 17, 2017. As described therein and as will be described in greater detail below, instrument (100) is operable to cut tissue and seal or weld tissue (e.g., a blood vessel, etc.) substantially simultaneously. In other words, instrument (100) operates similar to an endocutter type of stapler, except that instrument (100) provides tissue welding through application of bipolar RF energy instead of providing lines of staples to join tissue. It should also be understood that instrument (100) may have various structural and functional similarities with the ENSEAL® Tissue Sealing Device by Ethicon Endo-Surgery, Inc., of Cincinnati, Ohio. Furthermore, instrument (100) may have various structural and functional similarities with the devices taught in any of the other references that are cited and incorporated by reference herein. To the extent that there is some degree of overlap between the teachings of the references cited herein, the ENSEAL® Tissue Sealing Device by Ethicon Endo-Surgery, Inc., of Cincinnati, Ohio, and the following teachings relating to instrument (100), there is no intent for any of the description herein to be presumed as admitted prior art. Several teachings herein will in fact go beyond the scope of the teachings of the references cited herein and the ENSEAL® Tissue Sealing Device by Ethicon Endo-Surgery, Inc., of Cincinnati, Ohio.

Instrument (100) of the present example includes an interface assembly (110), a shaft assembly (160), an articulation section (170), and an end effector (180). Interface assembly (110) is configured to couple with a dock (72) of robotic arm cart (40) and is thereby further operable to drive articulation section (170) and end effector (180) as will be described in greater detail below. As will also be described in greater detail below, instrument (100) is operable to articulate end effector (180) to provide a desired positioning relative to tissue (e.g., a large blood vessel, etc.), then sever the tissue and apply bipolar RF energy to the tissue with end effector (180) to thereby seal the tissue.

A. Exemplary Shaft Assembly and Articulation Section

Figure 5:
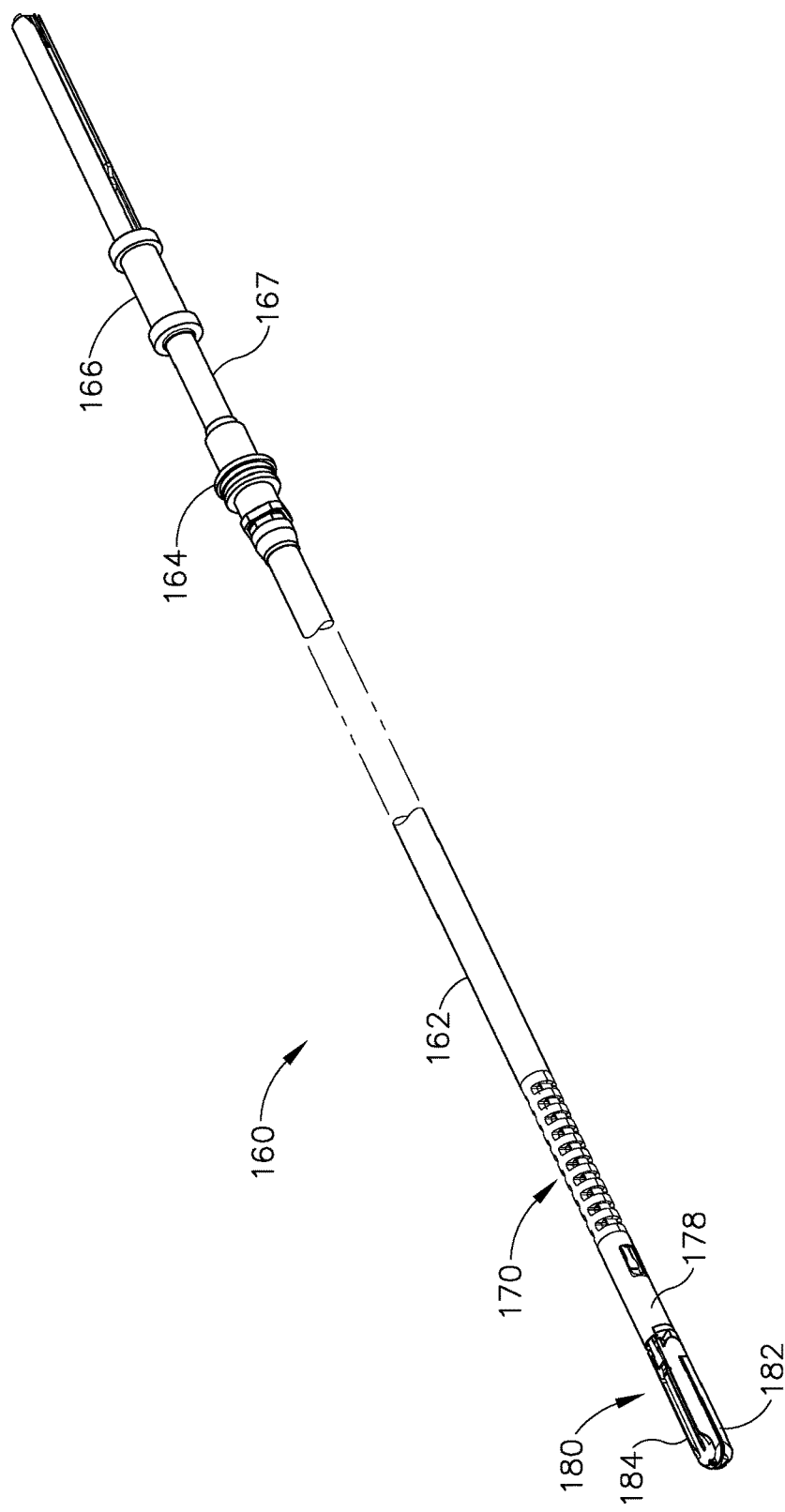
FIG. 5 depicts a perspective view of the shaft assembly of the surgical instrument of FIG. 4.

Shaft assembly (160) of the present example extends distally from interface assembly (110). Articulation section (170) is located at the distal end of shaft assembly (160), with end effector (180) being located distal to articulation section (170). Shaft assembly (160) includes an outer sheath (162) that encloses drive features and electrical features that couple interface assembly (110) with articulation section (170) and end effector (180). As best seen in FIG. 5, shaft assembly (160) further includes a unitary rotary coupling (164) and a firing beam coupling (166). Shaft assembly (160) is rotatable about the longitudinal axis defined by sheath (162), relative to interface assembly (110), via rotary coupling (164). Such rotation may provide rotation of end effector (180), articulation section (170), and shaft assembly (160) unitarily. In some other versions, rotary coupling (164) is operable to rotate end effector (180) without rotating any portion of shaft assembly (160) that is proximal of articulation section (170). As another merely illustrative example, instrument (100) may include one rotation control that provides rotatability of shaft assembly (160) and end effector (180) as a single unit; and another rotation control that provides rotatability of end effector (180) without rotating any portion of shaft assembly (160) that is proximal of articulation section (170). Other suitable rotation schemes will be apparent to those of ordinary skill in the art in view of the teachings herein. Of course, rotatable features may simply be omitted if desired.

Articulation section (170) is operable to selectively position end effector (180) at various angles relative to the longitudinal axis defined by sheath (162). Articulation section (170) may take a variety of forms. By way of example only, articulation section (170) may be configured in accordance with one or more teachings of U.S. Pub. No. 2012/0078247, issued as U.S. Pat. No. 9,402,682 on Aug. 2, 2016, the disclosure of which is incorporated by reference herein. As another merely illustrative example, articulation section (170) may be configured in accordance with one or more teachings of U.S. Pub. No. 2012/0078248, entitled "Articulation Joint Features for Articulating Surgical Device," published Mar. 29, 2012, now U.S. Pat. No. 9,220,559, issued Dec. 29, 2015, the disclosure of which is incorporated by reference herein. Various other suitable forms that articulation section (170) may take will be apparent to those of ordinary skill in the art in view of the teachings herein. It should also be understood that some versions of instrument (10) may simply lack articulation section (170).

Figure 6:
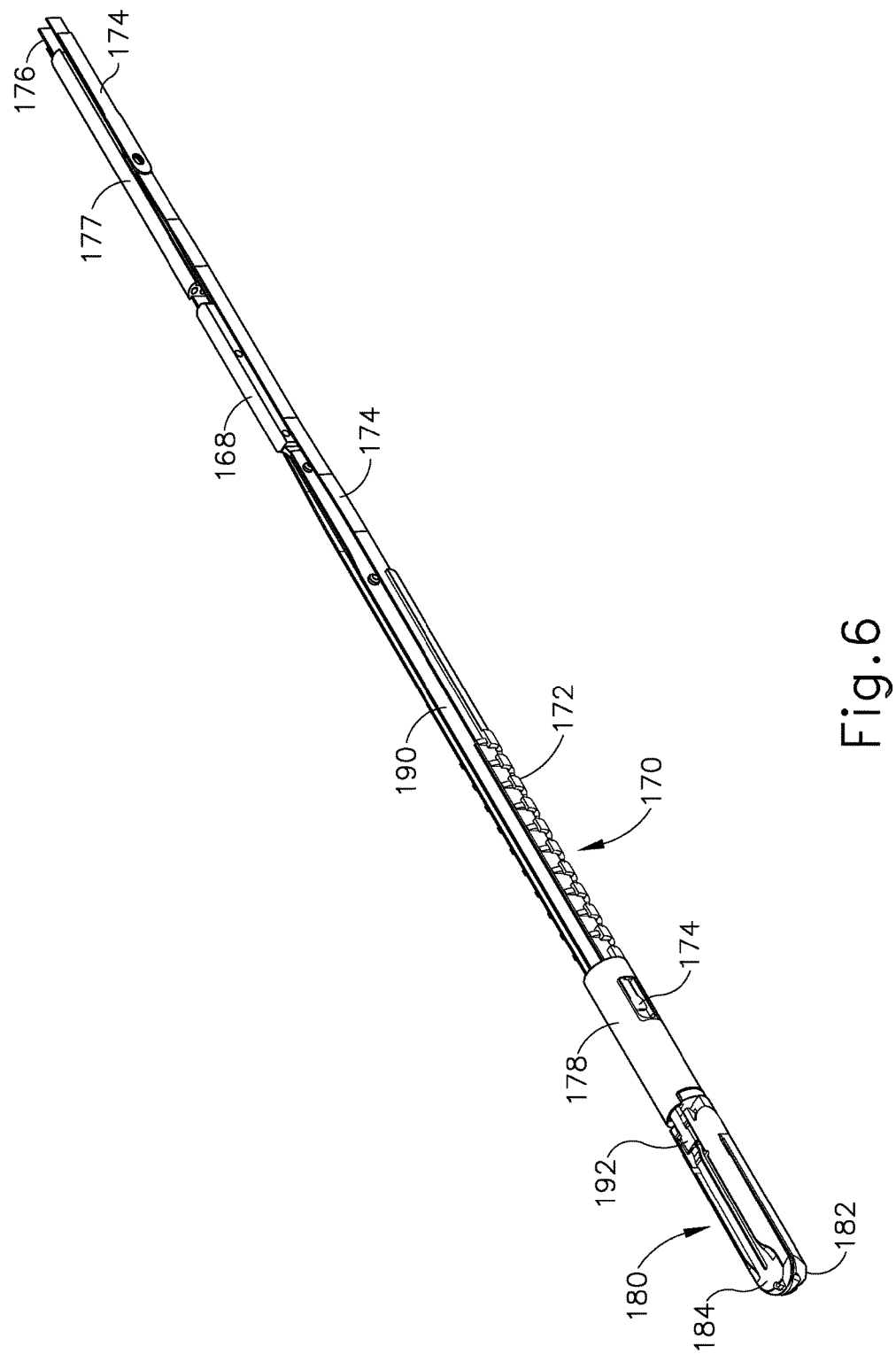
FIG. 6 depicts a perspective view of components of the shaft assembly of FIG. 5.
Figure 7:
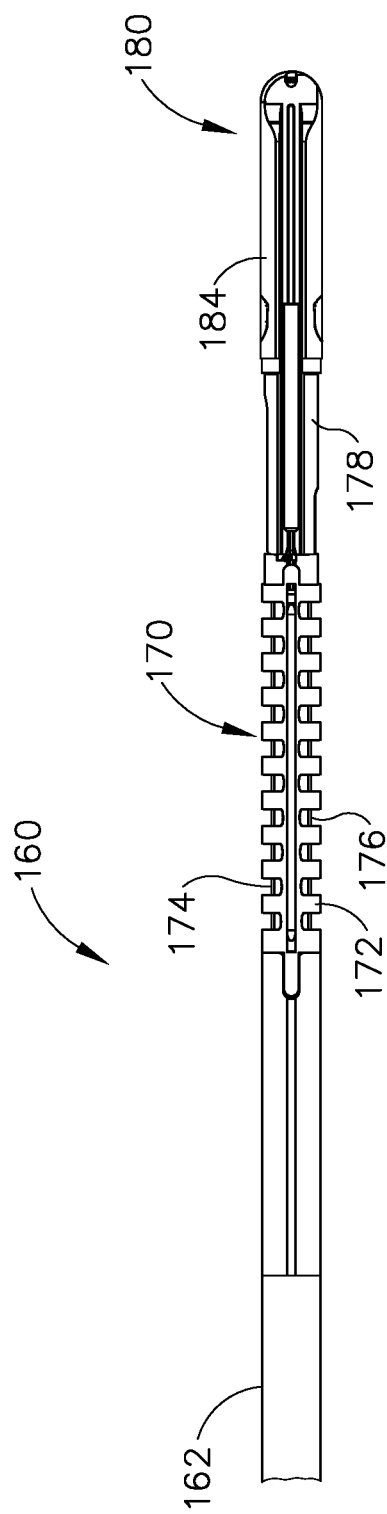
FIG. 7 depicts a top plan view of a distal portion of the shaft assembly of FIG. 5.

As best seen in FIGS. 6-7, articulation section (170) of the present example comprises a ribbed body (172) with a pair of articulation beams (174, 176) extending through ribbed body (172). An upper half of ribbed body (172) is omitted in FIG. 6. Articulation beams (174, 176) are distally anchored within a tube (178) that is positioned between end effector (180) and articulation section (170). Articulation beams (174, 176) are operable to articulate end effector (180) by laterally deflecting end effector (180) away from the longitudinal axis defined by sheath (162). In particular, and referring to the view shown in FIG. 7, end effector (180) will deflect toward articulation beam (174) when articulation beam (174) is retracted proximally while articulation beam (176) is advanced distally. End effector (180) will deflect toward articulation beam (176) when articulation beam (176) is retracted proximally while articulation beam (174) is advanced distally. Merely illustrative examples of how articulation beams (174, 176) may be opposingly translated will be described in greater detail below, while still other examples will be apparent to those of ordinary skill in the art in view of the teachings herein. As best seen in FIG. 6, a spacer body (177) is positioned between articulation beams (174, 176) and is operable to maintain beams (174, 176) in a substantially straight, separated relationship.

B. Exemplary End Effector

End effector (180) of the present example comprises a first jaw (182) and a second jaw (184). In the present example, first jaw (182) is substantially fixed relative to shaft assembly (160); while second jaw (184) pivots relative to shaft assembly (160), toward and away from first jaw (182). In some versions, actuators such as rods or cables, etc., may extend through sheath (162) and be joined with second jaw (184) at a pivotal coupling, such that longitudinal movement of the actuator rods/cables/etc. through shaft assembly (160) provides pivoting of second jaw (184) relative to shaft assembly (160) and relative to first jaw (182). Of course, jaws (182, 184) may instead have any other suitable kind of movement and may be actuated in any other suitable fashion. By way of example only, and as will be described in greater detail below, jaws (182, 184) may be actuated and thus closed by longitudinal translation of a firing beam (190), such that actuator rods/cables/etc. may simply be eliminated in some versions.

Figure 8:
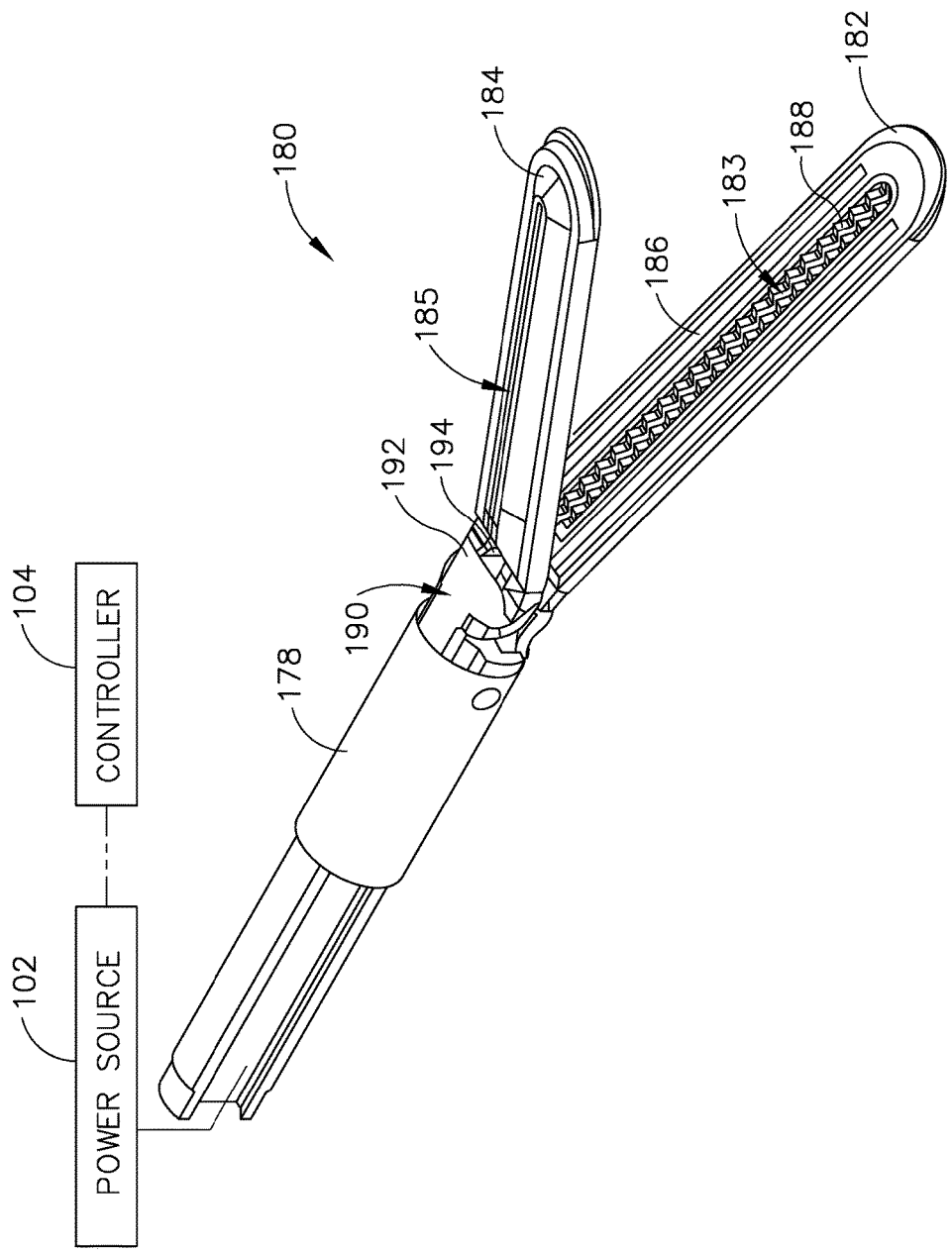
FIG. 8 depicts a perspective view of the end effector of the shaft assembly of FIG. 5, in an open configuration.
Figure 9:
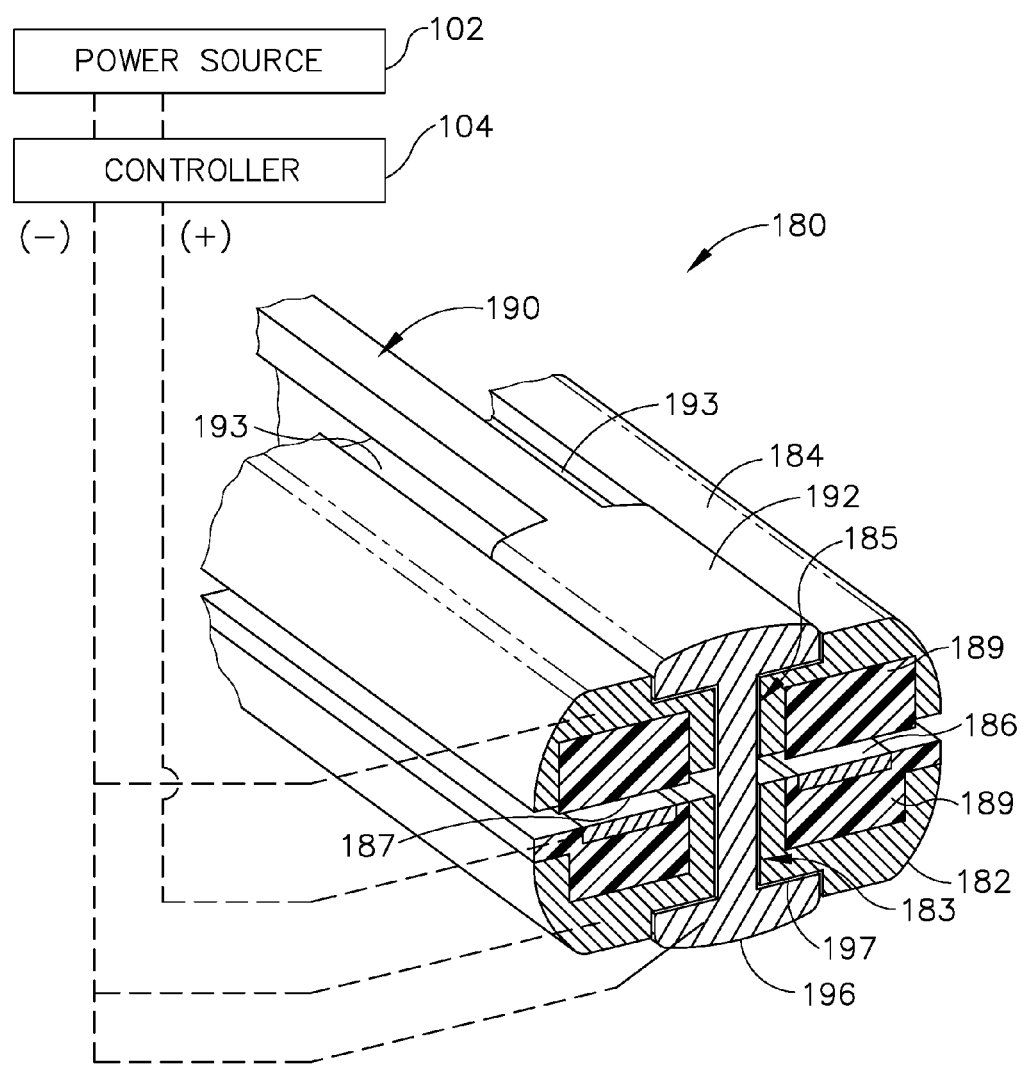
FIG. 9 depicts a perspective view in cross-section of the end effector of FIG. 8, taken along a lateral plane, with the end effector in a closed configuration.

As best seen in FIGS. 8-9, first jaw (182) defines a longitudinally extending elongate slot (183); while second jaw (184) also defines a longitudinally extending elongate slot (185). In addition, the top side of first jaw (182) presents a first electrode surface (186); while the underside of second jaw (184) presents a second electrode surface (187). Electrode surface (186, 187) are in communication with an electrical source (102) via one or more conductors (not shown) that extend along the length of shaft assembly (160). Electrical source (102) is operable to deliver RF energy to first electrode surface (186) at a first polarity and to second electrode surface (187) at a second (opposite) polarity, such that RF current flows between electrode surface (186, 187) and thereby through tissue captured between jaws (182, 184). In some versions, firing beam (190) serves as an electrical conductor that cooperates with electrode surface (186, 187) (e.g., as a ground return) for delivery of bipolar RF energy captured between jaws (182, 184).

Electrical source (102) may be external to instrument (100) or may be integral with instrument (100), as described in one or more references cited herein or otherwise. A controller (104) regulates delivery of power from electrical source (102) to electrode surfaces (186, 187). Controller (104) may also be external to instrument (100) or may be integral with electrosurgical instrument (100), as described in one or more references cited herein or otherwise. It should also be understood that electrode surfaces (186, 187) may be provided in a variety of alternative locations, configurations, and relationships. It should also be understood that power source (102) and/or controller (104) may be configured in accordance with at least some of the teachings of U.S. Provisional Pat. App. No. 61/550,768, entitled "Medical Instrument," filed Oct. 24, 2011, the disclosure of which is incorporated by reference herein; U.S. Pub. No. 2011/0082486, entitled "Devices and Techniques for Cutting and Coagulating Tissue," published Apr. 7, 2011, now U.S. Pat. No. 9,089,360, issued Jul. 28, 2015, the disclosure of which is incorporated by reference herein; U.S. Pub. No. 2011/0087212, entitled "Surgical Generator for Ultrasonic and Electrosurgical Devices," published Apr. 14, 2011 now U.S. Pat. No. 8,986,302, issued Mar. 24, 2015, the disclosure of which is incorporated by reference herein; U.S. Pub. No. 2011/0087213, entitled "Surgical Generator for Ultrasonic and Electrosurgical Devices," published Apr. 14, 2011, now U.S. Pat. No. 8,951,248, issued Feb. 10, 2015, the disclosure of which is incorporated by reference herein; U.S. Pub. No. 2011/0087214, entitled "Surgical Generator for Ultrasonic and Electrosurgical Devices," published Apr. 14, 2011, now U.S. Pat. No. 9,039,695, issued May 26, 2015, the disclosure of which is incorporated by reference herein; U.S. Pub. No. 2011/0087215, entitled "Surgical Generator for Ultrasonic and Electrosurgical Devices," published Apr. 14, 2011, now U.S. Pat. No. 9,050,093, issued Jun. 9, 2015, the disclosure of which is incorporated by reference herein; U.S. Pub. No. 2011/0087216, entitled "Surgical Generator for Ultrasonic and Electrosurgical Devices," published Apr. 14, 2011, now U.S. Pat. No. 8,956,349, issued Feb. 7, 2015, the disclosure of which is incorporated by reference herein; and/or U.S. Pub. No. 2011/0087217, entitled "Surgical Generator for Ultrasonic and Electrosurgical Devices," published Apr. 14, 2011, now U.S. Pat. No. 9,060,776, issued Jun. 23, 2015, the disclosure of which is incorporated by reference herein. Other suitable configurations for power source (102) and controller (104) will be apparent to those of ordinary skill in the art in view of the teachings herein.

As best seen in FIG. 9, the lower side of first jaw (182) includes a longitudinally extending recess (197) adjacent to slot (183); while the upper side of second jaw (184) includes a longitudinally extending recess (193) adjacent to slot (185). FIG. 2 shows the upper side of first jaw (182) including a plurality of teeth serrations (188). It should be understood that the lower side of second jaw (184) may include complementary serrations that nest with serrations (188), to enhance gripping of tissue captured between jaws (182, 184) without necessarily tearing the tissue. Of course, serrations (188) may take any other suitable form or may be simply omitted altogether. It should also be understood that serrations (188) may be formed of an electrically non-conductive, or insulative, material, such as plastic, glass, and/or ceramic, for example, and may include a treatment such as polytetrafluoroethylene, a lubricant, or some other treatment to substantially prevent tissue from getting stuck to jaws (182, 184).

With jaws (182, 184) in a closed position, shaft assembly (160) and end effector (180) are sized and configured to fit through trocars having various inner diameters, such that instrument (100) is usable in minimally invasive surgery, though of course instrument (100) could also be used in open procedures if desired. By way of example only, with jaws (182, 184) in a closed position, shaft assembly (160) and end effector (180) may present an outer diameter of approximately 5 mm. Alternatively, shaft assembly (160) and end effector (180) may present any other suitable outer diameter (e.g., between approximately 2 mm and approximately 20 mm, etc.).

In some versions, end effector (180) includes one or more sensors (not shown) that are configured to sense a variety of parameters at end effector (180), including but not limited to temperature of adjacent tissue, electrical resistance or impedance of adjacent tissue, voltage across adjacent tissue, forces exerted on jaws (182, 184) by adjacent tissue, etc. By way of example only, end effector (180) may include one or more positive temperature coefficient (PTC) thermistor bodies (189) (e.g., PTC polymer, etc.), located adjacent to electrodes (186, 187) and/or elsewhere. Data from sensors may be communicated to controller (104). Controller (104) may process such data in a variety of ways. By way of example only, controller (104) may modulate or otherwise change the RF energy being delivered to electrode surface (186, 187), based at least in part on data acquired from one or more sensors at end effector (180). In addition or in the alternative, controller (104) may alert the user to one or more conditions via an audio and/or visual feedback device (e.g., speaker, lights, display screen, etc.), based at least in part on data acquired from one or more sensors at end effector (180). It should also be understood that some kinds of sensors need not necessarily be in communication with controller (104), and may simply provide a purely localized effect at end effector (180). For instance, PTC thermistor bodies (189) at end effector (180) may automatically reduce the energy delivery at electrode surface (186, 187) as the temperature of the tissue and/or end effector (180) increases, thereby reducing the likelihood of overheating. In some such versions, a PTC thermistor element is in series with power source (102) and electrode surface (186, 187); and the PTC thermistor provides an increased impedance (reducing flow of current) in response to temperatures exceeding a threshold. Furthermore, it should be understood that electrode surface (186, 187) may be used as sensors (e.g., to sense tissue impedance, etc.). Various kinds of sensors that may be incorporated into instrument (100) will be apparent to those of ordinary skill in the art in view of the teachings herein. Similarly various things that can be done with data from sensors, by controller (104) or otherwise, will be apparent to those of ordinary skill in the art in view of the teachings herein. Other suitable variations for end effector (180) will also be apparent to those of ordinary skill in the art in view of the teachings herein.

Firing beam (190) is longitudinally movable along part of the length of end effector (180). Firing beam (190) is coaxially positioned within shaft assembly (160), extends along part of the the length of shaft assembly (160), and translates longitudinally within shaft assembly (160) (including articulation section (170) in the present example), though it should be understood that firing beam (190) and shaft assembly (160) may have any other suitable relationship. As shown in FIG. 6, firing beam (190) is secured to a firing block (168), such that firing beam (190) and firing block (168) translate unitarily together within sheath (162). Firing block (168) is secured to firing tube (167), which is best seen in FIG. 5. Firing block (168) and firing tube (167) translate unitarily together within sheath (162). Firing beam coupling (166) is secured to firing tube (167), such that translating firing beam coupling (166) will translate firing beam (190) through the above-described couplings.

Firing beam (190) includes a sharp distal blade (194), an upper flange (192), and a lower flange (196). As best seen in FIGS. 8-9, distal blade (194) extends through slots (183, 185) of jaws (182, 184), with upper flange (192) being located above jaw (184) in recess (59) and lower flange (196) being located below jaw (182) in recess (58). The configuration of distal blade (194) and flanges (62, 66) provides an "I-beam" type of cross section at the distal end of firing beam (190). While flanges (192, 196) extend longitudinally only along a small portion of the length of firing beam (190) in the present example, it should be understood that flanges (192, 196) may extend longitudinally along any suitable length of firing beam (190). In addition, while flanges (192, 196) are positioned along the exterior of jaws (182, 184), flanges (192, 196) may alternatively be disposed in corresponding slots formed within jaws (182, 184). For instance, each jaw (182, 184) may define a "T"-shaped slot, with parts of distal blade (194) being disposed in one vertical portion of each "T"-shaped slot and with flanges (192, 196) being disposed in the horizontal portions of the "T"-shaped slots. Various other suitable configurations and relationships will be apparent to those of ordinary skill in the art in view of the teachings herein.

Distal blade (194) is substantially sharp, such that distal blade (194) will readily sever tissue that is captured between jaws (182, 184). Distal blade (194) is also electrically grounded in the present example, providing a return path for RF energy as described elsewhere herein. In some other versions, distal blade (194) serves as an active electrode. In addition or in the alternative, distal blade (194) may be selectively energized with ultrasonic energy (e.g., harmonic vibrations at approximately 55.5 kHz, etc.).

The "I-beam" type of configuration of firing beam (190) provides closure of jaws (182, 184) as firing beam (190) is advanced distally. In particular, flange (192) urges jaw (184) pivotally toward jaw (182) as firing beam (190) is advanced from a proximal position to a distal position, by bearing against recess (193) formed in jaw (184). This closing effect on jaws (182, 184) by firing beam (190) may occur before distal blade (194) reaches tissue captured between jaws (182, 184). Such staging of encounters by firing beam (190) may reduce the force required to actuate firing beam (190) distally through a full firing stroke. In other words, in some such versions, firing beam (190) may have already overcome an initial resistance required to substantially close jaws (182, 184) on tissue before encountering resistance from severing the tissue captured between jaws (182, 184). Of course, any other suitable staging may be provided.

In the present example, flange (192) is configured to cam against a ramp feature at the proximal end of jaw (184) to open jaw (184) when firing beam (190) is retracted to a proximal position and to hold jaw (184) open when firing beam (190) remains at the proximal position. This camming capability may facilitate use of end effector (180) to separate layers of tissue, to perform blunt dissections, etc., by forcing jaws (182, 184) apart from a closed position. In some other versions, jaws (182, 184) are resiliently biased to an open position by a spring or other type of resilient feature. While jaws (182, 184) close or open as firing beam (190) is translated in the present example, it should be understood that other versions may provide independent movement of jaws (182, 184) and firing beam (190). By way of example only, one or more cables, rods, beams, or other features may extend through shaft assembly (160) to selectively actuate jaws (182, 184) independently of firing beam (190).

C. Exemplary Robotic Arm Interface Assembly

FIGS. 4 and 10-13 show interface assembly (110) of the present example in greater detail. As shown, interface assembly (110) comprises a housing (112), a base (114), and a cable (118). Housing (112) comprises a shell that simply encloses drive components. In some versions, housing (112) also includes an electronic circuit board, chip, and/or other feature that is configured to identify instrument (100). Such identification may be carried out through cable (118). Cable (118) is configured to couple with power source (102) and controller (104). A strain relief (119) is provided at the interface of cable (118) and housing (112). It should be noted that housing (112) is omitted from FIGS. 11-13 for the sake of clarity.

Figure 10:
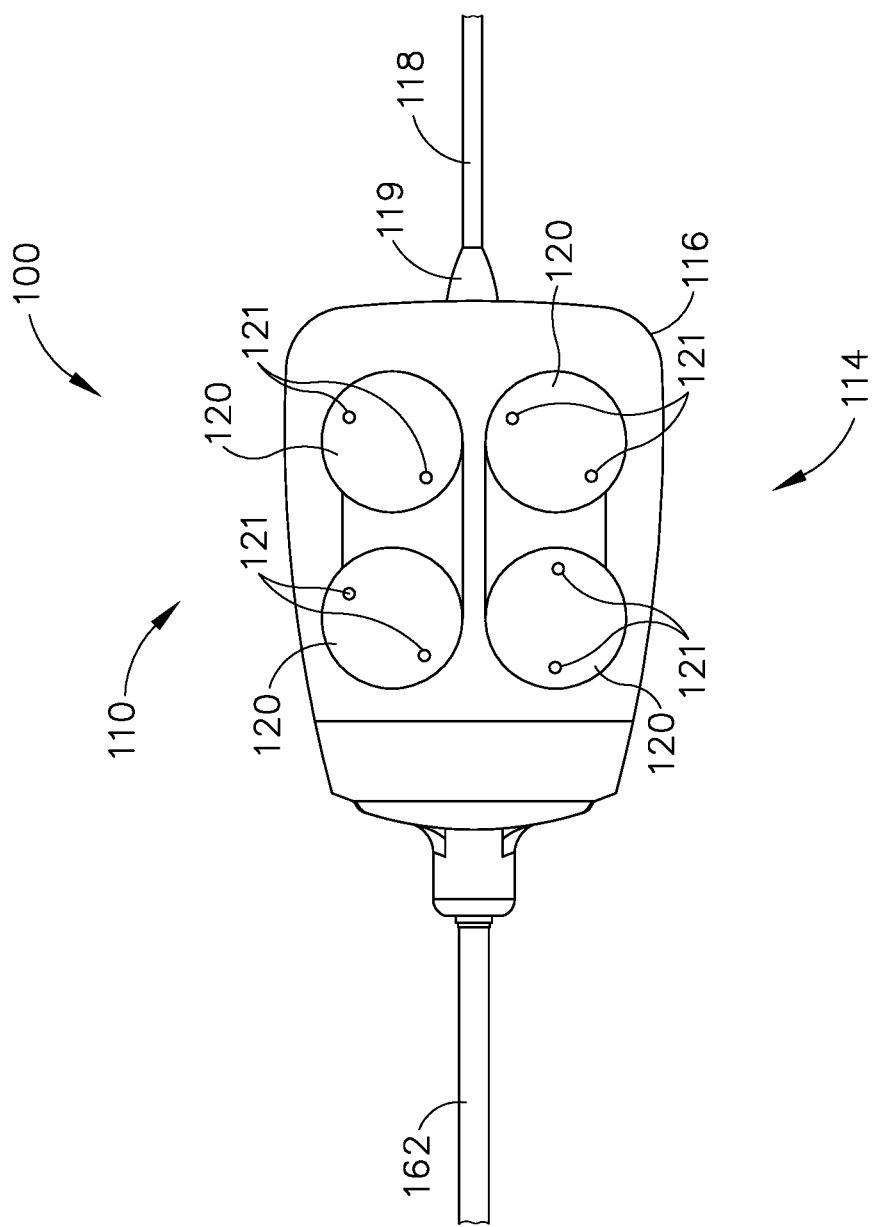
FIG. 10 depicts a bottom plan view of a proximal portion of the instrument of FIG. 4.
Figure 11:
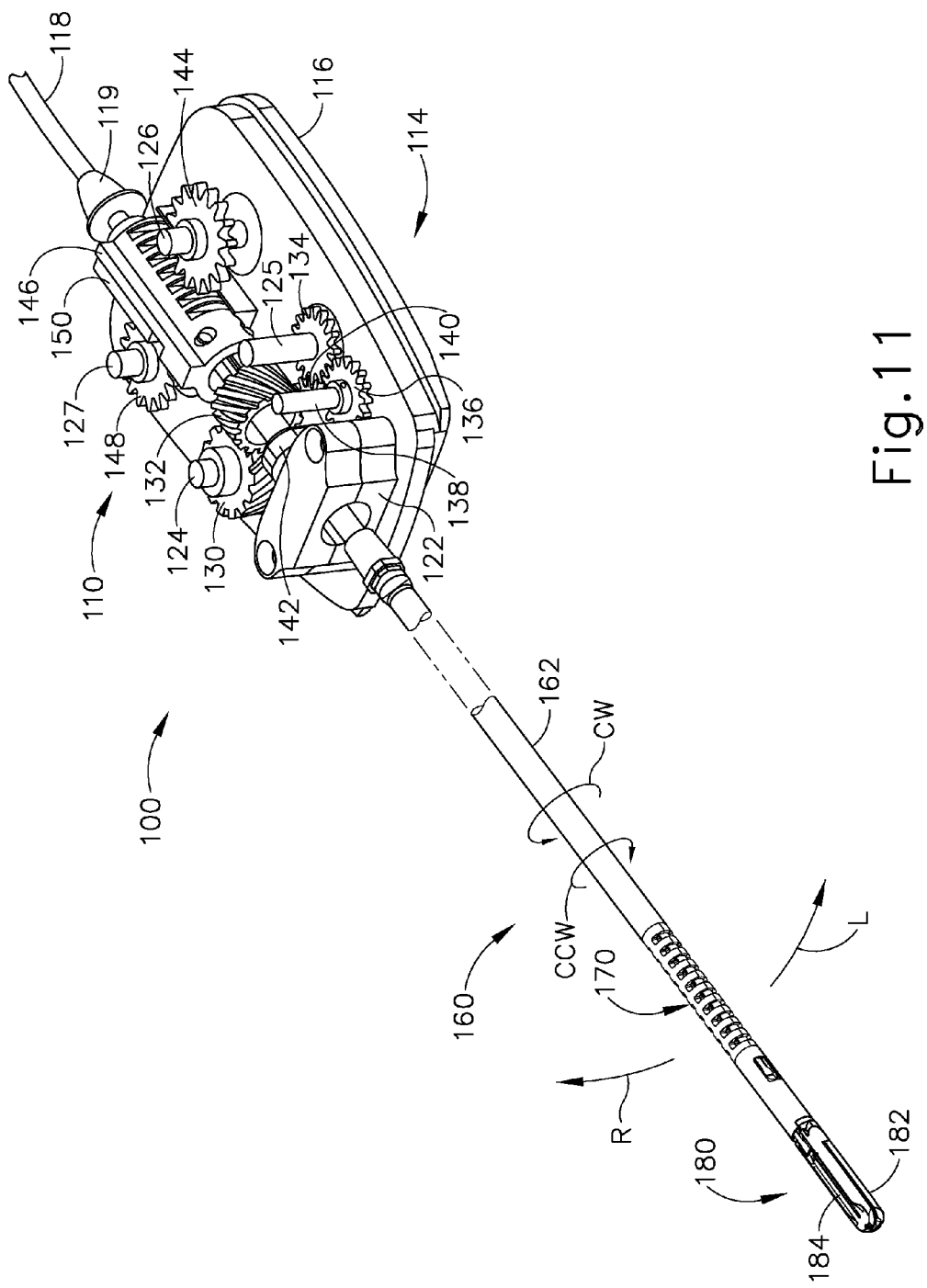
FIG. 11 depicts a perspective view of the instrument of FIG. 4, with a top cover removed.

Base (114) includes a mounting plate (116) that engages dock (72) of robotic arm cart (40). It should be noted that plate (116) is omitted from FIGS. 12-13 for the sake of clarity. While not shown, it should be understood that base (114) may also include one or more electrical contacts and/or other features operable to establish electrical communication with a complementary feature of dock (72). A shaft support structure (122) extends upwardly from base (114) and provides support to shaft assembly (160) (while still allowing shaft assembly (160) to rotate). By way of example only, shaft support structure (122) may include a busing, bearings, and/or other features that facilitate rotation of shaft assembly (160) relative to support structure (122). As shown in FIG. 10, base (114) further includes four drive discs (120) that are rotatable relative to plate (116). Each disc (120) includes a pair of unitary pins (121) that couple with complementary recesses (not shown) in drive elements of dock (72). In some versions, one pin (121) of each pair is closer to the axis of rotation of the corresponding disc (120), to ensure proper angular orientation of disc (120) relative to the corresponding drive element of dock (72). As best seen in FIGS. 11-13, a drive shaft (124, 125, 126, 127) extends unitarily upwardly from each disc (120). As will be described in greater detail below, discs (120) are operable to provide independent rotation of shaft assembly (160), bending of articulation section (170), and translation of firing beam (190), through rotation of drive shafts (124, 125, 126, 127).

As best seen in FIG. 11, a first helical gear (130) is fixedly secured to drive shaft (124), such that rotation of the corresponding disc (120) provides rotation of first helical gear (130). First helical gear (130) meshes with a second helical gear (132), which is fixedly secured to rotary coupling (164). Thus, rotation of first helical gear (130) provides rotation of shaft assembly (160). It should be understood that rotation of first helical gear (130) about a first axis is converted into rotation of second helical gear (132) about a second axis, which is orthogonal to the first axis. A clockwise (CW) rotation of second helical gear (132) results in CW rotation of shaft assembly (160). A counter-clockwise (CCW) rotation of second helical gear (132) results in CCW rotation of shaft assembly (160). Other suitable ways in which shaft assembly (160) may be rotated will be apparent to those of ordinary skill in the art in view of the teachings herein.

As best seen in FIGS. 11-12, a spur gear (134) is fixedly secured to drive shaft (125), such that rotation of the corresponding disc (120) provides rotation of spur gear (134). Spur gear (134) meshes with a first spur pinion (136), which is fixedly secured to a pinion shaft (138). Pinion shaft (138) is supported by base (116) and rotates freely relative to base (116), such that first spur pinion (136) is rotatable as an idler. It should therefore be understood that first spur pinion (136) rotates in response to rotation of spur gear (134). First spur pinion (136) also meshes with a rack (140), which is fixedly secured to a drive block (142). Drive block (142) is secured to firing beam coupling (166). Thus, rotation of first spur pinion (136) is converted to translation of firing beam (190) via rack (140), drive block (142), and firing beam coupling (166). As noted above, firing beam (190) is operable to first close jaws (182, 184) together about tissue during a first range of distal travel of firing beam (190); then sever the tissue clamped between jaws (182, 184) during a first range of distal travel of firing beam (190). Thus tissue may be clamped and severed by rotation of drive shaft (125) via its corresponding disc (120). When this rotation is reversed, firing beam (190) retracts proximally, ultimately opening jaws (182, 184) to release tissue. Other suitable ways in which firing beam (190) may be translated will be apparent to those of ordinary skill in the art in view of the teachings herein.

With respect to articulation control, FIGS. 11-12 show a second spur pinion (144) fixedly secured to drive shaft (126), such that rotation of the corresponding disc (120) provides rotation of second spur pinion (144). Second spur pinion (144) meshes with a left rack (146), which is fixedly secured to articulation beam (174). It should be understood that articulation beam (174) will translate distally or proximally in response to rotation of drive shaft (126). Similarly, FIGS. 11 and 13 show a third spur pinion (148) fixedly secured to drive shaft (127), such that rotation of the corresponding disc (120) provides rotation of third spur pinion (148). Third spur pinion (148) meshes with a right rack (150), which is fixedly secured to articulation beam (176). It should be understood that articulation beam (176) will translate distally or proximally in response to rotation of drive shaft (127).

It should also be understood that drive shafts (126, 127) may be rotated in the same direction simultaneously in order to provide opposing translation of beams (174, 176). For instance, drive shaft (126) may be rotated clockwise to retract beam (174) proximally, with drive shaft (127) being rotated clockwise to advance beam (176) distally, to thereby deflect end effector (180) to the left (L) at articulation section (170). Conversely, drive shaft (126) may be rotated counter-clockwise to advance beam (174) distally, with drive shaft (127) being rotated counter-clockwise to retract beam (176) proximally, to deflect end effector (180) to the left (R) at articulation section (170). Other suitable ways in which end effector (180) may be articulated at articulation section (170) will be apparent to those of ordinary skill in the art in view of the teachings herein. By way of example only, articulation control may be provided in accordance with at least some of the teachings of U.S. Pub. No. 2012/0078243, issued as U.S. Pat. No. 9,877,720 on Jan. 30, 2018, the disclosure of which is incorporated by reference herein; and/or U.S. Pub. No. 2013/0023868, issued as U.S. Pat. No. 9,545,253 on Jan. 17, 2017, the disclosure of which is incorporated by reference herein. It should also be understood that some versions of instrument (100) may simply lack an articulation section (170) and corresponding control.

D. Exemplary Operation

In an exemplary use, arm cart (40) is used to insert end effector (180) into a patient via a trocar. Articulation section (170) is substantially straight when end effector (180) and part of shaft assembly (160) are inserted through the trocar. Drive shaft (124) may be rotated through drive features in dock (72) that are coupled with the corresponding disc (120), to position end effector (180) at a desired angular orientation relative to the tissue. Drive shafts (126, 126) may then be rotated through drive features in dock (72) that are coupled with the corresponding discs (120), to pivot or flex articulation section (170) of shaft assembly (160) in order to position end effector (180) at a desired position and orientation relative to an anatomical structure within the patient.

Two layers of tissue of the anatomical structure are then captured between jaws (182, 184) by rotating drive shaft (125) to advance firing beam (190) distally through a first range of motion. Such layers of tissue may be part of the same natural lumen defining anatomical structure (e.g., blood vessel, portion of gastrointestinal tract, portion of reproductive system, etc.) in a patient. For instance, one tissue layer may comprise the top portion of a blood vessel while the other tissue layer may comprise the bottom portion of the blood vessel, along the same region of length of the blood vessel (e.g., such that the fluid path through the blood vessel before use of instrument (100) is perpendicular to the longitudinal axis defined by end effector (180), etc.). In other words, the lengths of jaws (182, 184) may be oriented perpendicular to (or at least generally transverse to) the length of the blood vessel. As noted above, flanges (192, 196) cammingly act to pivot jaw (182) toward jaw (184) when firing beam (190) is actuated distally by rotating drive shaft (125).

With tissue layers captured between jaws (182, 184) firing beam (190) continues to advance distally in response to continued rotation of drive shaft (125). As firing beam (190) continues to advance distally, distal blade (194) simultaneously severs the clamped tissue layers, resulting in separated upper layer portions being apposed with respective separated lower layer portions. In some versions, this results in a blood vessel being cut in a direction that is generally transverse to the length of the blood vessel. It should be understood that the presence of flanges (192, 196) immediately above and below jaws (182, 184), respectively, may help keep jaws (182, 184) in a closed and tightly clamping position. In particular, flanges (192, 196) may help maintain a significantly compressive force between jaws (182, 184). With severed tissue layer portions being compressed between jaws (182, 184), electrode surfaces (186, 187) are activated with bipolar RF energy by the surgeon providing a corresponding command input through controller (30) (e.g., through user input assembly (32) or footswitches (38), etc.). In some versions, electrodes (186, 187) are selectively coupled with power source (102) such that electrode surface (186, 187) of jaws (182, 184) are activated with a common first polarity while firing beam (190) is activated at a second polarity that is opposite to the first polarity. Thus, a bipolar RF current flows between firing beam (190) and electrode surfaces (186, 187) of jaws (182, 184), through the compressed regions of severed tissue layer portions. In some other versions, electrode surface (186) has one polarity while electrode surface (187) and firing beam (190) both have the other polarity. In either version (among at least some others), bipolar RF energy delivered by power source (102) ultimately thermally welds the tissue layer portions on one side of firing beam (190) together and the tissue layer portions on the other side of firing beam (190) together.

In certain circumstances, the heat generated by activated electrode surfaces (186, 187) can denature the collagen within the tissue layer portions and, in cooperation with clamping pressure provided by jaws (182, 184), the denatured collagen can form a seal within the tissue layer portions. Thus, the severed ends of the natural lumen defining anatomical structure are hemostatically sealed shut, such that the severed ends will not leak bodily fluids. In some versions, electrode surface (186, 187) may be activated with bipolar RF energy before firing beam (190) even begins to translate distally and thus before the tissue is even severed. Other suitable ways in which instrument (100) may be operable and operated will be apparent to those of ordinary skill in the art in view of the teachings herein.

Figure 14:
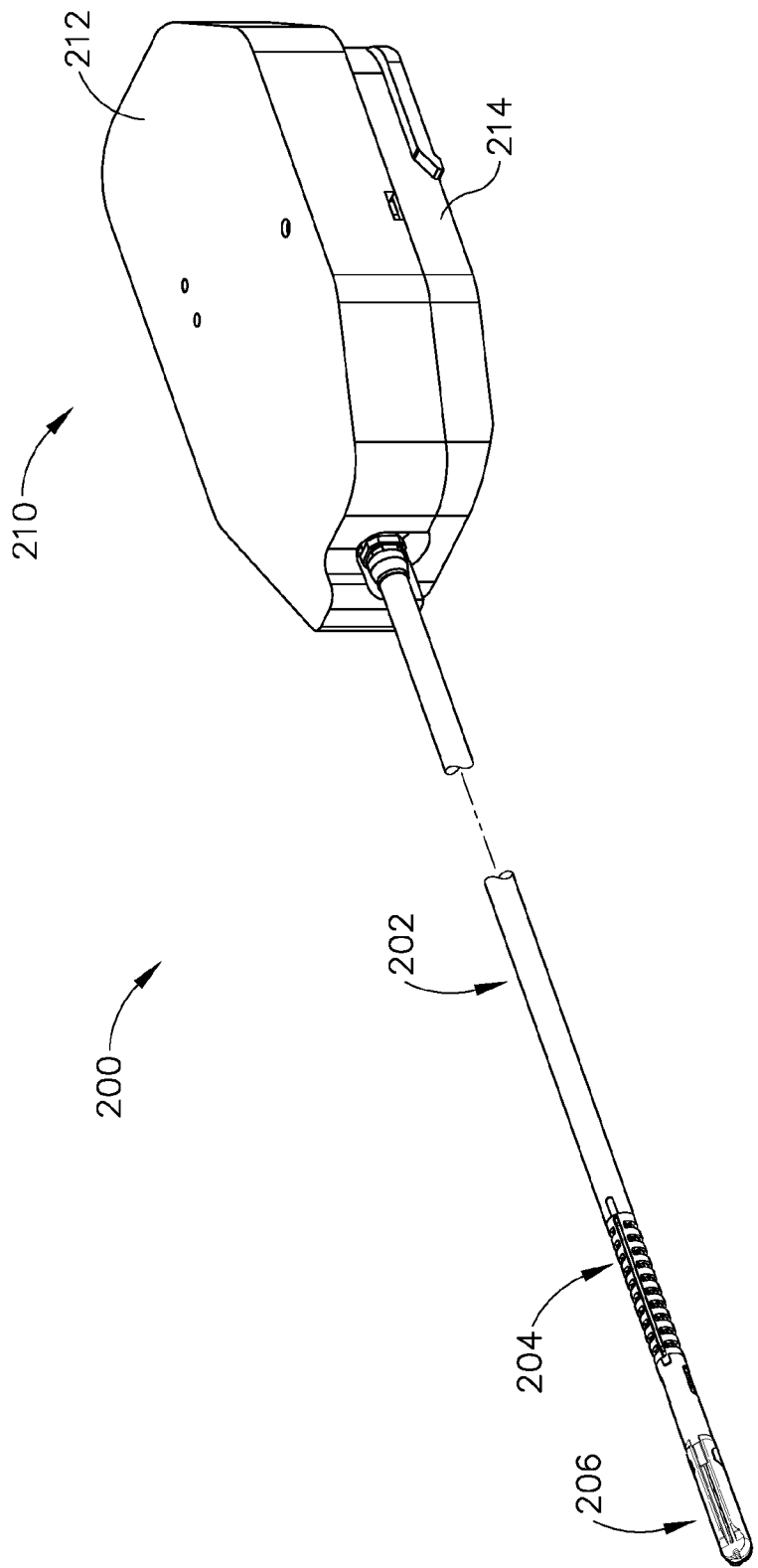
FIG. 14 depicts a perspective view of another exemplary surgical instrument suitable for incorporation with the system of FIG. 1.

III. Exemplary Alternative Electrosurgical Instrument with a Removable Shaft Assembly FIG. 14 shows an exemplary alternative electrosurgical instrument (200). Instrument (200) of this example is substantially similar to instrument (100) described above in that instrument (200) has a shaft assembly (202), an articulation section (204), and an end effector (206) that are substantially identical to shaft assembly (160), articulation section (170), and end effector (180) described above. Instrument (200) of this example is also operable to couple with a dock (72) of robotic arm cart (40) via an interface assembly (210). However, interface assembly (210) of this example is different from interface assembly (110) described above. In some instances, it may be economically desirable to provide a shaft assembly (202) that is removable from interface assembly (210). For example, shaft assembly (202) may be removed from interface assembly (210) after a surgical procedure such that shaft assembly (202) may be disposed of, while interface assembly (210) may be sterilized and reused in another surgical procedure. Accordingly, shaft assembly (202) and interface assembly (210) include coupling features to allow shaft assembly (202) to be removably coupled with interface assembly (210) by inserting shaft assembly (202) distally through the proximal end of interface assembly (210). The examples below include several merely illustrative versions of coupling features that may be readily introduced to an instrument (200).

A. Exemplary Shaft Assembly Coupling Features

Figure 15:
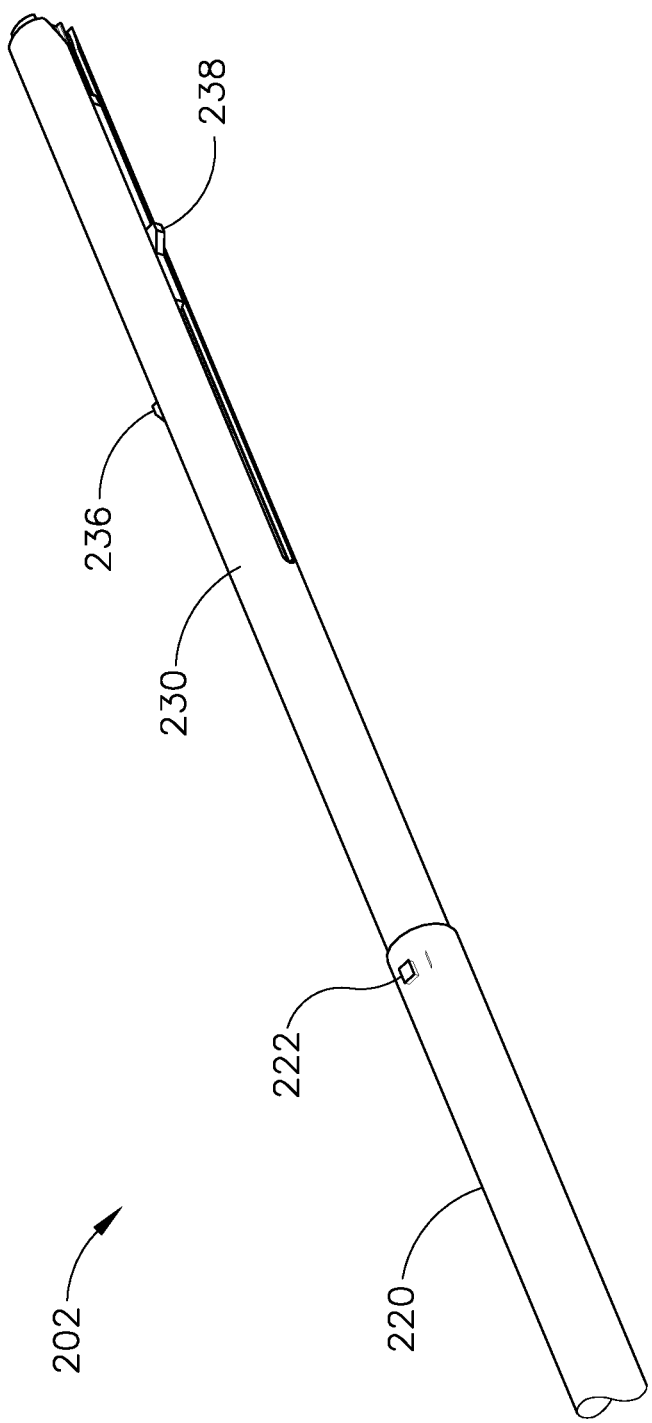
FIG. 15 depicts a partial perspective view of a shaft assembly of the surgical instrument of FIG. 14.

FIGS. 15-17 show shaft assembly (202) in greater detail. Shaft assembly (202) comprises an outer shaft (220), an inner shaft (230), and a plurality of coupling features (222, 232, 236, 238) to removably couple shaft assembly (202) with interface assembly (210). Outer shaft (220) comprises a coupling feature (222) extending outwardly from an outer surface of the proximal end of outer shaft (220). The distal end of outer shaft (220) is coupled with articulation section (204) and end effector (206). Accordingly, coupling feature (222) engages interface assembly (210) such that interface assembly (210) is operable to rotate coupling feature (222) and outer shaft (220) to thereby rotate outer shaft (220), articulation section (204), and end effector (206) relative to interface assembly (210).

Inner shaft (230) is coaxially and slidably disposed in outer shaft (220); and extends proximally from outer shaft (220). Inner shaft (230) comprises a coupling feature (232) extending outwardly from an outer surface of a proximal portion of inner shaft (230), as shown in FIG. 17. Coupling feature (232) is proximal to coupling feature (222) of outer shaft (220). The distal end of inner shaft (230) is coupled with firing beam (190). Accordingly, coupling feature (232) engages interface assembly (210) such that interface assembly (210) is operable to translate coupling feature (232) and inner shaft (230) relative to outer shaft (220) to thereby translate firing beam (190). Each side of inner shaft (230) further comprises a channel (234) extending distally from the proximal end of inner shaft (230), as shown in FIG. 17. Coupling features (236, 238) extend outwardly from inner shaft (230) through channels (234) such that coupling features (236, 238) may translate within channels (234). FIG. 16 shows that coupling feature (236) is distal to coupling feature (238). Each coupling feature (236, 238) is coupled with an articulation beam (174, 176) extending within inner shaft (230). Accordingly, each coupling feature (236, 238) engages interface assembly (210) such that interface assembly (210) is operable to translate coupling features (236, 238) to thereby opposingly translate articulation beams (174, 176) and deflect end effector (206) from the longitudinal axis of shaft assembly (202). Although four coupling features (222, 232, 236, 238) are shown, any other suitable number of coupling features (222, 232, 236, 238) may be used.

B. Exemplary Interface Assembly Coupling Features

Figure 18A:
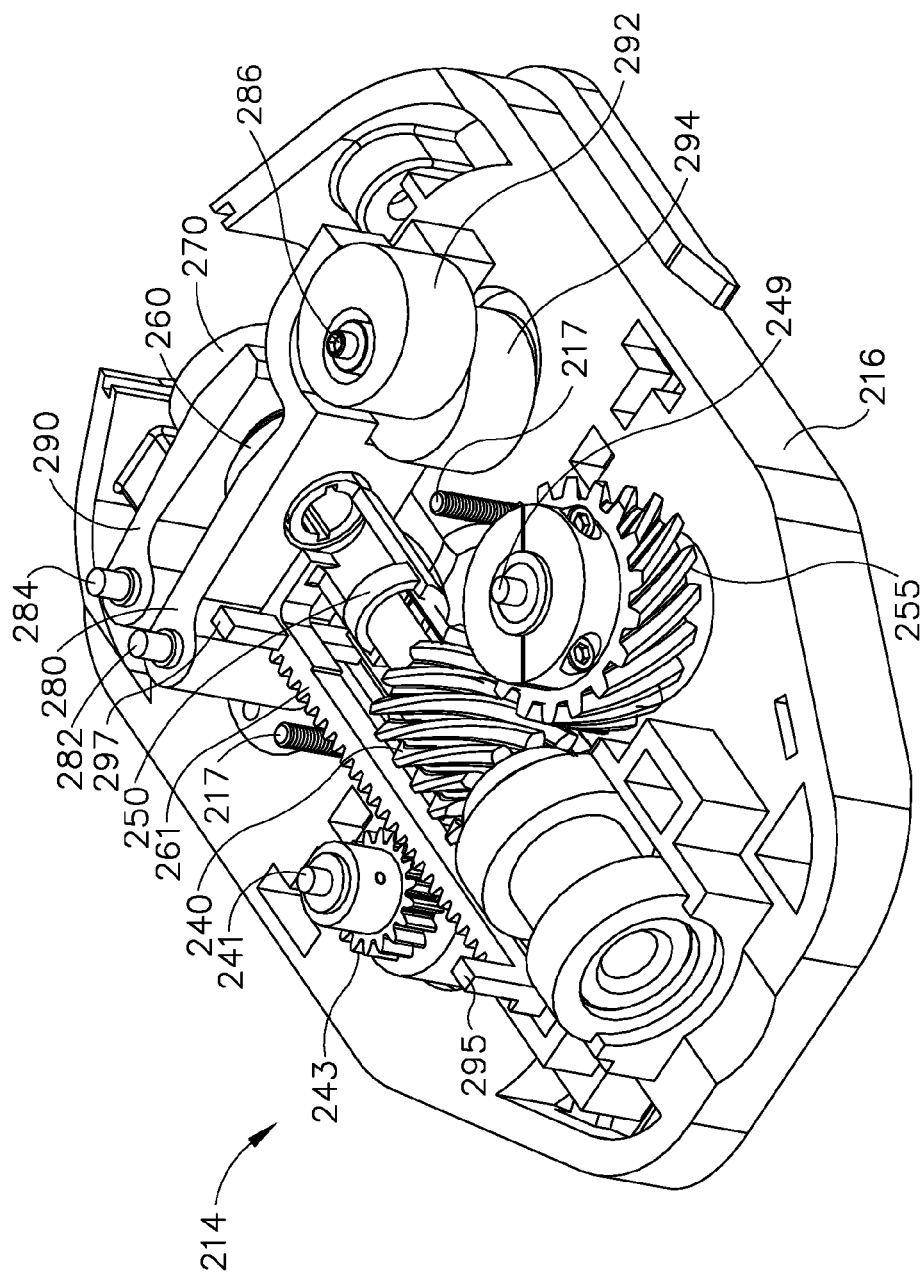
FIG. 18A depicts a partial perspective view of an interface assembly of the surgical instrument of FIG. 14 with a cover removed.
Figure 18B:
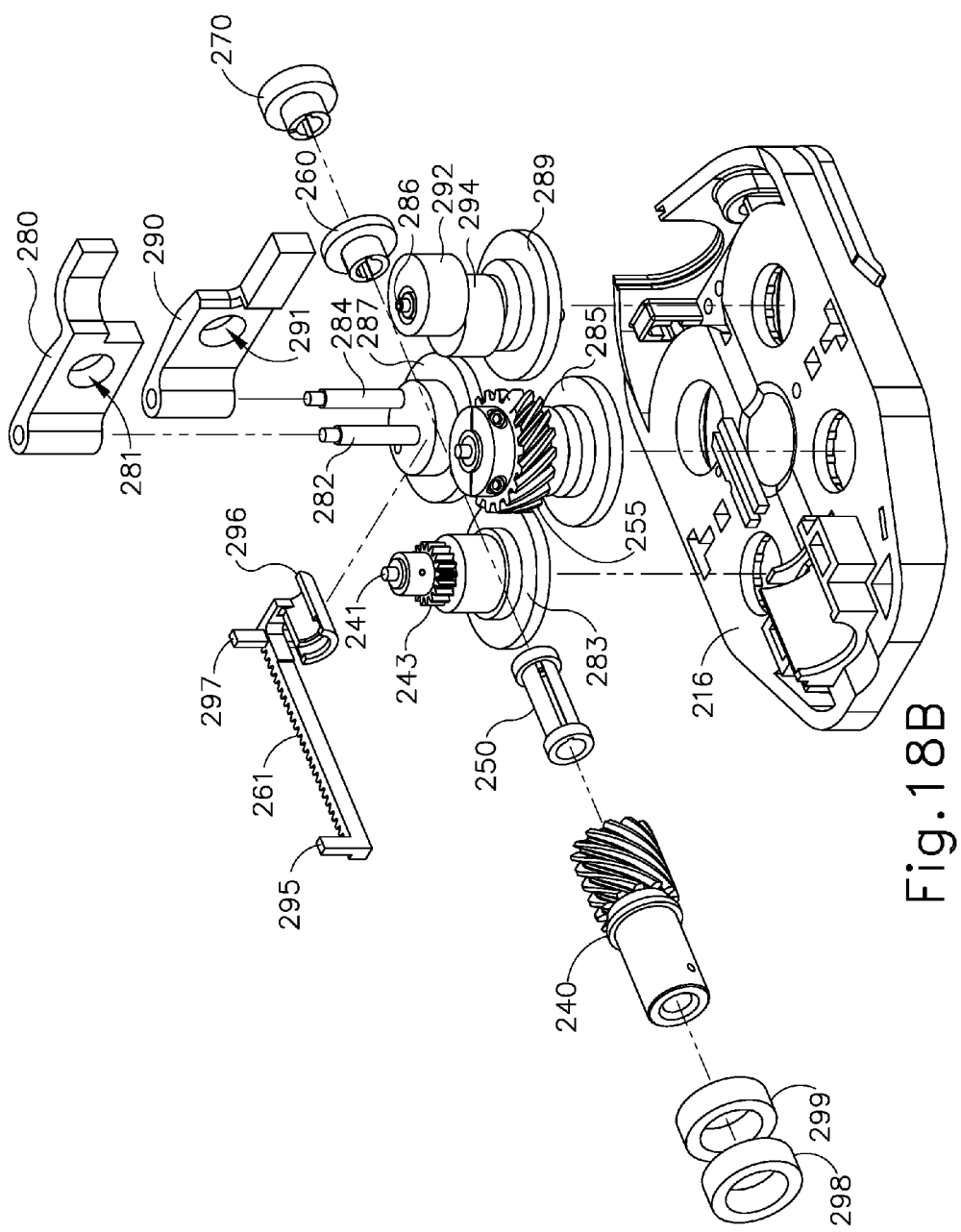
FIG. 18B depicts an exploded view of the interface assembly of FIG. 18A.
Figure 19:
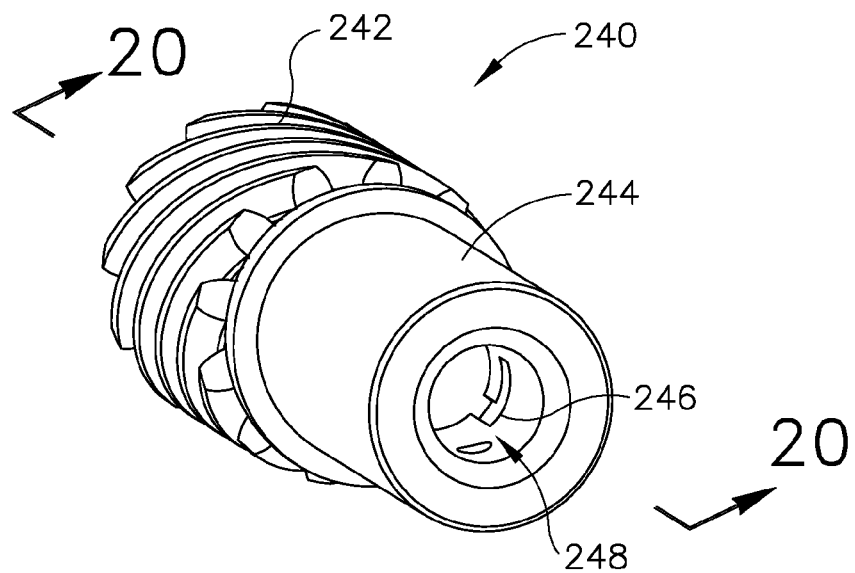
FIG. 19 depicts a perspective view of a helical gear of the interface assembly of FIG. 18A.
Figure 20:
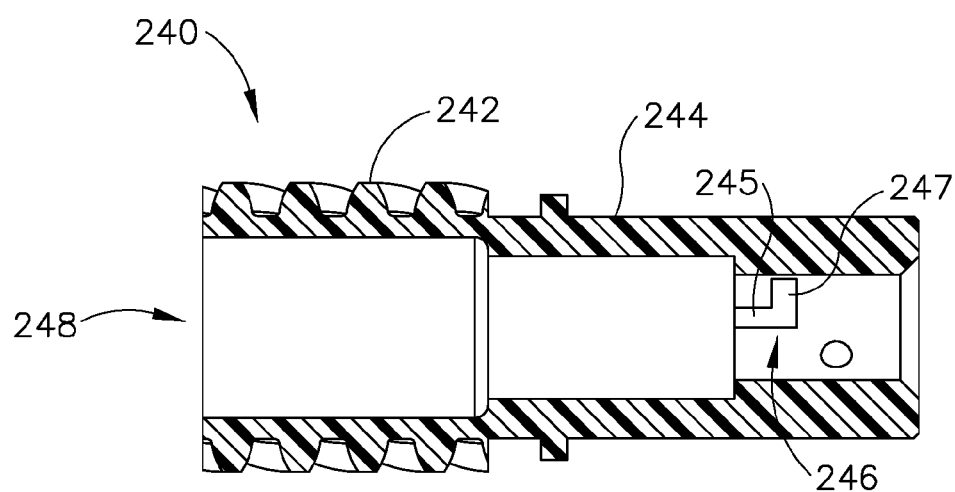
FIG. 20 depicts a cross sectional view of the helical gear of FIG. 19 taken along the line 20-20 of FIG. 19.
Figure 21:
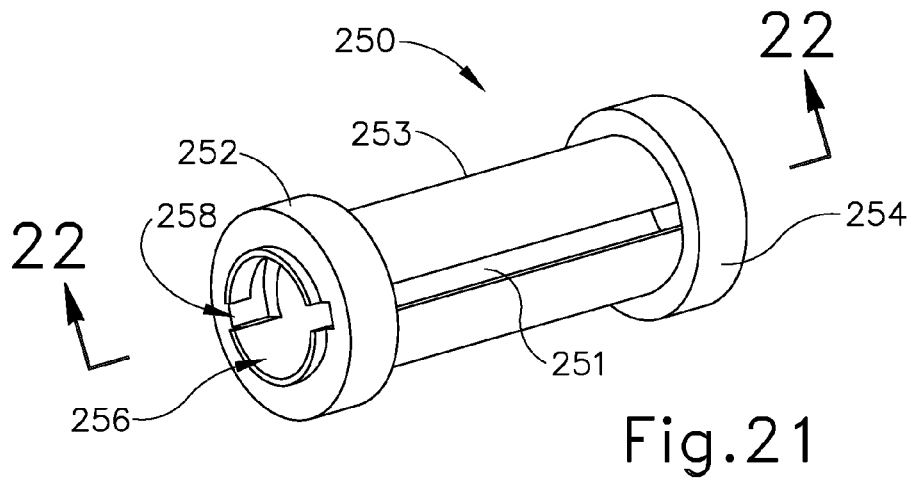
FIG. 21 depicts a perspective view of a first tubular member of the interface assembly of FIG. 18A.

FIGS. 18A and 18B show a base (214) of interface assembly (210) that is removably couplable with shaft assembly (202). Base (214) of interface assembly (210) comprises a helical gear (240), a first tubular member (250), a second tubular member (260), and a third tubular member (270) on mounting plate (216) that are configured to receive shaft assembly (202). Helical gear (240) comprises teeth (242) that mesh with complementary teeth of a second helical gear (255) on drive shaft (249). When drive shaft (249) is actuated, helical gear (255) rotates to thereby rotate helical gear (240). Helical gear (240) defines an opening (248) extending through helical gear (240) to receive shaft assembly (202), as shown in FIGS. 19 and 20. Opening (248) comprises a slot (246). Slot (246) comprises a recess (245) extending distally within opening (248) and a recess (247) extending transversely from recess (245) within opening (248). Slot (246) is thereby configured as a bayonet fitting and is sized to receive coupling feature (222) of outer shaft (220). Outer shaft (220) may be inserted distally through helical gear (240) such that coupling feature (222) is inserted distally within recess (245) of slot (246) until coupling feature (222) aligns with recess (247) of slot (246). Outer shaft (220) may then be rotated such that coupling feature (222) rotates within recess (247) to lock the longitudinal position of outer shaft (220) relative to helical gear (240). Accordingly, when helical gear (240) is rotated by second helical gear (255), helical gear (240) rotates outer shaft (220) to thereby rotate shaft assembly (202).

Figure 22:
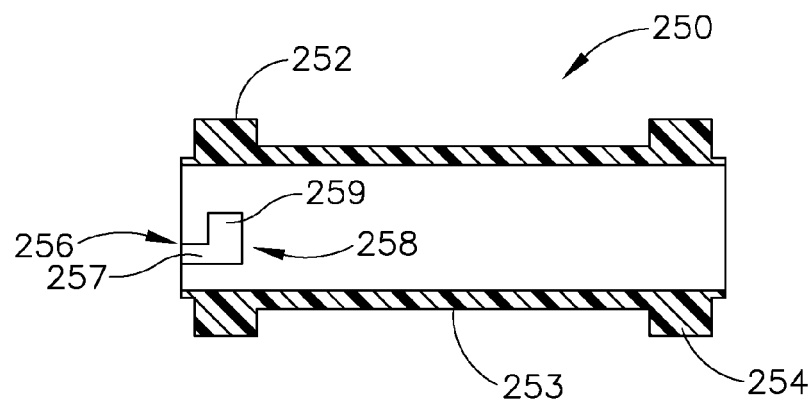
FIG. 22 depicts a cross sectional view of the first tubular member of FIG. 21 taken along the line 22-22 of FIG. 21.
Figure 23:
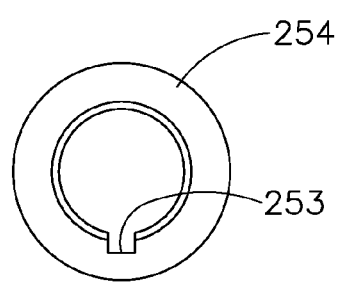
FIG. 23 depicts a rear view of the first tubular member of FIG. 21.
Figure 24:
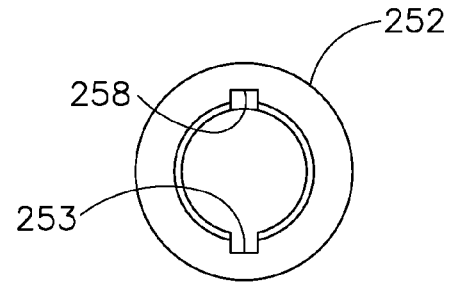
FIG. 24 depicts a front view of the first tubular member of FIG. 21.
Figure 25:
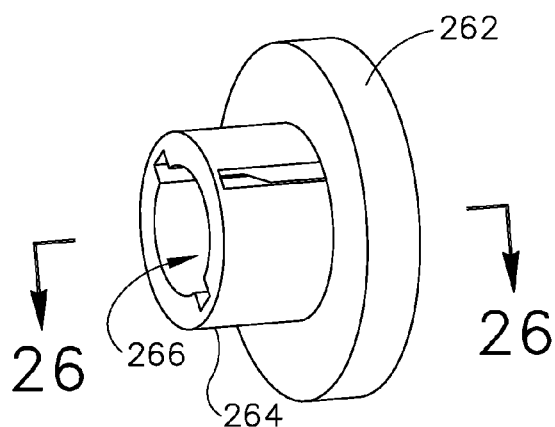
FIG. 25 depicts a perspective view of a second tubular member of the interface assembly of FIG. 18A.

First tubular member (250) is proximal to helical gear (240) and is coupled with rack (261) of interface assembly (210), as shown in FIGS. 18A and 18B. Rack (261) comprises a semi-circular bracket (296) extending inwardly from rack (261). Bracket (296) is sized to correspond to first tubular member (250) such that first tubular member (250) rests within bracket (296). Bracket (296) further comprises a recess to receive distal portion (252) of first tubular member (250), which has a larger outer diameter than central portion (251) of first tubular member (250). First tubular member (250) therefore translates with bracket (296) of rack (261). Rack (261) comprises a longitudinal row of teeth that mesh with teeth on gear (243) on drive shaft (241). Drive shaft (241) is actuated to rotate gear (243). The rotation of gear (243) translates rack (261) to thereby translate first tubular member (250). As shown in FIGS. 21-24, first tubular member (250) defines an opening (256) to receive shaft assembly (202). A first recess (253) within opening (256) extends entirely through opening (256). This allows coupling feature (222) of outer shaft (220) to slide through opening (253) of channel (256) as outer shaft (220) is inserted distally through interface assembly (210) until coupling feature (222) engages helical gear (240). A slot (258) is also provided within opening (256) to receive coupling feature (232) as a bayonet fitting. As shown in FIG. 22, slot (258) comprises a recess (257) extending distally through a portion of first tubular member (250) from the proximal end of first tubular member (250). Recess (259) extends transversely from recess (257). Slot (258) is positioned on the opposing side of opening (256) from recess (253) to receive coupling feature (232) of inner shaft (230). Inner shaft (230) may be inserted distally through first tubular member (250) such that coupling feature (232) is inserted distally within recess (257) of slot (258) until coupling feature (232) aligns with recess (259) of slot (258). Inner shaft (230) may then be rotated such that coupling feature (232) rotates within recess (259) to lock the longitudinal position of inner shaft (230) relative to first tubular member (250). Accordingly, when first tubular member (250) is translated by rack (261), first tubular member (250) translates inner shaft (230) to thereby translate firing beam (190).

Figure 26:
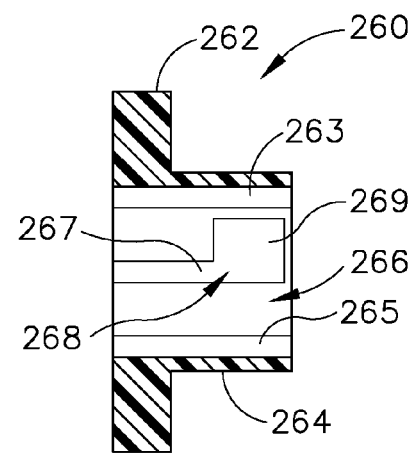
FIG. 26 depicts a cross sectional view of the second tubular member of FIG. 25 taken along the line 26-26 of FIG. 25.
Figure 27:
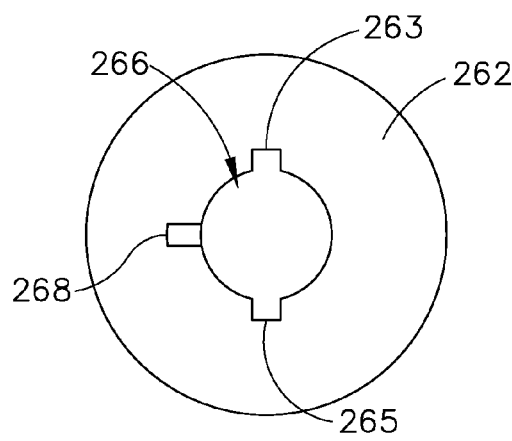
FIG. 27 depicts a rear view of the second tubular member of FIG. 25.
Figure 28:
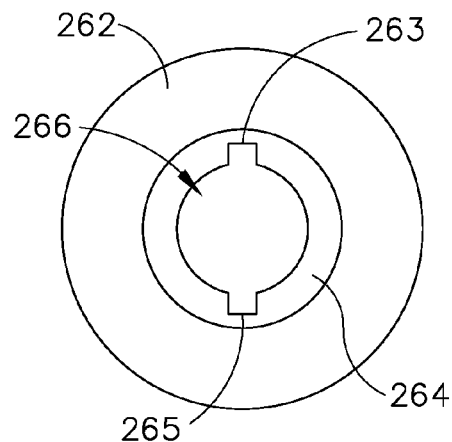
FIG. 28 depicts a front view of the second tubular member of FIG. 25.
Figure 29:
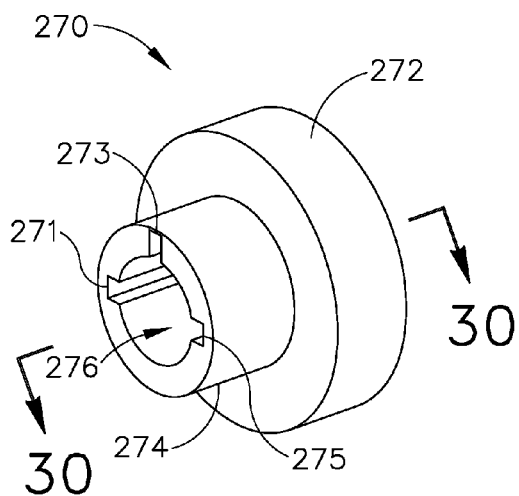
FIG. 29 depicts a perspective view of a third tubular member of the interface assembly of FIG. 18A.

Second tubular member (260) is proximal to first tubular member (250) and is coupled with first lever arm (280) of interface assembly (210), as shown in FIGS. 18A and 18B. First lever arm (280) is coupled with Idle shaft (282) and is pivotable relative to Idle shaft (282). The opposing end of first lever arm (280) is positioned against an eccentric cam (292) on drive shaft (286). When drive shaft (286) is actuated, eccentric cam (292) rotates to thereby translate first lever arm (280) and second tubular member (260). As shown in FIGS. 25-28, second tubular member (260) comprises a distal portion (264), a proximal portion (262), and an opening (266) extending through second tubular member (260) to receive shaft assembly (202). Distal portion (264) of second tubular member (260) has a larger outer diameter than proximal portion (262) of second tubular member (260). This allows distal portion (264) of second tubular member (260) to be inserted within an opening of first lever arm (280) until proximal portion (262) of second tubular member (260) engages the proximal wall of first lever arm (280). A friction fit may be provided between distal portion (264) and the opening of first lever arm (280) to longitudinally fix second tubular member (260) relative to first lever arm (280). A first recess (263) and a second recess (265) extend entirely through opening (266). This allows coupling feature (222) of outer shaft (220) and coupling feature (232) of inner shaft (230) to slide through recesses (263, 265) of opening (266) as shaft assembly (202) is inserted distally through interface assembly (210). A slot (268) is also provided within opening (266) to receive coupling feature (236) as a bayonet fitting. As shown in FIG. 26, slot (268) comprises a recess (267) extending distally through a portion of second tubular member (260) from the proximal end of second tubular member (260). Recess (269) extends transversely from recess (267). Slot (268) is positioned between recesses (263, 265) to receive coupling feature (236) of inner shaft (230). Inner shaft (230) may be inserted distally through second tubular member (260) such that coupling feature (236) is inserted distally within recess (267) of slot (268) until coupling feature (236) aligns with recess (269) of slot (268). Inner shaft (230) may then be rotated such that coupling feature (236) rotates within recess (269) to lock the longitudinal position of inner shaft (230) relative to second tubular member (260). Accordingly, when second tubular member (260) is translated by first lever arm (280), second tubular member (260) translates one of articulation beams (174, 176).

Figure 30:
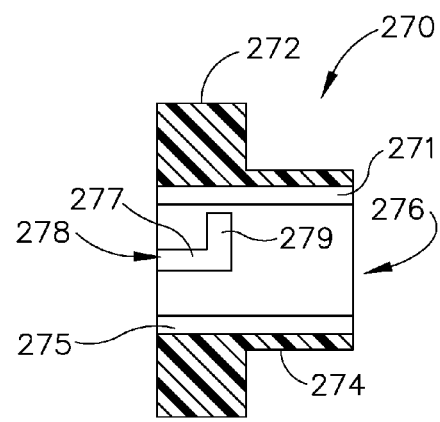
FIG. 30 depicts a cross sectional view of the third tubular member of FIG. 29 taken along the line 30-30 of FIG. 29.
Figure 31:
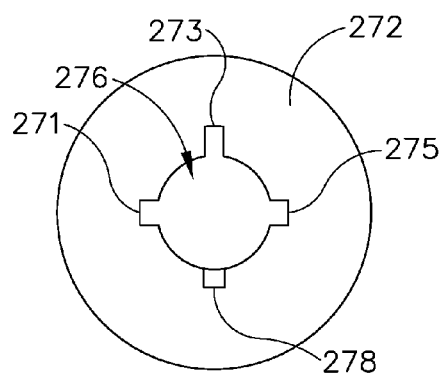
FIG. 31 depicts a rear view of the third tubular member of FIG. 29.
Figure 32:
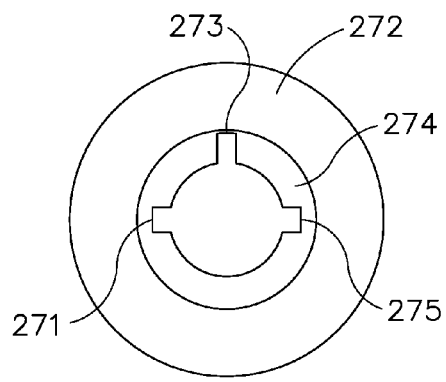
FIG. 32 depicts a front view of the third tubular member of FIG. 29.

Third tubular member (270) is proximal to second tubular member (260) and is coupled with second lever arm (290) of interface assembly (210), as shown in FIGS. 18A and 18B. Second lever arm (290) is coupled with Idle shaft (284) and is pivotable relative to Idle shaft (284). The opposing end of second lever arm (290) is positioned against an eccentric cam (294) on drive shaft (286). When drive shaft (286) is actuated, eccentric cam (294) rotates to thereby translate second lever arm (290) and third tubular member (270). Eccentric cams (292, 294) are offset to opposingly translate lever arms (280, 290). As shown in FIGS. 29-32, third tubular member (270) comprises a distal portion (274), a proximal portion (272), and an opening (276) extending through third tubular member (270) to receive shaft assembly (202). Distal portion (274) of third tubular member (270) has a larger outer diameter than proximal portion (272) of third tubular member (270). This allows distal portion (274) of third tubular member (270) to be inserted within an opening of second lever arm (290) until proximal portion (272) of third tubular member (270) engages the proximal wall of second lever arm (290). A friction fit may be provided between distal portion (274) and the opening of second lever arm (290) to longitudinally fix third tubular member (270) relative to second lever arm (290). A first recess (271), a second recess (273), and a third recess (275) extend entirely through opening (276). This allows coupling features (222, 232, 236) of outer shaft (220) and inner shaft (230) to slide through recesses (271, 273, 275) of opening (266) as shaft assembly (202) is inserted distally through interface assembly (210). A slot (278) is also provided within opening (276) to receive coupling feature (238) as a bayonet fitting. As shown in FIG. 30, slot (278) comprises a recess (277) extending distally through a portion of third tubular member (270) from the proximal end of third tubular member (270). Recess (279) extends transversely from recess (277). Slot (278) is positioned between recesses (271, 275) to receive coupling feature (238) of inner shaft (230). Inner shaft (230) may be inserted distally through third tubular member (270) such that coupling feature (238) is inserted distally within recess (277) of slot (278) until coupling feature (238) aligns with recess (279) of slot (278). Inner shaft (230) may then be rotated such that coupling feature (238) rotates within recess (279) to lock the longitudinal position of inner shaft (230) relative to third tubular member (270). Accordingly, when third tubular member (270) is translated by second lever arm (290), third tubular member (270) translates the other one of articulation beams (174, 176) as second tubular member (260).

Figure 33:
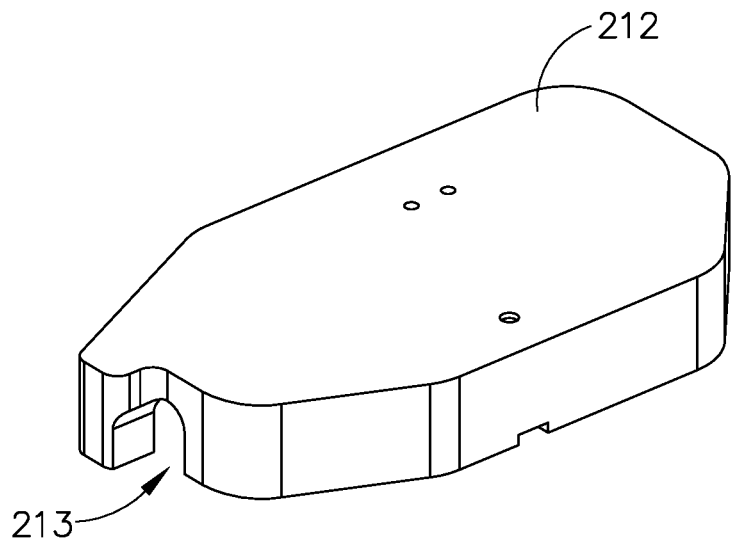
FIG. 33 depicts a top perspective view of a cover of the interface assembly of FIG. 18A.
Figure 34:
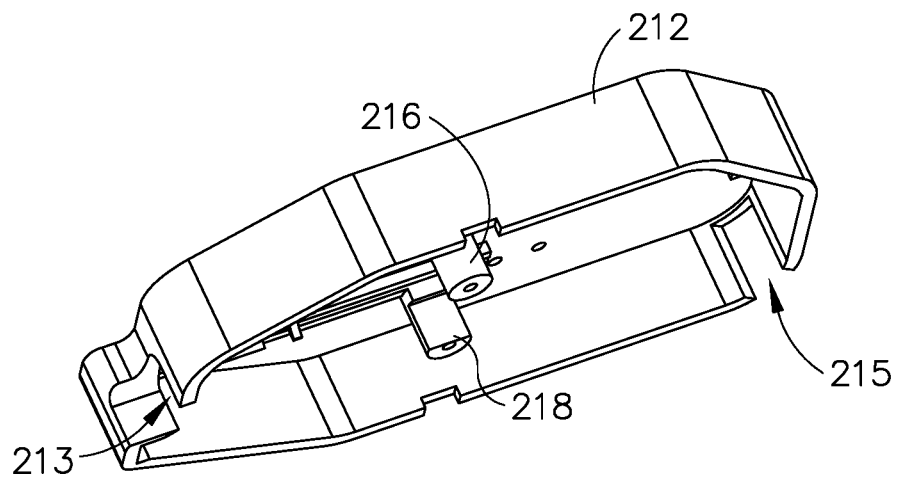
FIG. 34 depicts a bottom perspective view of the cover of FIG. 33.
Figure 35:
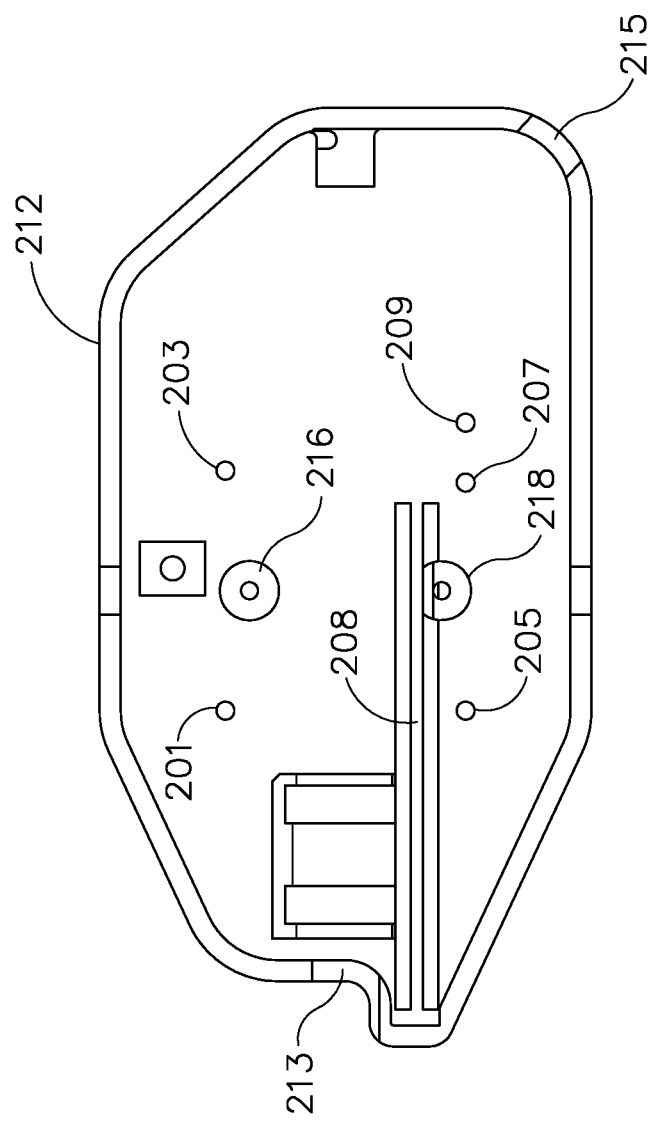
FIG. 35 depicts a bottom plan view of the cover of FIG. 33.

FIGS. 33-35 show a housing (212) for coupling with base (214) of interface assembly (210). Housing (212) is similar to housing (112), except that housing (212) comprises alignment features (201, 203, 205, 207, 209). Alignment features (201, 203, 205, 207, 209) are recesses within a top surface of housing (212) and are positioned to correspond to drive shafts (241, 249, 282, 284, 286). A portion of drive shafts (241, 249, 282, 284, 286) extend within alignment features (201, 203, 205, 207, 209) such that drive shafts (241, 249, 282, 284, 286) are able to rotate within alignment features (201, 203, 205, 207, 209). This fixes the lateral and longitudinal position of housing (212) relative to base (214) of interface assembly (210). Housing (212) further comprises a channel (208) that is sized to receive to protrusions (295, 297) extending upwardly from rack (261) such that protrusions (295, 297) are configured to translate within channel (208) of housing (212). Opening (213) of housing (212) is configured such that shaft assembly (202) extends through opening (213) of housing (212). Opening (215) of housing (212) is configured such that a cable (118) may extend through opening (215) of housing (212). Housing (212) may be positioned over base (214) and coupled to base (214) after shaft assembly (202) is inserted within and coupled to base (214). Screws (217) of base (214) may be threaded into recesses (216, 218) of housing (212) to secure housing (212) to base (214). Alternatively, housing (212) and/or base (214) may comprise tabs such that housing (212) may be snap fit onto base (214). Other suitable methods for coupling housing (212) to base (214) will be apparent to one with ordinary skill in the art in view of the teachings herein.

C. Exemplary Assembly

Figure 36A:
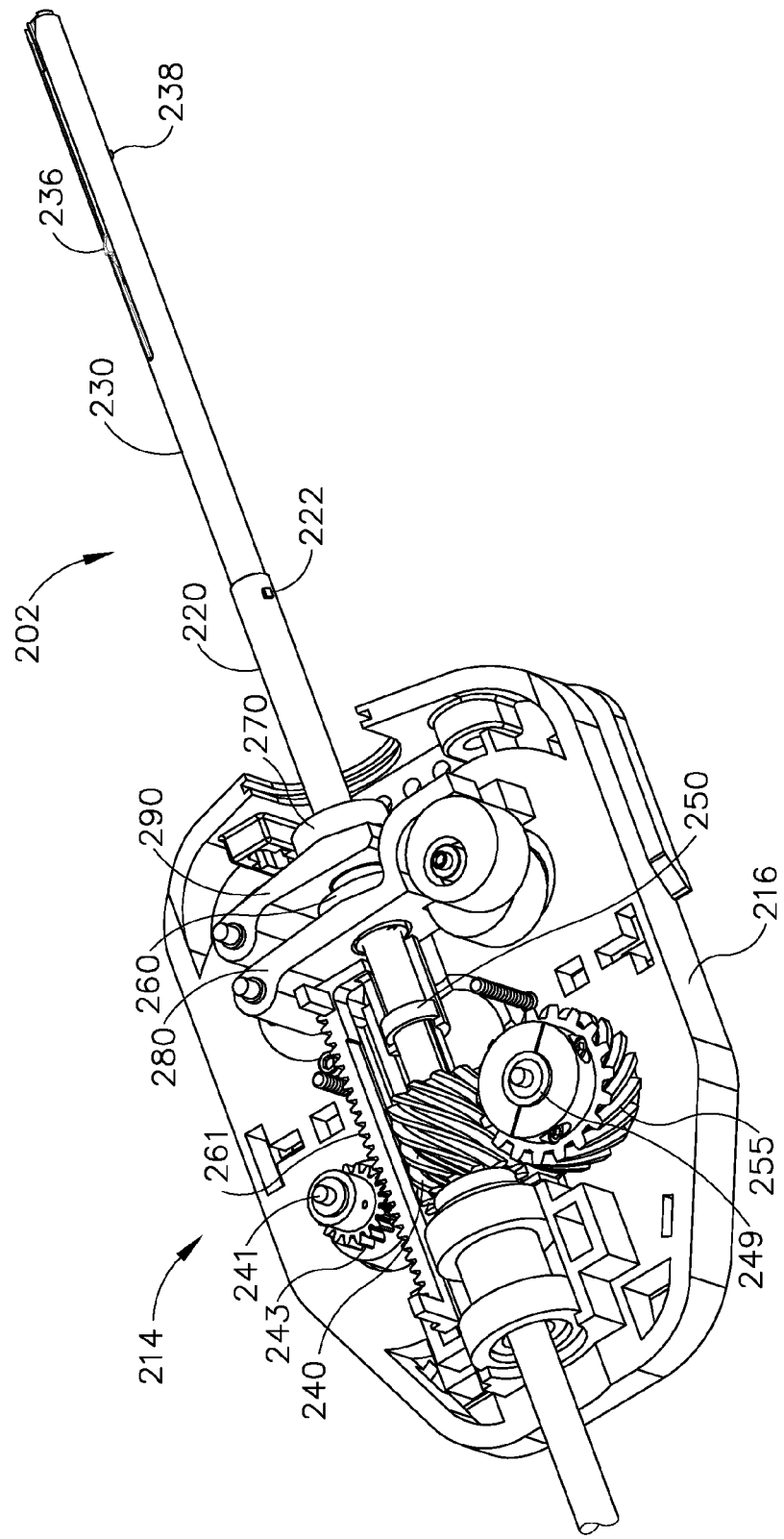
FIG. 36A depicts a partial perspective view of the instrument of FIG. 14, showing the shaft assembly being inserted within the interface assembly with the cover removed.
Figure 36B:
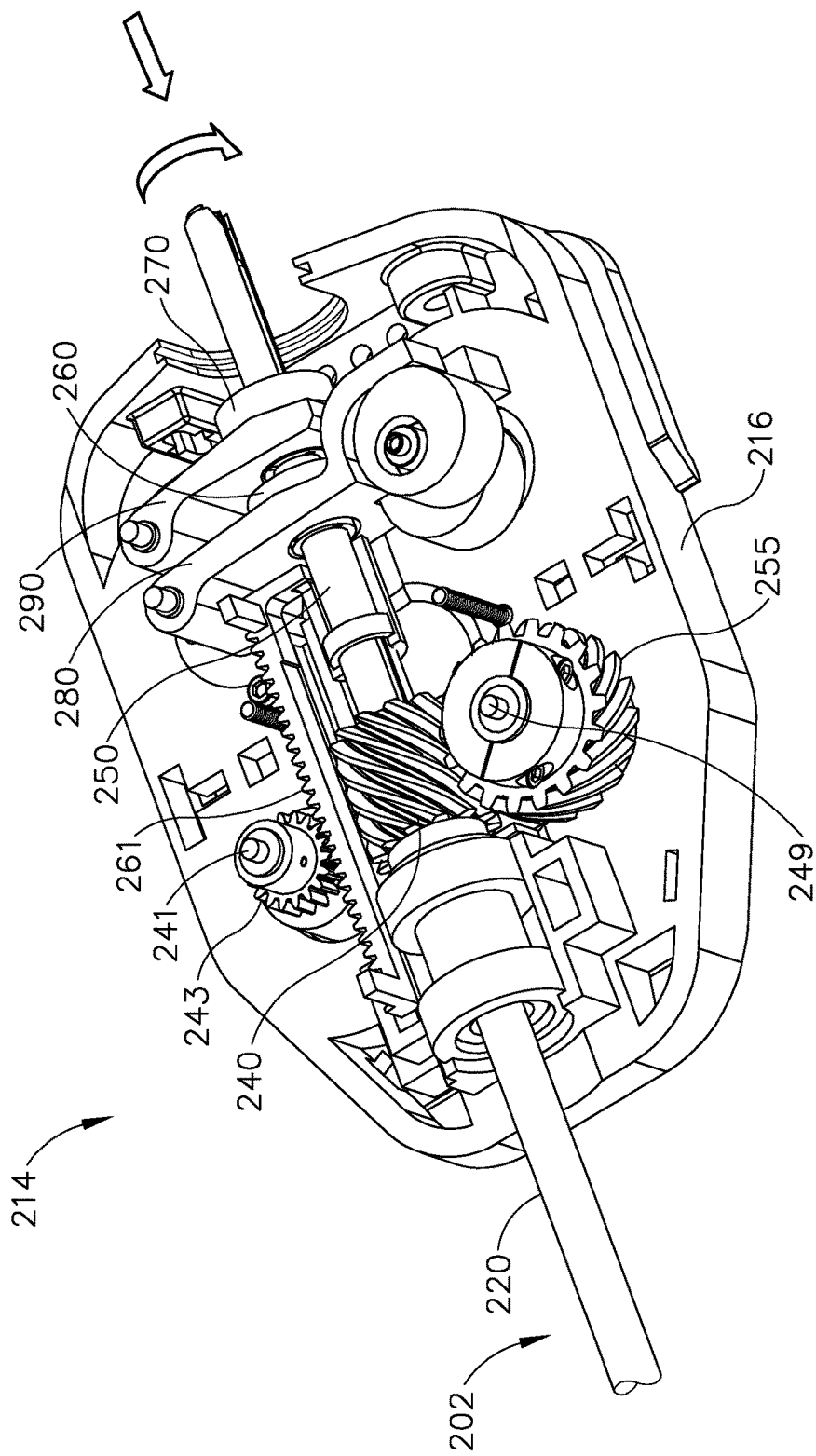
FIG. 36B depicts a partial perspective view of the instrument of FIG. 14, showing the shaft assembly coupled with the interface assembly with the cover removed.
Figure 36C:
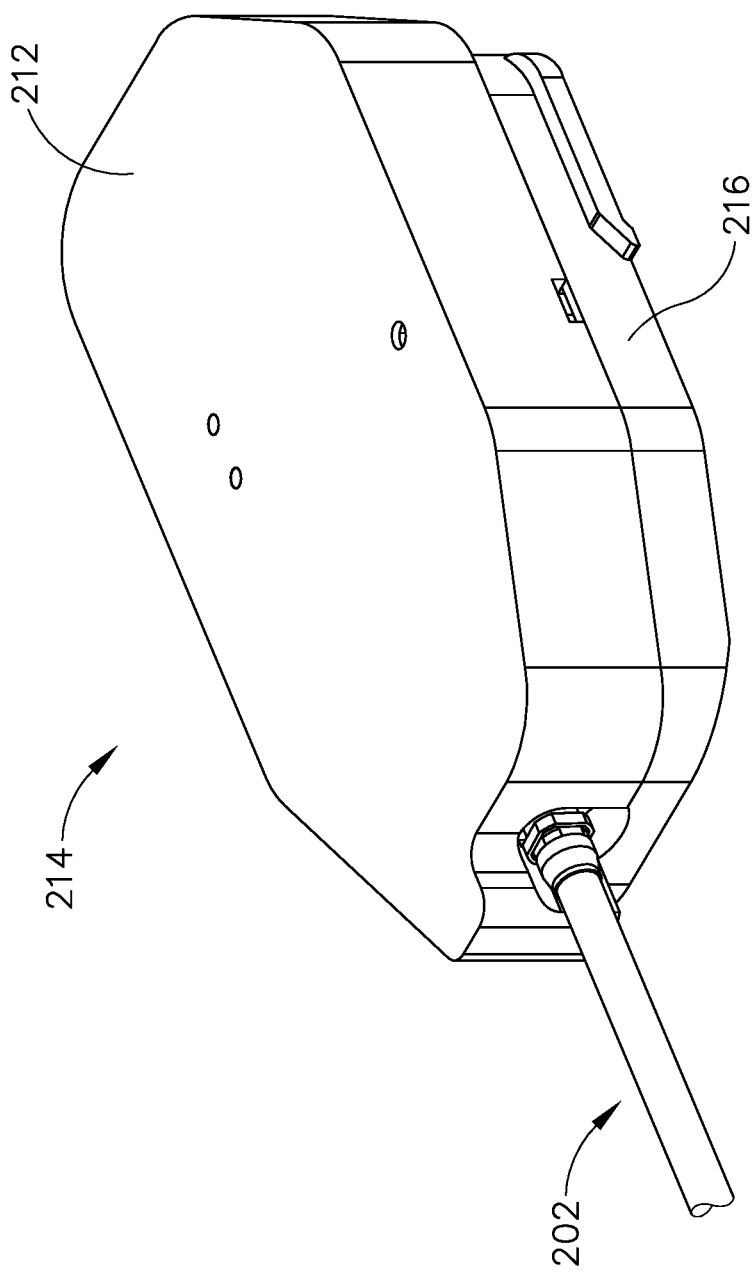
FIG. 36C depicts a partial perspective view of the instrument of FIG. 14, showing the cover coupled with the shaft assembly and the interface assembly.

FIGS. 36A-36C show an exemplary assembly of shaft assembly (202) within interface assembly (210). As shown in FIG. 36A, shaft assembly (202) may be inserted distally through a proximal end of interface assembly (210). Coupling features (222, 232, 236, 238) are aligned with corresponding slots (246, 258, 268, 278). Accordingly, coupling feature (222) of outer shaft (220) slides distally through recess (271) of third tubular member (270), recess (265) of second tubular member (260), and recess (253) of first tubular member (250) until coupling feature (222) enters slot (246) of helical gear (240). Coupling feature (222) then slides distally within recess (245) of slot (246) until coupling feature (222) aligns with transverse recess (247) of slot (246). Coupling feature (232) on the bottom surface of inner shaft (230) slides distally through recess (275) of third tubular member (270) and recess (263) of second tubular member (260) until coupling feature (232) enters slot (258) of first tubular member (250). Coupling feature (232) then slides distally within recess (257) of slot (258) until coupling feature (232) aligns with transverse recess (259) of slot (258). Coupling feature (238) of inner shaft (230) slides distally through recess (273) of third tubular member (270) and enters slot (268) of second tubular member (260). Coupling feature (236) then enters recess (267) of slot (258) until coupling feature (236) aligns with transverse recess (269) of slot (268). Coupling feature (238) of inner shaft (230) slides distally to enter recess (277) of slot (278) of third tubular member (270) until coupling feature (238) aligns with transverse recess (279) of slot (278). This longitudinally aligns shaft assembly (202) with interface assembly (210).

Shaft assembly (202) is then rotated within interface assembly (210) to lock the longitudinal position of shaft assembly (202) relative to interface assembly (210), as shown in FIG. 36B. For example, coupling feature (222) rotates within transverse recess (247) of slot (246), coupling feature (232) rotates within transverse recess (259) of slot (258), coupling feature (236) rotates within transverse recess (269) of slot (268), and coupling feature (238) rotates within transverse recess (279) of slot (278). Although shaft assembly (202) is shown as rotating clockwise in the present example to longitudinally lock shaft assembly (202) relative to interface assembly (210), slots (246, 258, 268, 278) may be configured such that shaft assembly (202) is rotated counterclockwise to lock the longitudinally position of shaft assembly (202). Once shaft assembly (202) is coupled with interface assembly (210), housing (212) is coupled with base (214) of interface assembly (210), as shown in FIG. 36C. Housing (212) is positioned over base (214) such that alignment features (201, 203, 205, 207, 209) of housing (212) are positioned over drive shafts (241, 249, 282, 284, 286) of base (214) and channel (208) is positioned over protrusions (295, 297) of rack (261). Housing (212) is then pressed downward toward base (214) such that a portion of drive shafts (241, 249, 282, 284, 286) enter alignment features (201, 203, 205, 207, 209) and protrusions (295, 297) enter channel (208). This fixes the longitudinal and lateral position of housing (212) relative to base (214).

After housing (212) is coupled with base (214) of interface assembly (210), instrument (200) may be operated. In an exemplary use, arm cart (40) is used to insert end effector (206) into a patient via a trocar. Articulation section (204) is substantially straight when end effector (206) and part of shaft assembly (202) are inserted through the trocar. Drive shaft (249) may be rotated through drive features in dock (72) that are coupled with corresponding disc (285), to position end effector (206) at a desired angular orientation relative to the tissue. Drive shaft (286) may then be rotated through a drive feature in dock (72) that is coupled with corresponding disc (289), to pivot or flex articulation section (204) of shaft assembly (202) in order to position end effector (206) at a desired position and orientation relative to an anatomical structure within the patient. Two layers of tissue of the anatomical structure are then captured between jaws (182, 184) by rotating drive shaft (241) through a drive feature in dock (72) that is coupled with corresponding disc (283) to advance firing beam (190) distally through a first range of motion. As noted above, flanges (192, 196) cammingly act to pivot jaw (182) toward jaw (184) when firing beam (190) is actuated distally by rotating drive shaft (241).

With tissue layers captured between jaws (182, 184) firing beam (190) continues to advance distally in response to continued rotation of drive shaft (241). As firing beam (190) continues to advance distally, distal blade (194) simultaneously severs the clamped tissue layers, resulting in separated upper layer portions being apposed with respective separated lower layer portions. With severed tissue layer portions being compressed between jaws (182, 184), electrode surfaces (186, 187) are activated with bipolar RF energy by the surgeon providing a corresponding command input through controller (30) (e.g., through user input assembly (32) or footswitches (38), etc.). Bipolar RF energy delivered by power source (102) ultimately thermally welds the tissue layer portions on one side of firing beam (190) together and the tissue layer portions on the other side of firing beam (190) together. Drive shaft (241) may then be actuated in the opposing direction to retract firing beam (190) and open jaws (182, 184) of end effector (206). Articulation section (204) may be again aligned with shaft assembly (202) by actuating drive shaft (286) and end effector (206) may be removed from the patient.

Housing (212) and shaft assembly (202) may then be decoupled from base (214) of interface assembly (210). For example, housing (212) is pulled upwardly from base (214). Shaft assembly (202) is rotated such that coupling features (222, 232, 236, 238) rotate out of corresponding transverse recesses (247, 259, 269, 270) of slots (246, 258, 268, 278). Shaft assembly (202) is then pulled proximally out of interface assembly (210). Shaft assembly (202) may then be discarded, while interface assembly (210) may be sterilized and reused in another surgical procedure.

D. Exemplary Retractable Shaft Assembly Coupling Features

Figure 37:
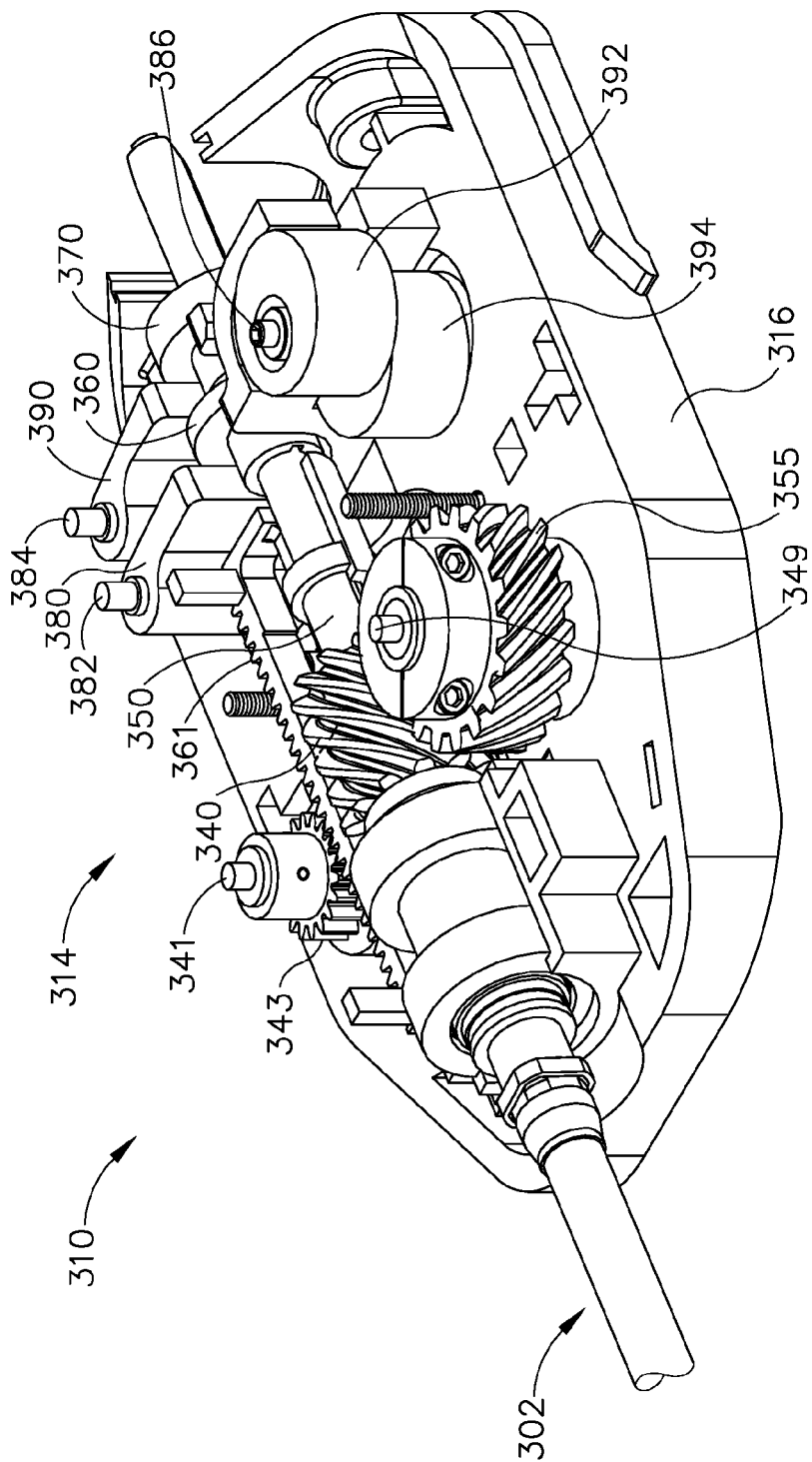
FIG. 37 depicts a partial perspective view of another exemplary surgical instrument suitable for incorporation with the system of FIG. 1, with a cover removed.
Figure 38:
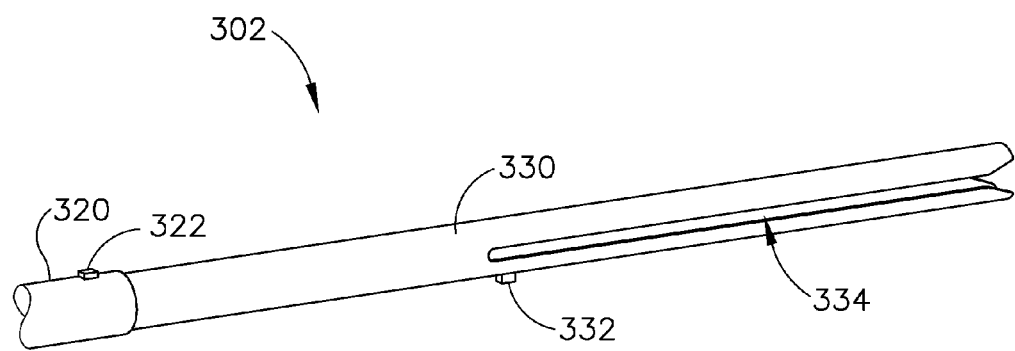
FIG. 38 depicts a partial perspective view of a proximal end of a shaft assembly of the instrument of FIG. 37.
Figure 41A:
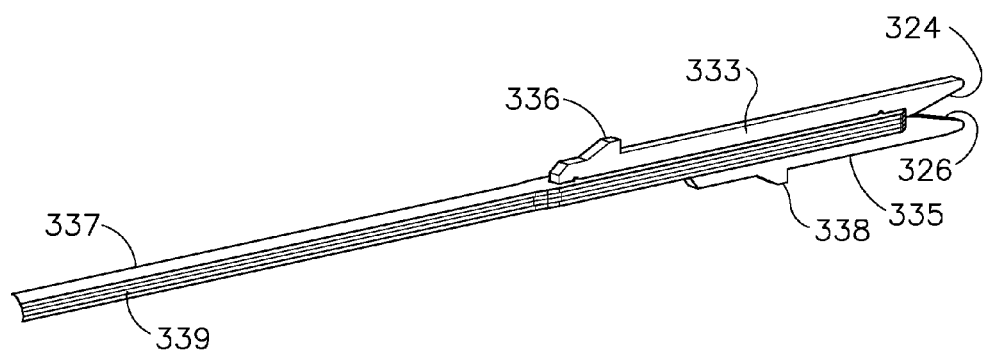
FIG. 41A depicts a partial perspective view of the proximal end of the shaft assembly of FIG. 38, with the plug removed and with the shaft cover omitted.

Shaft assembly (202) may be modified such that coupling features (222, 232, 236, 238) are retractable within shaft assembly (202). For example, FIG. 37 shows another exemplary shaft assembly (302) and base (314) of an interface assembly (310). Shaft assembly (302) is similar to shaft assembly (202), except that shaft assembly (302) comprises retractable coupling features (336, 338). As shown in FIG. 38, shaft assembly (302) comprises an outer shaft (320) with coupling feature (322) extending outwardly from outer shaft (320) and an inner shaft (330) extending proximally from outer shaft (320). Inner shaft (330) comprises a coupling feature (332) extending outwardly from inner shaft (330) and a channel (334) extending distally on each side of inner shaft (330) from the proximal end of inner shaft (330). Articulation beams (337, 338) extend through inner shaft (330) and are similar to articulation beams (174, 176). As shown in FIG. 41A, translating members (333, 335) are coupled to articulation beams (337, 339). Translating member (333) comprises coupling feature (336) extending outwardly from translating member (333) and translating member (335) comprises coupling feature (338) extending outwardly from translating member (335). Translating members (333, 335) are positioned within inner shaft (330) such that coupling features (336, 338) are configured to extend outward from channel (334) and translate through channel (334). The proximal ends of translating members (333, 335) include ramped surfaces (324, 326) to receive a plug (393).

Figure 39:
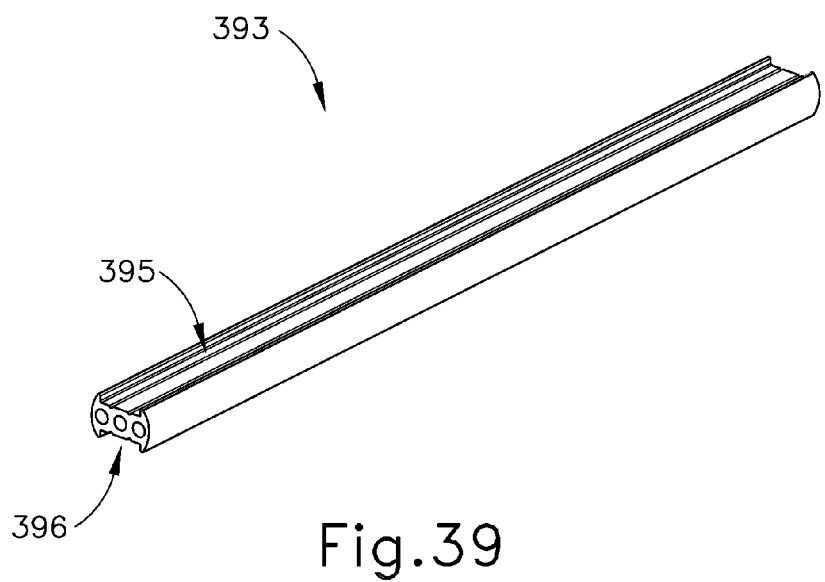
FIG. 39 depicts a perspective view of a plug for use with the shaft assembly of FIG. 38.
Figure 40A:
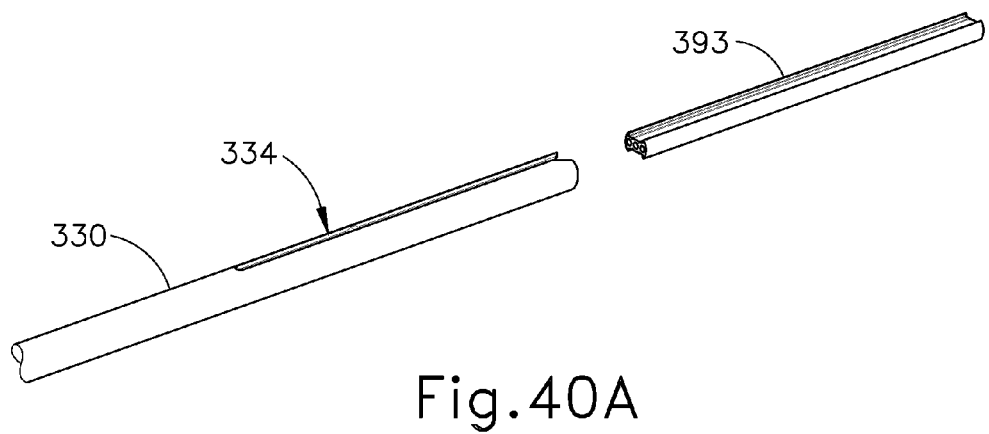
FIG. 40A depicts a partial perspective view of the plug of FIG. 39 being inserted within the shaft assembly of FIG. 38.
Figure 40B:
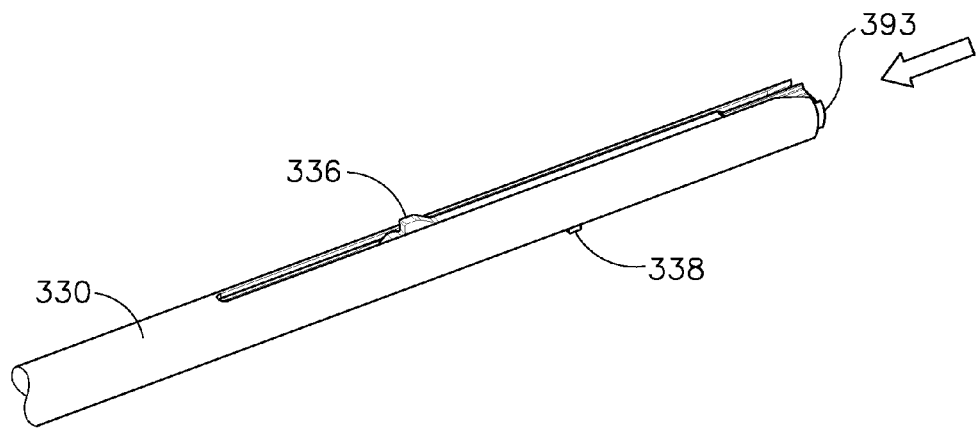
FIG. 40B depicts a partial perspective view of the plug of FIG. 39 coupled with the shaft assembly of FIG. 38.
Figure 41B:
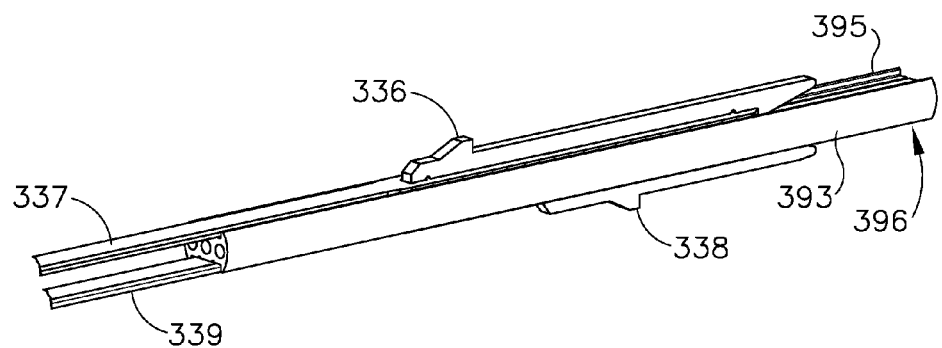
FIG. 41B depicts a partial perspective view of the proximal end of the shaft assembly of FIG. 38, with the plug inserted and with the shaft cover omitted.
Figure 42:
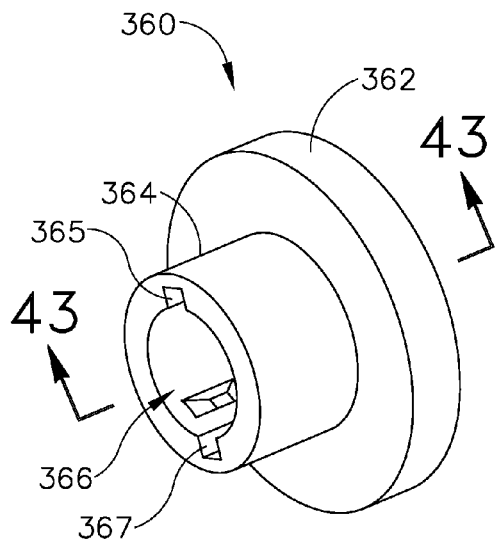
FIG. 42 depicts a perspective view of a second tubular member of an interface assembly of the instrument of FIG. 37.
Figure 43:
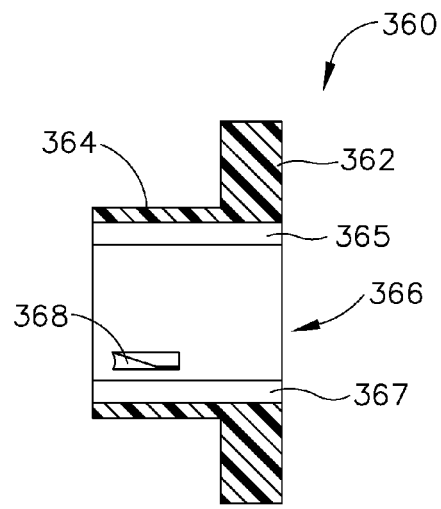
FIG. 43 depicts a cross sectional view of the second tubular member of FIG. 42 taken along the line 43-43 of FIG. 42.
Figure 44:
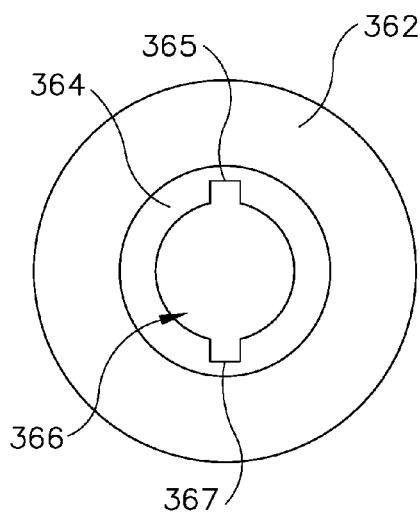
FIG. 44 depicts a front view of the second tubular member of FIG. 42.
Figure 45:
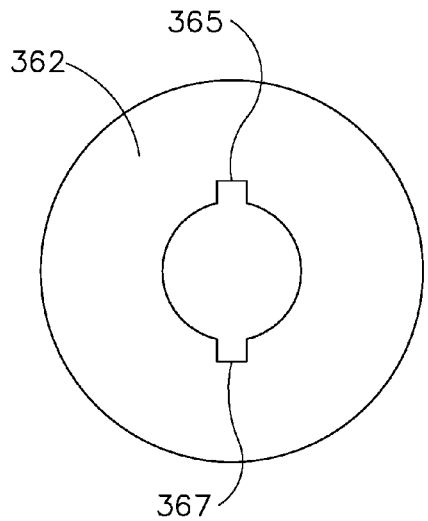
FIG. 45 depicts a rear view of the second tubular member of FIG. 42.

FIG. 39 shows that plug (393) comprises a first channel (395) extending longitudinally along one surface of plug (393) and a second channel (396) extending longitudinally along an opposite surface of plug (393). Plug (393) may be inserted within the proximal end inner shaft (330) to deflect and maintain coupling features (336, 338) outwardly. For example, articulation beams (337, 339) are resilient and are biased inwardly such that coupling features (336, 338) are housed within inner shaft (330), as shown in FIGS. 40A and 41A. Plug (393) is then inserted distally such that plug (393) engages ramped surfaces (324, 326) of translating members (333, 335). Plug (393) then cammingly slides between articulation beams (337, 339) such that articulation beam (337) is positioned within channel (395) of plug (393) and articulation beam (339) is positioned within channel (396) of plug (393), as shown in FIG. 41B. As plug (393) is inserted between articulation beams (337, 339), plug (393) drives articulation beams (337, 339) outwardly. This drives coupling features (336, 338) of translation members (333, 335) outwardly such that coupling features (336, 338) extend through respective channels (334) of inner shaft (330), as shown in FIG. 40B.

Interface assembly (310) is similar to interface assembly (210), except that second and third tubular members (360, 370) comprise an opening (368) instead of a slot (268, 278) to receive coupling features (336, 338). As shown in FIGS. 42-45, second tubular member (360) comprises a pair of recesses (365, 367) extending through opening (366) of second tubular member (360). This allows coupling features (322, 332) of outer shaft (320) and inner shaft (330) to pass through recesses (365, 367) as shaft assembly (302) is slid distally through second tubular member (360). Opening (366) also comprises a recess (368) extending within opening (366). Recess (368) is configured to receive coupling feature (336) of articulation beam (337) when coupling feature (336) is deflected outwardly. Third tubular member (370) is similar to second tubular member (360) and is configured to receive coupling feature (338) of articulation beam (339) when coupling feature (338) is deflected outwardly.

Figure 46A:
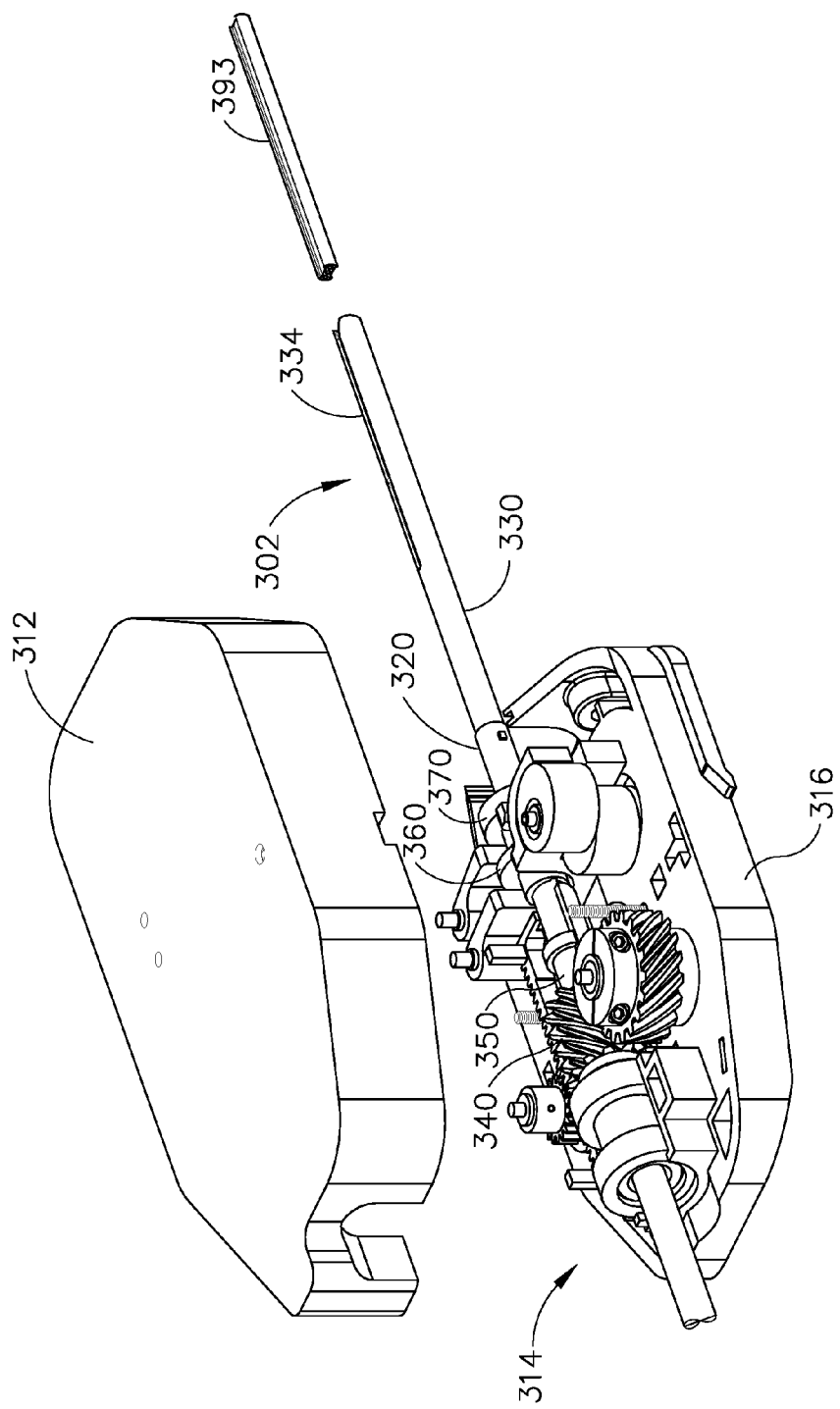
FIG. 46A depicts a partial perspective view of the instrument of FIG. 37, showing the shaft assembly being inserted within the interface assembly.

FIGS. 46A-46D show an exemplary assembly of shaft assembly (302) within interface assembly (310). As shown in FIG. 46A, shaft assembly (302) may be inserted distally through a proximal end of interface assembly (310). Coupling feature (322) of outer shaft (320) slides distally through recesses (365) of second and third tubular members (360, 370) and recess (253) of first tubular member (350) until coupling feature (322) enters slot (246) of helical gear (340). Coupling feature (322) then slides distally within recess (245) of slot (246) until coupling feature (322) aligns with transverse recess (247) of slot (246). Coupling feature (332) of inner shaft (330) slides distally through recesses (367) of second and third tubular members (360, 370) and until coupling feature (332) enters slot (258) of first tubular member (350). Coupling feature (332) then slides distally within recess (257) of slot (258) until coupling feature (332) aligns with transverse recess (259) of slot (258).

Figure 46C:
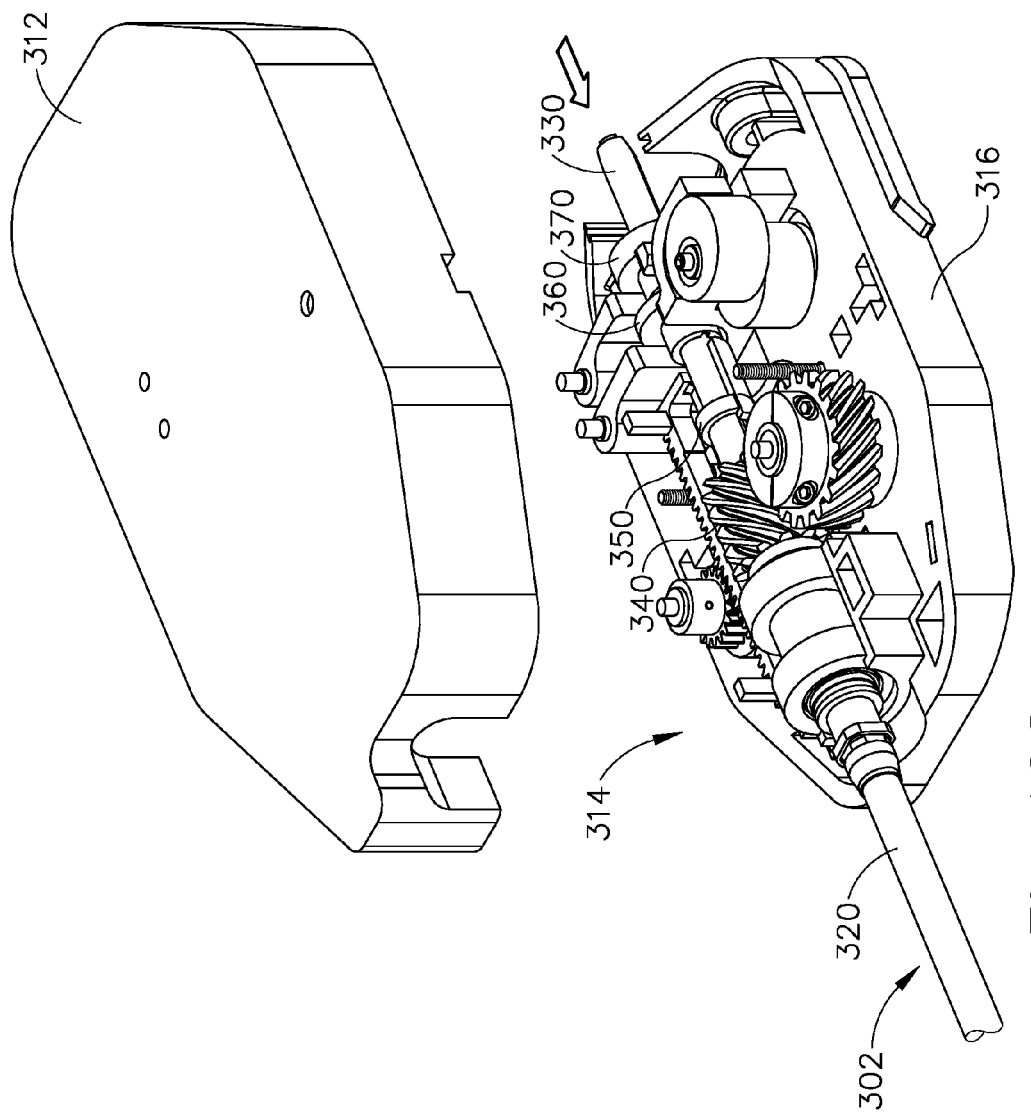
FIG. 46C depicts a partial perspective view of the instrument of FIG. 37, showing the plug coupled with the shaft assembly.
Figure 46D:
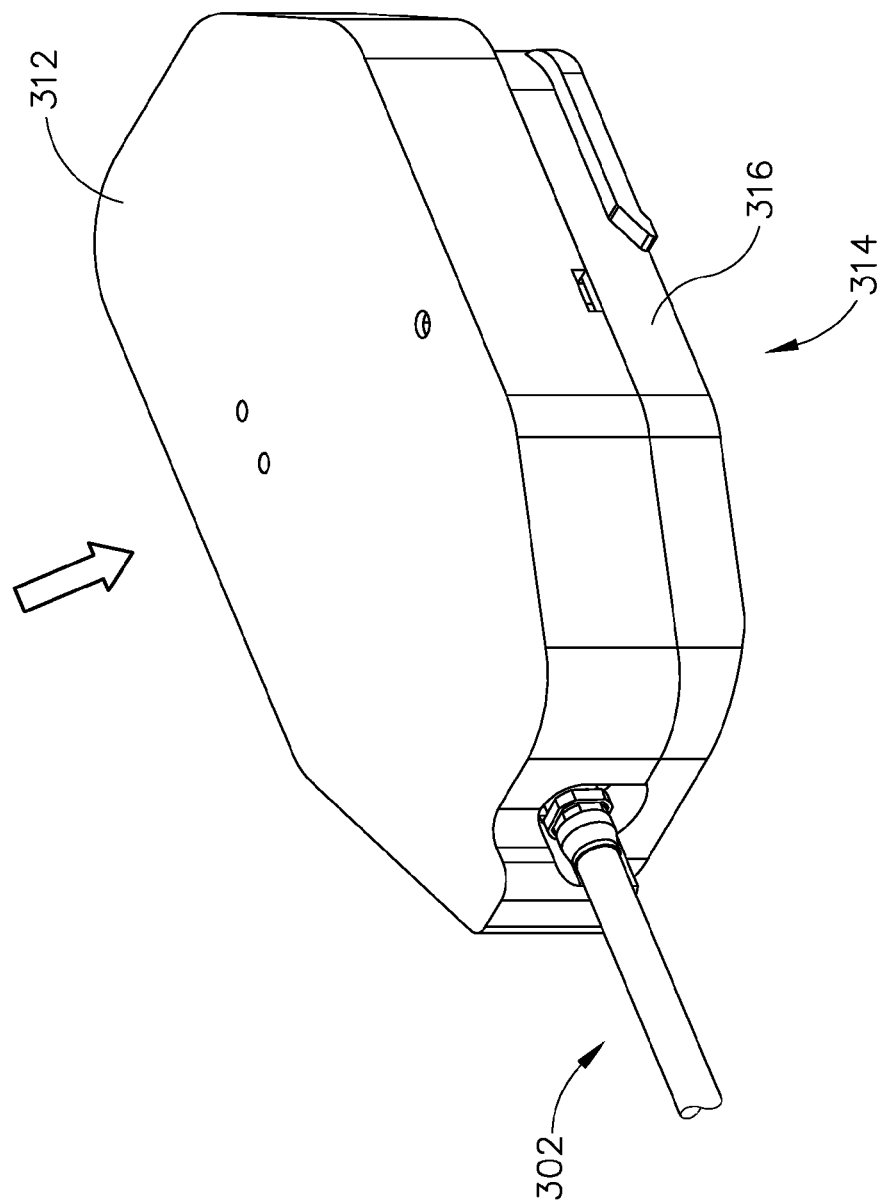
FIG. 46D depicts a partial perspective view of the instrument of FIG. 37, showing the cover coupled with the interface assembly.

Shaft assembly (302) is then rotated within interface assembly (310) to lock the longitudinal position of shaft assembly (302) relative to interface assembly (310), as shown in FIG. 46B. For example, coupling feature (322) rotates within transverse recess (247) of slot (246) and coupling feature (332) rotates within transverse recess (259) of slot (258). Plug (393) is then inserted within inner shaft (330) to deflect coupling features (336, 338) outwardly, as shown in FIG. 46C. Plug (393) is inserted between articulation beams (337, 339) to drive articulation beams (337, 339) and translating members (333, 335) outwardly. This extends coupling features (336, 338) through channel (334) of inner shaft (330). Accordingly, coupling feature (336) extends within recess (368) of second tubular member (360) and coupling feature (338) extends within recess (368) of third tubular member (370). Once shaft assembly (302) is coupled with interface assembly (310), housing (312) is coupled with base (314) of interface assembly (310), as shown in FIG. 46D, similar to interface assembly (210).

After housing (312) is coupled with base (314) of interface assembly (310), shaft assembly (302) may be operated by interface assembly (310). Drive shaft (349) may be rotated through drive features in dock (72) that are coupled with corresponding disc (285), to position end effector (206) at a desired angular orientation relative to the tissue. Drive shaft (386) may then be rotated through a drive feature in dock (72) that is coupled with corresponding disc (289), to pivot or flex articulation section (204) of shaft assembly (302) in order to position end effector (206) at a desired position and orientation relative to an anatomical structure within the patient. Two layers of tissue of the anatomical structure are then captured between jaws (182, 184) by rotating drive shaft (341) through a drive feature in dock (72) coupled with corresponding disc (283) to advance firing beam (190) distally through a first range of motion. As noted above, flanges (192, 196) cammingly act to pivot jaw (182) toward jaw (184) when firing beam (190) is actuated distally by rotating drive shaft (341).

With tissue layers captured between jaws (182, 184) firing beam (190) continues to advance distally in response to continued rotation of drive shaft (341). As firing beam (190) continues to advance distally, distal blade (194) simultaneously severs the clamped tissue layers, resulting in separated upper layer portions being apposed with respective separated lower layer portions. With severed tissue layer portions being compressed between jaws (182, 184), electrode surfaces (186, 187) are activated with bipolar RF energy by the surgeon providing a corresponding command input through controller (30) (e.g., through user input assembly (32) or footswitches (38), etc.). Bipolar RF energy delivered by power source (102) ultimately thermally welds the tissue layer portions on one side of firing beam (190) together and the tissue layer portions on the other side of firing beam (190) together. Drive shaft (341) may then be actuated in the opposing direction to retract firing beam (190) and open jaws (182, 184) of end effector (206). Articulation section (204) may be again aligned with shaft assembly (302) by actuating drive shaft (386) and end effector (206) may be removed from the patient.

Housing (312) and shaft assembly (302) may then be decoupled from base (314) of interface assembly (310). For example, housing (312) is pulled upwardly from base (314). Plug (393) is removed from inner shaft (330) to allow articulation beams (337, 339) to bias back inwardly. This decouples coupling features (336, 338) from second and third tubular members (360, 370). Shaft assembly (302) is then rotated such that coupling features (322, 332) rotate out of corresponding transverse recesses (247, 259) of slots (246, 258). Shaft assembly (302) is then pulled proximally out of interface assembly (310). Shaft assembly (302) may then be discarded, while interface assembly (310) may be sterilized and reused in another surgical procedure.

E. Exemplary Collar Shaft Assembly Coupling Features

Figure 47:
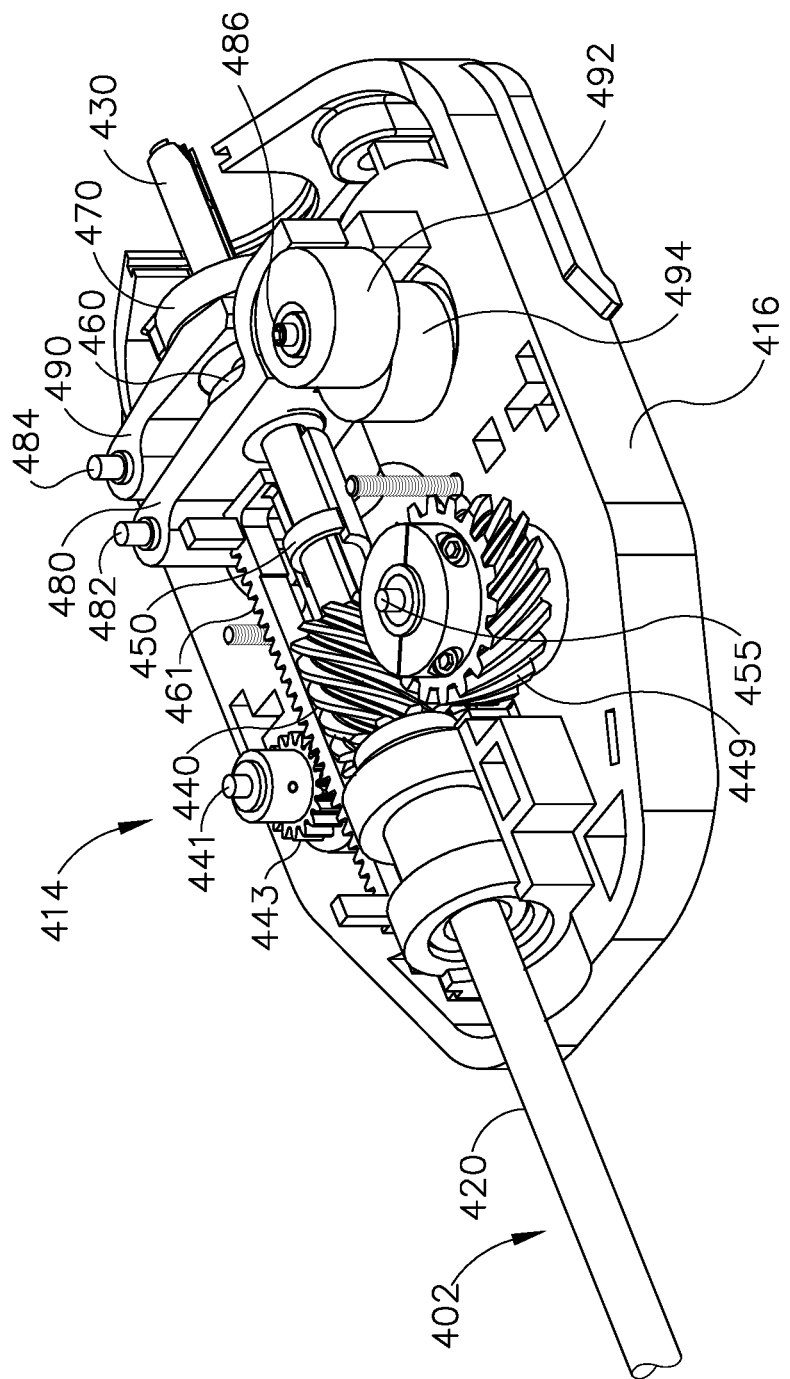
FIG. 47 depicts a partial perspective view of another exemplary surgical instrument suitable for incorporation with the system of FIG. 1, with a cover removed.
Figure 48:
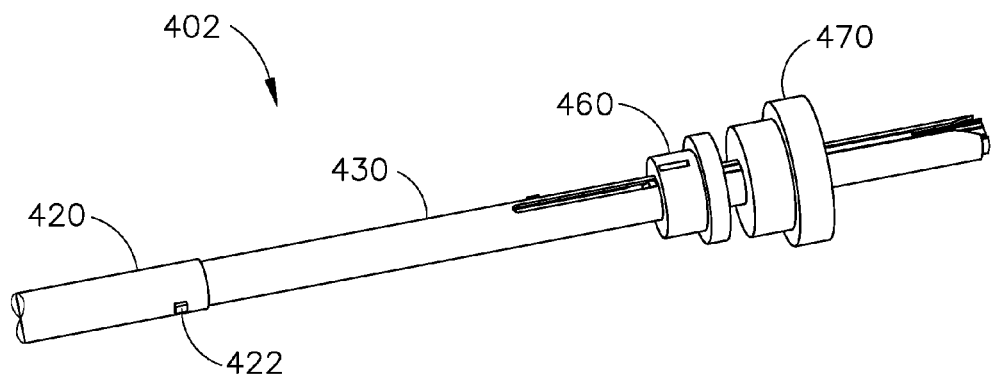
FIG. 48 depicts a partial perspective view of a proximal end of a shaft assembly of the instrument of FIG. 47.
Figure 49:
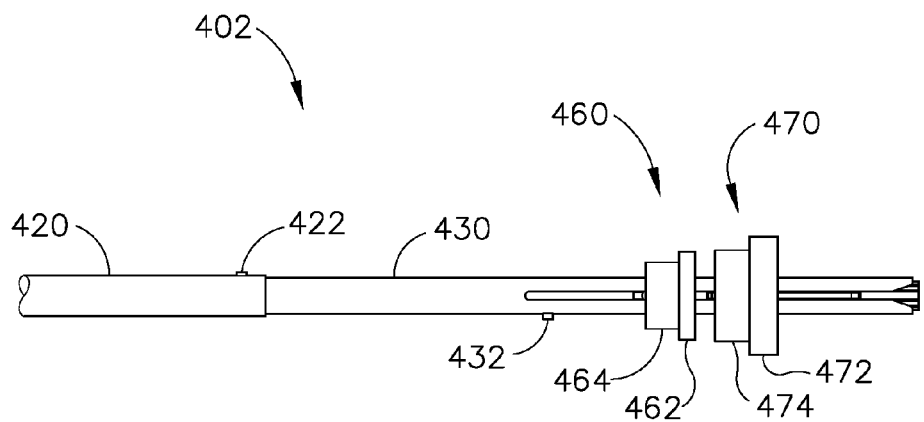
FIG. 49 depicts a side view of the shaft assembly of FIG. 48.

FIG. 47 shows another exemplary shaft assembly (402) and interface assembly (410). Shaft assembly (402) is similar to shaft assembly (202), except that shaft assembly (402) comprises collars (460, 470). Shaft assembly (402) comprises outer shaft (420) with a coupling feature (422) extending outwardly from outer shaft (420) and an inner shaft (430) that is slidably and coaxially disposed on outer shaft (420) and that extends proximally from outer shaft (420), as shown in FIGS. 48 and 49. Inner shaft (430) comprises a coupling feature (432) extending outwardly from inner shaft (430). A first collar (460) and a second collar (470) are slidably disposed along inner shaft (430) and are coupled with respective coupling features (236, 238). Accordingly, first and second collars (460, 470) are translatable along inner shaft (430) to translate respective coupling features (236, 238) relative to inner shaft (430). First collar (460) is proximal to coupling feature (432) and comprises a distal portion (464) and a proximal portion (462). Proximal portion (462) has a larger outer diameter than distal portion (464). Second collar (470) is proximal to first collar (460) and comprises a distal portion (474) and a proximal portion (472). Distal portion (474) has a similar and/or larger outer diameter than the proximal portion (462) of first collar (460). Proximal portion (472) of second collar (470) has a larger outer diameter than distal portion (474) of second collar (470).

Figure 50:
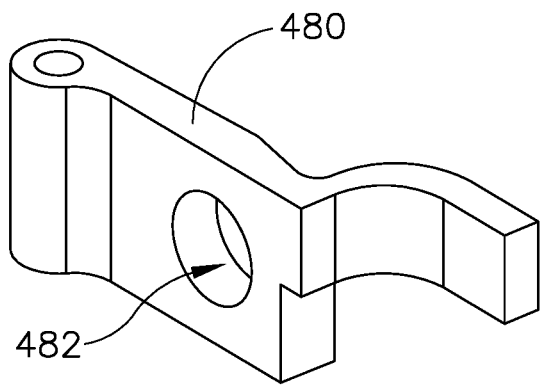
FIG. 50 depicts a perspective view of a first pivot arm of an interface assembly of the instrument of FIG. 47.
Figure 51:
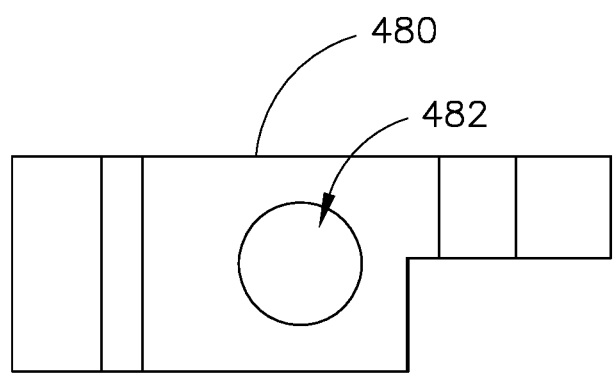
FIG. 51 depicts a front view of the first pivot arm of FIG. 50.
Figure 52:
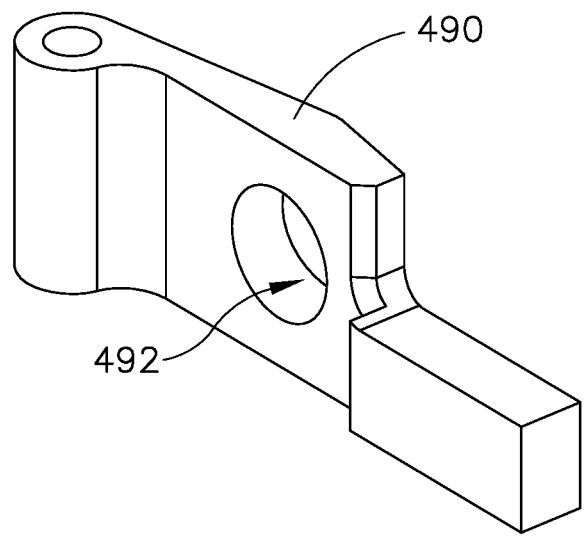
FIG. 52 depicts a perspective view of a second pivot arm of the interface assembly of the instrument of FIG. 47.
Figure 53:
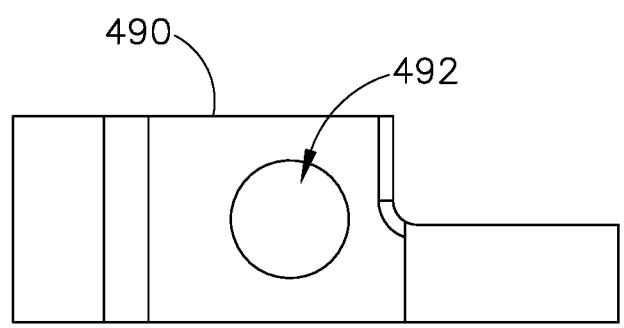
FIG. 53 depicts a front view of the second pivot arm of FIG. 52.

Interface assembly (410) is similar to interface assembly (210), except that interface assembly (410) does not include second or third tubular members (260, 270). Instead, collars (460, 470) of shaft assembly (402) engage first and second lever arms (480, 490) of interface assembly (410), as shown in FIG. 47. First lever arm (480) comprises an opening (482) to receive distal portion (464) of first collar (460), as shown in FIGS. 50-51. Distal portion (464) may be coupled within opening (482) to longitudinally secure first collar (460) relative to first lever arm (480) through a frictional fit, a bayonet fit, or other suitable methods that will be apparent to one with ordinary skill in the art in view of the teachings herein. Proximal portion (462) of first collar (460) may then engage the proximal wall of first lever arm (480) such that first collar (460) is unable to pass through first lever arm (480). Second lever arm (490) comprises an opening (492) to receive distal portion (474) of second collar (470), as shown in FIGS. 52-53. Distal portion (474) may be coupled within opening (492) to longitudinally secure second collar (470) relative to second lever arm (490) through a frictional fit, a bayonet fit, or other suitable methods that will be apparent to one with ordinary skill in the art in view of the teachings herein. Proximal portion (472) of second collar (470) may then engage the proximal wall of second lever arm (490) such that second collar (470) is unable to pass through second lever arm (490).

Figure 54A:
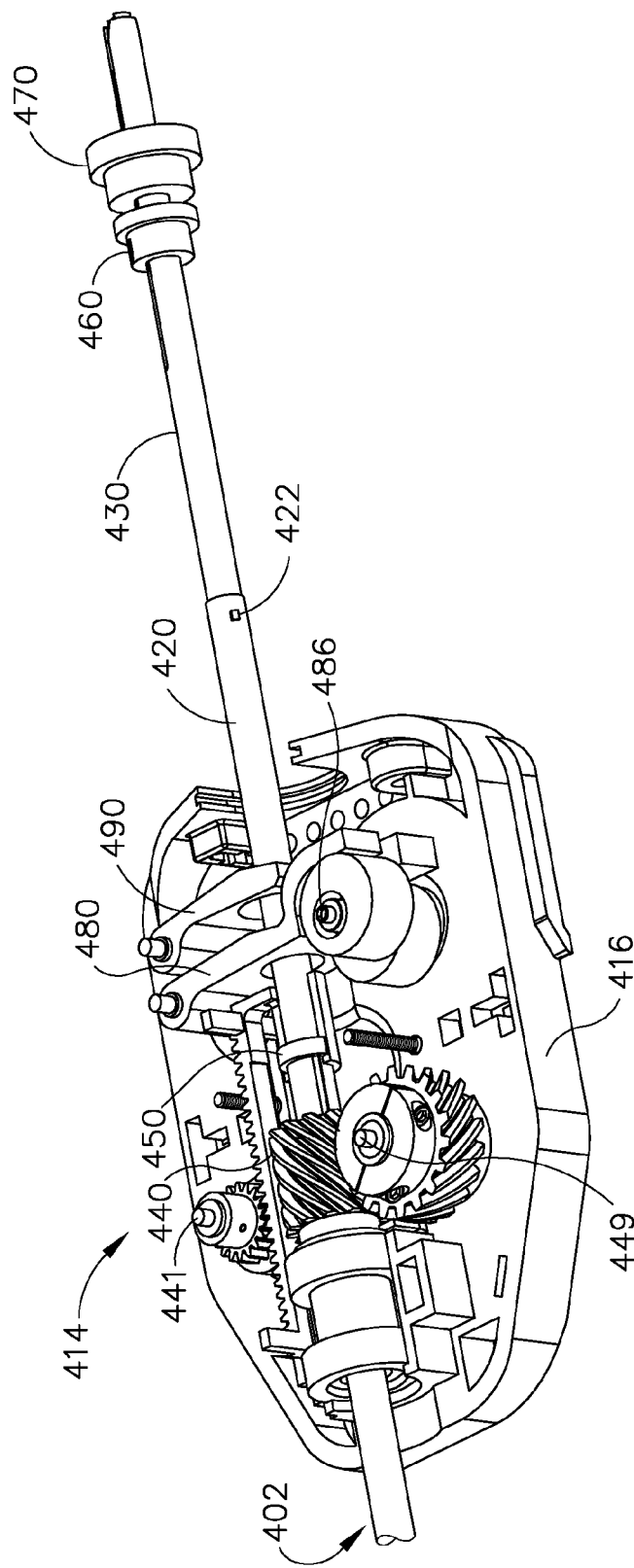
FIG. 54A depicts a partial perspective view of the instrument of FIG. 47, showing the shaft assembly being inserted within the interface assembly.
Figure 54B:
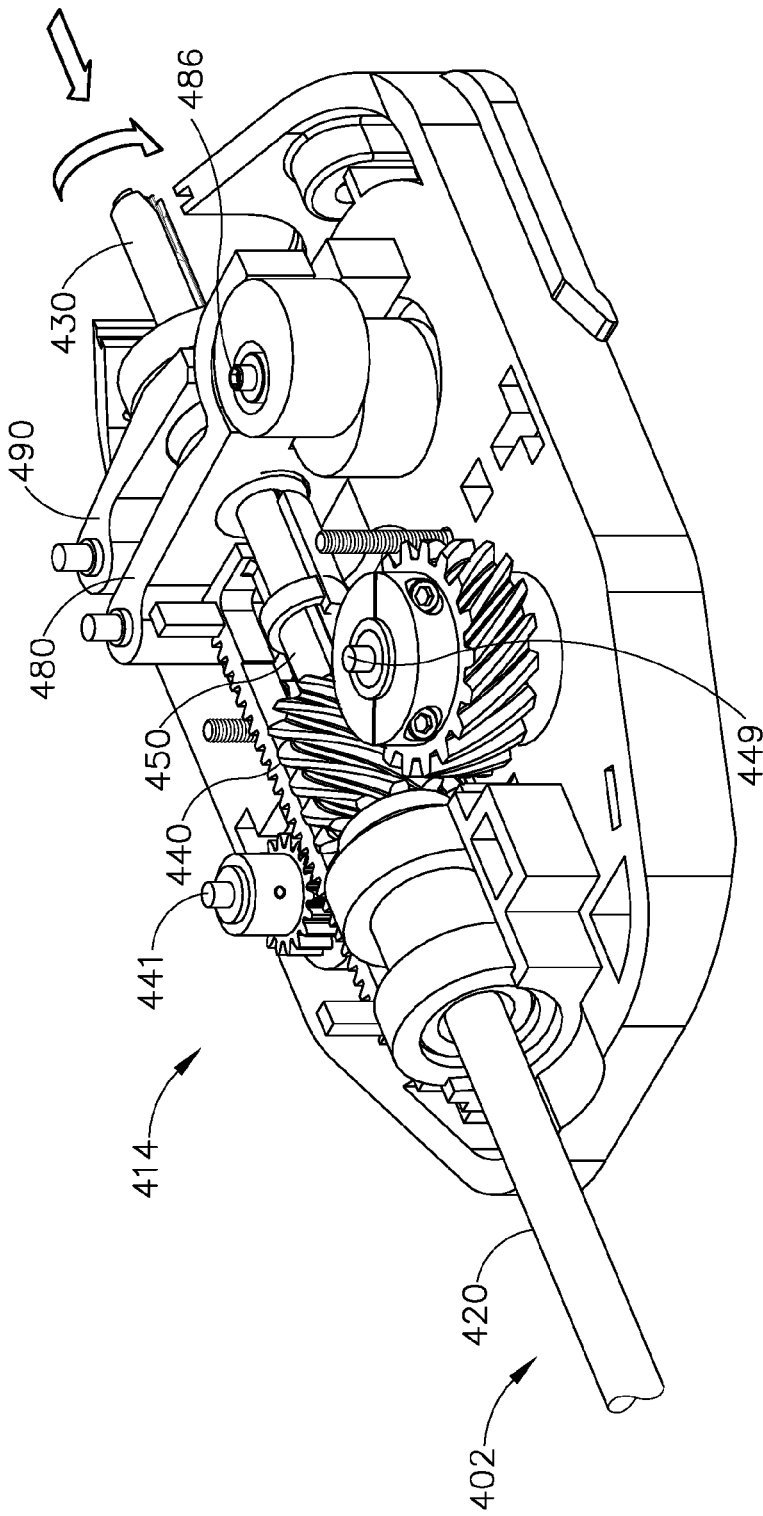
FIG. 54B depicts a partial perspective view of the instrument of FIG. 47, showing the shaft assembly coupled with the interface assembly.

FIGS. 54A-54B show an exemplary assembly of shaft assembly (402) within interface assembly (410). As shown in FIG. 54A, shaft assembly (402) may be inserted distally through a proximal end of interface assembly (410). Coupling feature (422) of outer shaft (420) slides distally through openings (482, 492) of lever arms (480, 490) and through recess (253) of first tubular member (450) until coupling feature (422) enters slot (246) of helical gear (440). Coupling feature (422) then slides distally within recess (245) of slot (246) until coupling feature (222) aligns with transverse recess (247) of slot (246). Coupling feature (432) of inner shaft (430) slides distally through openings (482, 492) of lever arms (480, 490) until coupling feature (432) enters slot (258) of first tubular member (450). Coupling feature (432) then slides distally within recess (257) of slot (258) until coupling feature (432) aligns with transverse recess (259) of slot (258). First collar (460) slides distally through opening (492) of second lever arm (490) until proximal portion (462) of first collar (460) engages the proximal wall of first lever arm (480). Second collar (470) slides distally until proximal portion (472) engages the proximal wall of second lever arm (490).

Shaft assembly (402) is then rotated within interface assembly (410) to lock the longitudinal position of shaft assembly (402) relative to interface assembly (410), as shown in FIG. 54B. For example, coupling feature (422) rotates within transverse recess (247) of slot (246) and coupling feature (432) rotates within transverse recess (259) of slot (258). Once shaft assembly (402) is coupled with interface assembly (410), a housing (not shown) may be coupled with base (414) of interface assembly (410) and shaft assembly (402) may be operated by interface assembly (410). Drive shaft (449) may be rotated through drive features in dock (72) that are coupled with corresponding disc (285), to position end effector (206) at a desired angular orientation relative to the tissue. Drive shaft (482) may then be rotated through a drive feature in dock (72) that is coupled with corresponding disc (289), to pivot or flex articulation section (204) of shaft assembly (402) in order to position end effector (206) at a desired position and orientation relative to an anatomical structure within the patient. Two layers of tissue of the anatomical structure are then captured between jaws (182, 184) by rotating drive shaft (441) through a drive feature in dock (72) coupled with corresponding disc (283) to advance firing beam (190) distally through a first range of motion. As noted above, flanges (192, 196) cammingly act to pivot jaw (182) toward jaw (184) when firing beam (190) is actuated distally by rotating drive shaft (441).

With tissue layers captured between jaws (182, 184) firing beam (190) continues to advance distally in response to continued rotation of drive shaft (341). As firing beam (190) continues to advance distally, distal blade (194) simultaneously severs the clamped tissue layers, resulting in separated upper layer portions being apposed with respective separated lower layer portions. With severed tissue layer portions being compressed between jaws (182, 184), electrode surfaces (186, 187) are activated with bipolar RF energy by the surgeon providing a corresponding command input through controller (30) (e.g., through user input assembly (32) or footswitches (38), etc.). Bipolar RF energy delivered by power source (102) ultimately thermally welds the tissue layer portions on one side of firing beam (190) together and the tissue layer portions on the other side of firing beam (190) together. Drive shaft (441) may then be actuated in the opposing direction to retract firing beam (190) and open jaws (182, 184) of end effector (206). Articulation section (204) may be again aligned with shaft assembly (402) by actuating drive shaft (486) and end effector (206) may be removed from the patient.

Shaft assembly (402) may then be decoupled from base (414) of interface assembly (410). For example, shaft assembly (402) is rotated such that coupling features (422, 432) rotate out of corresponding transverse recesses (247, 259) of slots (246, 258). Shaft assembly (402) is then pulled proximally out of interface assembly (410). Shaft assembly (402) may then be discarded, while interface assembly (410) may be sterilized and reused in another surgical procedure.

F. Exemplary Interface Assembly with a Removable Rack

Figure 55:
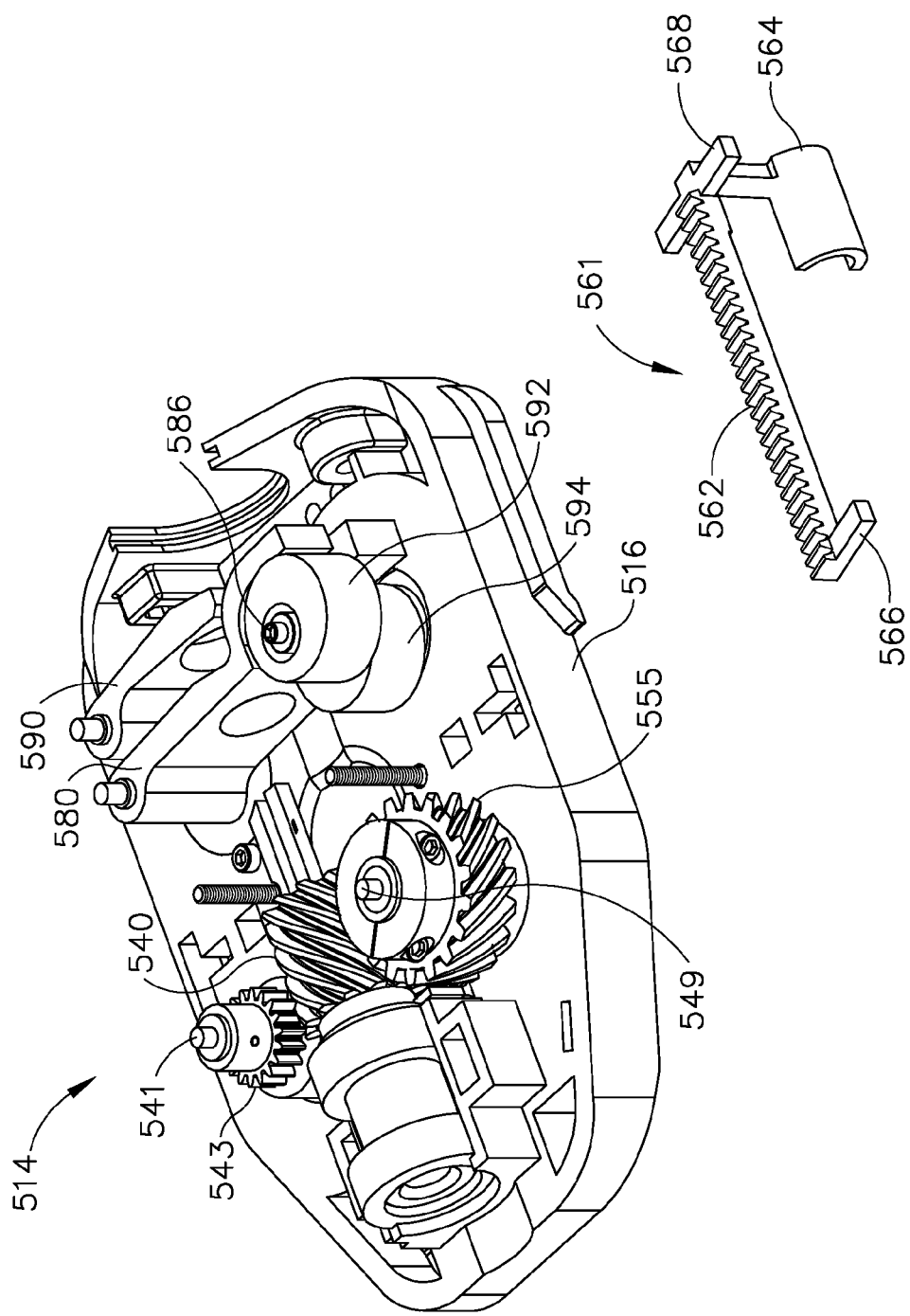
FIG. 55 depicts a partial perspective view of an exemplary interface assembly for use with the system of FIG. 1.

FIG. 55 shows another exemplary interface assembly (510) that is configured to receive a shaft assembly (502). Interface assembly (510) is similar to interface assembly (410), except that interface assembly (510) comprises a removable rack (561). Rack (561) is similar to rack (261), except that rack (561) comprises a top cover (564) extending from protrusion (568) of rack (561) instead of a bracket (296). Rack (561) is configured to be inserted within interface assembly (510) after shaft assembly (502) is coupled with interface assembly (510). Teeth (562) of rack (561) engage the teeth of gear (543) such that rack (561) translates as gear (543) is rotated by drive shaft (541). Top cover (564) of rack (561) engages first tubular member (550) with a snap fit to translate first tubular (550) with rack (561). Shaft assembly (502) is similar to shaft assembly (402).

Figure 56A:
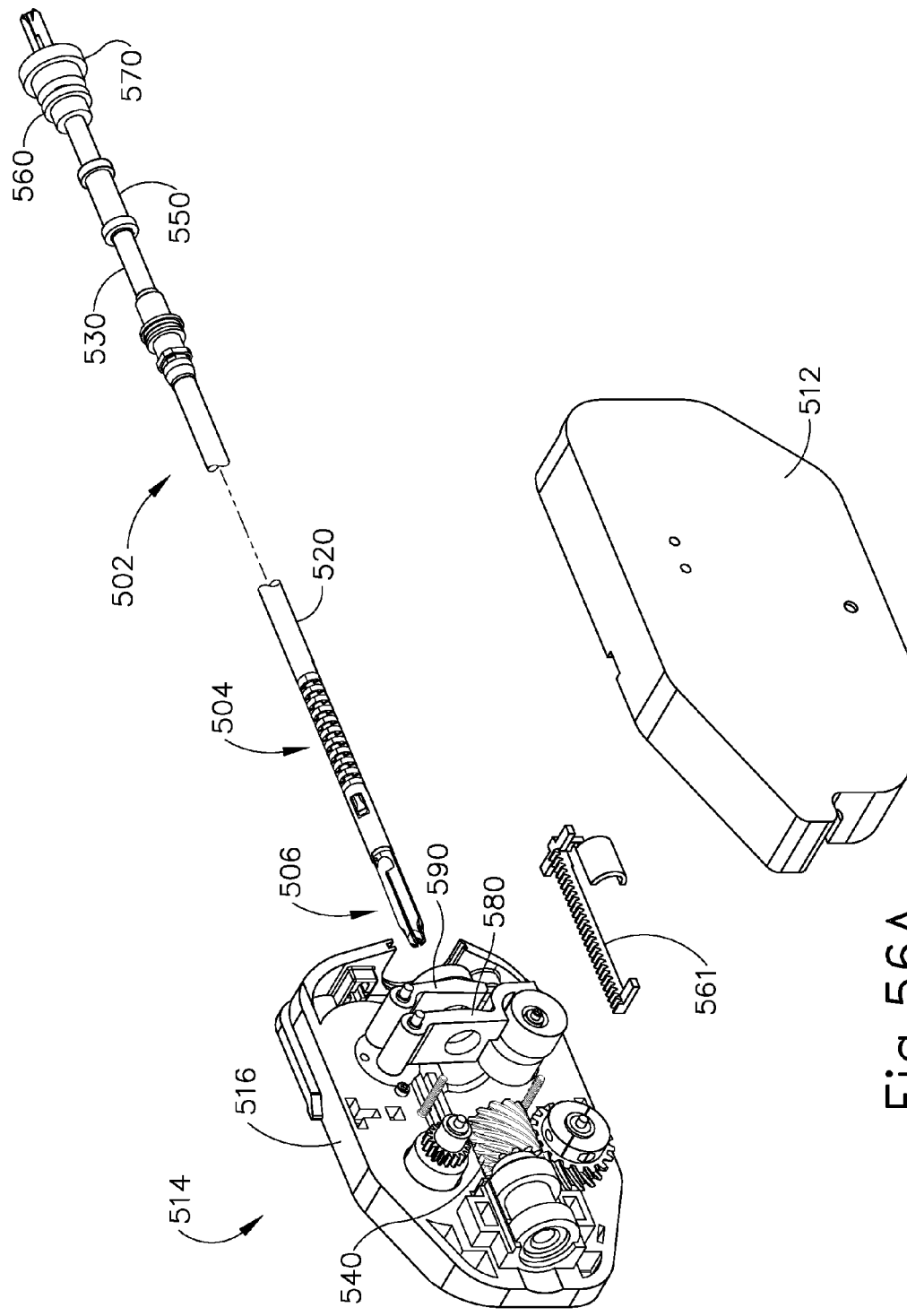
FIG. 56A depicts a partial perspective view of an exemplary instrument for use with the system of FIG. 1, showing a shaft assembly being inserted within the interface assembly of FIG. 55.

FIGS. 56A-56D show an exemplary assembly of shaft assembly (502) within interface assembly (510). As shown in FIG. 56A, shaft assembly (502) may be inserted distally through a proximal end of interface assembly (510). Coupling feature (422) of outer shaft (520) slides distally through openings (482, 492) of lever arms (580, 590) and recess (253) of first tubular member (550) until coupling feature (422) enters slot (246) of helical gear (540). Coupling feature (422) then slides distally within recess (245) of slot (246) until coupling feature (422) aligns with transverse recess (247) of slot (246). Coupling feature (432) of inner shaft (530) slides distally through openings (482, 492) of lever arms (580, 590) until coupling feature (432) enters slot (258) of first tubular member (550). Coupling feature (432) then slides distally within recess (257) of slot (258) until coupling feature (432) aligns with transverse recess (259) of slot (258). First collar (560) slides distally through opening (492) of second lever arm (590) until proximal portion (462) of first collar (560) engages the proximal wall of first lever arm (580). Second collar (570) slides distally until proximal portion (472) engages the proximal wall of second lever arm (590).

Figure 56B:
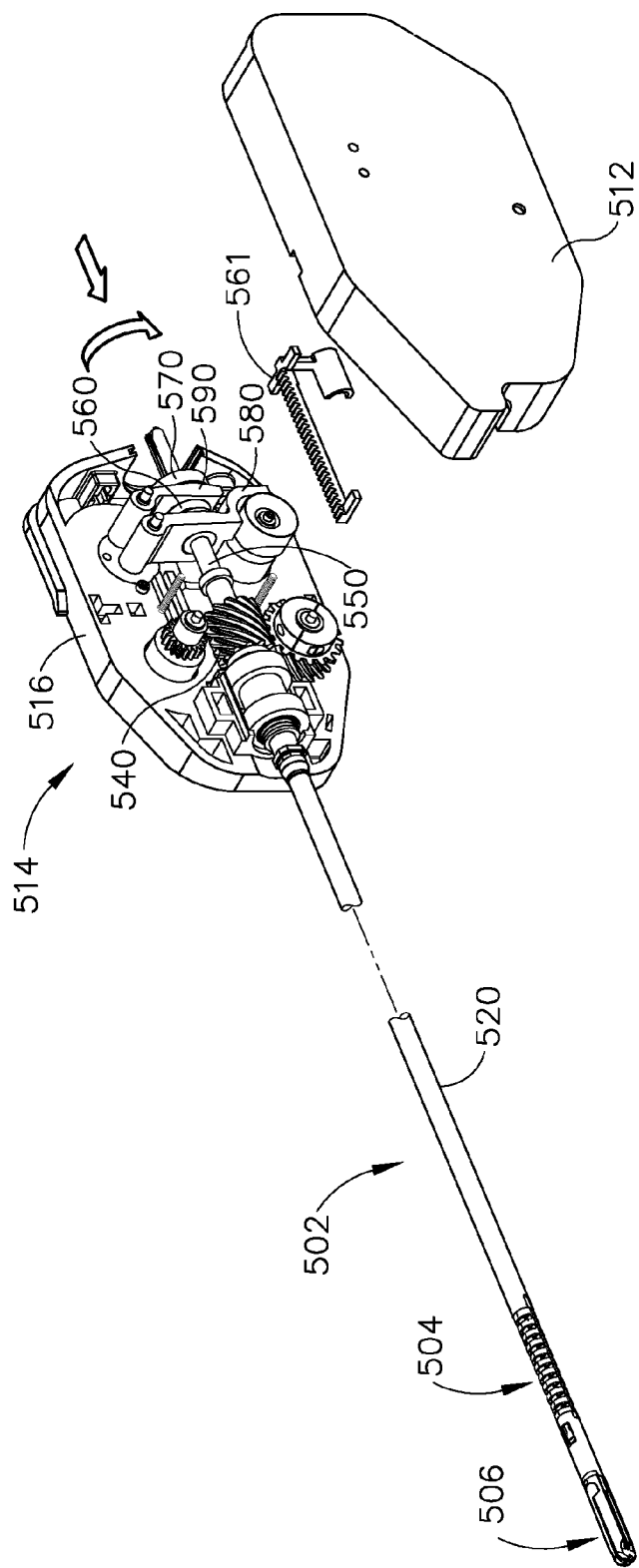
FIG. 56B depicts a partial perspective view of the instrument of FIG. 56A, showing the shaft assembly coupled with the interface assembly.
Figure 56C:
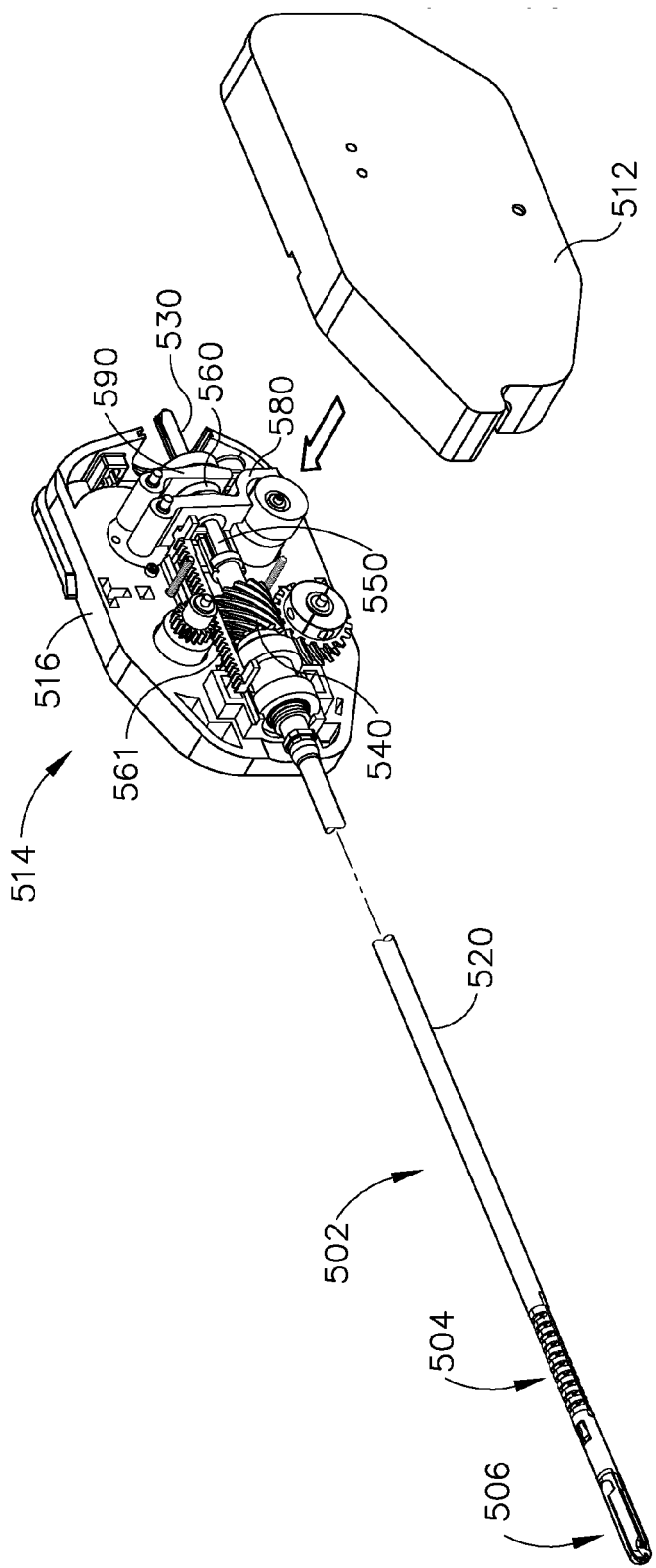
FIG. 56C depicts a partial perspective view of the instrument of FIG. 56A, showing a rack assembly coupled with the interface assembly.
Figure 56D:
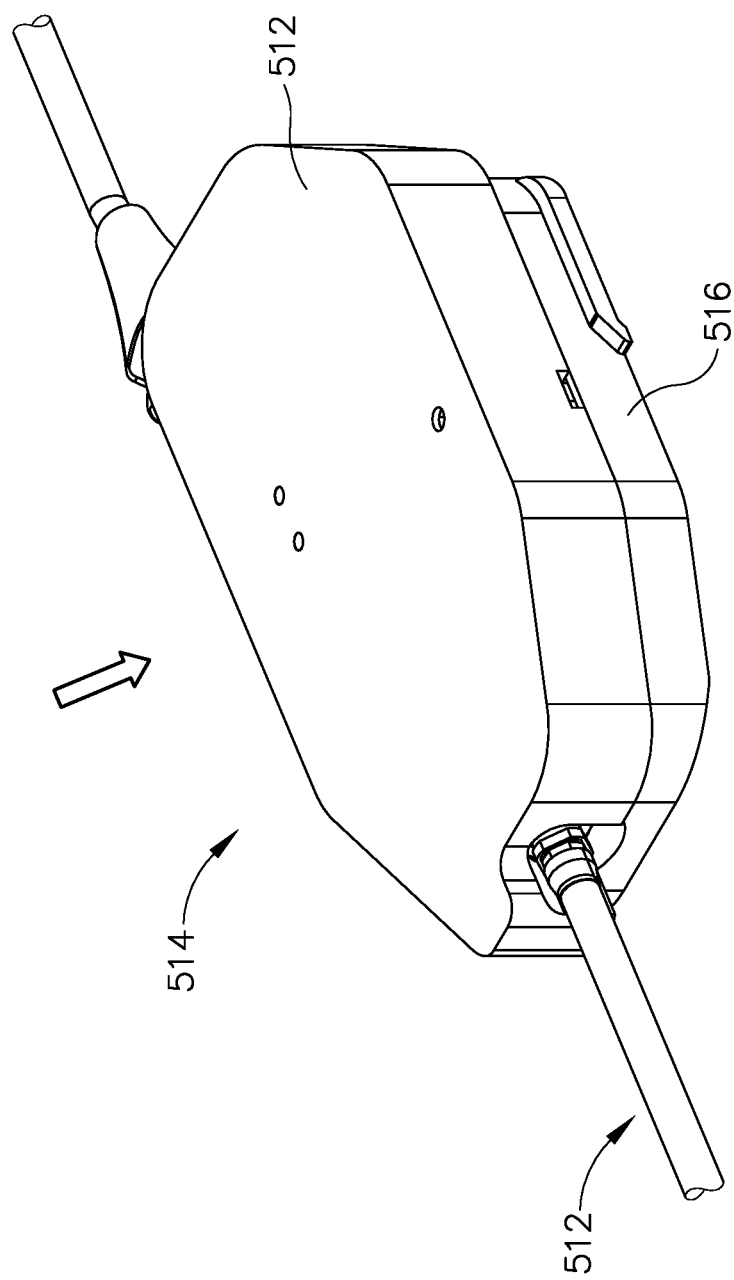
FIG. 56D depicts a partial perspective view of the instrument of FIG. 56A, showing a cover coupled with the interface assembly.

Shaft assembly (502) is then rotated within interface assembly (510) to lock the longitudinal position of shaft assembly (502) relative to interface assembly (510), as shown in FIG. 56B. For example, coupling feature (422) rotates within transverse recess (247) of slot (246) and coupling feature (432) rotates within transverse recess (259) of slot (258). Rack (561) is then inserted within interface assembly (510) along a path that is transverse to the longitudinal axis of shaft assembly (502) to engage gear (543) and first tubular member (550), as shown in FIG. 56C. Once rack (561) is coupled with interface assembly (510), housing (512) is coupled with base (514) of interface assembly (510), as shown in FIG. 56D, similar to interface assembly (210).

After housing (512) is coupled with base (514) of interface assembly (510), shaft assembly (502) may be operated by interface assembly (510). Drive shaft (549) may be rotated through drive features in dock (72) that are coupled with corresponding disc (285), to position end effector (506) at a desired angular orientation relative to the tissue. Drive shaft (586) may then be rotated through a drive feature in dock (72) that is coupled with corresponding disc (289), to pivot or flex articulation section (504) of shaft assembly (502) in order to position end effector (506) at a desired position and orientation relative to an anatomical structure within the patient. Two layers of tissue of the anatomical structure are then captured between jaws (182, 184) by rotating drive shaft (541) through a drive feature in dock (72) that is coupled with corresponding disc (283) to advance firing beam (190) distally through a first range of motion. As noted above, flanges (192, 196) cammingly act to pivot jaw (182) toward jaw (184) when firing beam (190) is actuated distally by rotating drive shaft (541).

With tissue layers captured between jaws (182, 184) firing beam (190) continues to advance distally in response to continued rotation of drive shaft (541). As firing beam (190) continues to advance distally, distal blade (194) simultaneously severs the clamped tissue layers, resulting in separated upper layer portions being apposed with respective separated lower layer portions. With severed tissue layer portions being compressed between jaws (182, 184), electrode surfaces (186, 187) are activated with bipolar RF energy by the surgeon providing a corresponding command input through controller (30) (e.g., through user input assembly (32) or footswitches (38), etc.). Bipolar RF energy delivered by power source (102) ultimately thermally welds the tissue layer portions on one side of firing beam (190) together and the tissue layer portions on the other side of firing beam (190) together. Drive shaft (541) may then be actuated in the opposing direction to retract firing beam (190) and open jaws (182, 184) of end effector (506). Articulation section (504) may be again aligned with shaft assembly (502) by actuating drive shaft (586) and end effector (506) may be removed from the patient.

Housing (512) and shaft assembly (502) may then be decoupled from base (514) of interface assembly (510). For example, housing (512) is pulled upwardly from base (514). Rack (561) is removed interface assembly (510) by pulling rack (561) upwardly from base (514). Shaft assembly (502) is then rotated such that coupling features (422, 432) rotate out of corresponding transverse recesses (247, 259) of slots (246, 258). Shaft assembly (502) is then pulled proximally out of interface assembly (510). Shaft assembly (502) may then be discarded, while interface assembly (510) may be sterilized and reused in another surgical procedure.

IV. Miscellaneous

While examples herein include insertion of a shaft assembly into an interface assembly along a longitudinal axis of the shaft assembly from a proximal side of the interface assembly, it should be understood that some axial insertion techniques may include inserting the shaft assembly from the distal side of the interface assembly instead of approaching from the proximal side. It should also be understood that an interface assembly may include an integral power source such as a battery, and that such a battery may provide at least some of any electrical power required to operate the surgical instrument of the interface assembly. In other words, an interface assembly may provide electrical power to one or more components of the associated surgical instrument from a source that is internal to the interface assembly and/or from a source that is external to the interface assembly (e.g., through system (10)). Regardless of where the source is located, the interface assembly may include one or more conductive clips, contacts, and/or other features that provide automatic electrical coupling with the shaft assembly when the shaft assembly is mechanically coupled with the interface assembly. Various suitable ways in which a shaft assembly and an interface assembly may be electrically coupled will be apparent to those of ordinary skill in the art in view of the teachings herein.

Furthermore, an interface assembly may be configured to couple with a variety of types of modular shaft assemblies. Such modular shaft assemblies may provide inter-modality and/or intra-modality variation. Examples of inter-modality variation may include a single interface assembly being able to selectively couple with different shaft assemblies having a variety of end effectors that include staplers, RF electrosurgical features, ultrasonic cutting features, etc. Examples of intra-modality variation may include a single interface assembly being able to selectively couple with different RF electrosurgical shaft assemblies having a variety of end effectors that include straight jaws, curved jaws, etc. Other inter-modality variations and intra-modality variations will be apparent to those of ordinary skill in the art in view of the teachings herein.

It should be understood that any of the versions of instruments described herein may include various other features in addition to or in lieu of those described above. By way of example only, any of the instruments described herein may also include one or more of the various features disclosed in any of the various references that are incorporated by reference herein.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc.

In versions where the teachings herein are applied to a surgical stapling instrument, it should be understood that the teachings herein may be combined with the teachings of one or more of the following, the disclosures of all of which are incorporated by reference herein: U.S. Pat. No. 7,380,696; U.S. Pat. No. 7,404,508; U.S. Pat. No. 7,455,208; U.S. Pat. No. 7,506,790; U.S. Pat. No. 7,549,564; U.S. Pat. No. 7,559,450; U.S. Pat. No. 7,654,431; U.S. Pat. No. 7,780,054; U.S. Pat. No. 7,784,662; and/or U.S. Pat. No. 7,798,386. Other suitable ways in which the teachings herein may be applied to a surgical stapling instrument will be apparent to those of ordinary skill in the art in view of the teachings herein.

In versions where the teachings herein are applied to an ultrasonic surgical instrument, it should be understood that some such instruments may lack a translating firing beam. The components described herein for translating a firing beam may instead simply translate a jaw closing member. Alternatively, such translating features may simply be omitted. In any case, it should be understood that the teachings herein may be combined with the teachings of one or more of the following: U.S. Pat. Pub. No. 2006/0079874, entitled "Tissue Pad for Use with an Ultrasonic Surgical Instrument," published Apr. 13, 2006, now abandoned, the disclosure of which is incorporated by reference herein; U.S. Pat. Pub. No. 2007/0191713, entitled "Ultrasonic Device for Cutting and Coagulating," published Aug. 16, 2007, now abandoned, the disclosure of which is incorporated by reference herein; U.S. Pat. Pub. No. 2007/0282333, entitled "Ultrasonic Waveguide and Blade," published Dec. 6, 2007, now abandoned, the disclosure of which is incorporated by reference herein; U.S. Pat. Pub. No. 2008/0200940, entitled "Ultrasonic Device for Cutting and Coagulating," published Aug. 21, 2008, now abandoned, the disclosure of which is incorporated by reference herein; U.S. Pat. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; U.S. Pat. No. 6,500,176, entitled "Electrosurgical Systems and Techniques for Sealing Tissue," issued Dec. 31, 2002, the disclosure of which is incorporated by reference herein; U.S. Pat. Pub. No. 2011/0087218, entitled "Surgical Instrument Comprising First and Second Drive Systems Actuatable by a Common Trigger Mechanism," published Apr. 14, 2011, issued as U.S. Pat. No. 8,939,974 on Jan. 27, 2015, the disclosure of which is incorporated by reference herein; and/or U.S. Pat. No. 6,783,524, entitled "Robotic Surgical Tool with Ultrasound Cauterizing and Cutting Instrument," issued Aug. 31, 2004, the disclosure of which is incorporated by reference herein. Other suitable ways in which the teachings herein may be applied to an ultrasonic surgical instrument will be apparent to those of ordinary skill in the art in view of the teachings herein.

It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for operating on tissue, comprising:
   (a) an end effector;
   (b) a shaft assembly extending proximally from the end effector along a longitudinal axis, wherein the shaft assembly includes a proximal end portion having a first coupling feature projecting radially outward therefrom about the longitudinal axis; and
   (c) an interface assembly configured to removably couple with the shaft assembly for use with a robotic system, the interface assembly including:
      (i) a proximal end,
      (ii) a distal end, and
      (iii) a first drive assembly having a first slot with a first proximal slot opening, wherein the first slot is configured to distally receive the first coupling feature of the shaft assembly through the first proximal slot opening to removably couple the first coupling feature to the first drive assembly, wherein the first drive assembly is configured to actuate the first coupling feature to thereby actuate the end effector,
   wherein the shaft assembly is axially insertable into the proximal end of the interface assembly upon removably coupling the first coupling feature to the first drive assembly such that the end effector is configured to travel through the proximal end of the interface assembly and out through the distal end of the interface assembly,
   wherein the first drive assembly further includes a first drive opening extending longitudinally therethrough, wherein the first drive opening is configured to distally receive the end effector and the shaft assembly such that the end effector is configured to travel through the first drive opening, and
   wherein the first slot is positioned about the first drive opening such that the first slot extends radially inward in communication with the first drive opening to receive the radially outward projecting first coupling feature,
   wherein the first slot is configured to receive the first coupling feature as a first bayonet fitting.

2. The apparatus of claim 1, wherein the first drive opening has a proximal diameter and a distal diameter, and wherein the proximal diameter is larger than the distal diameter.

3. The apparatus of claim 1, wherein the first drive assembly comprises a helical gear, wherein the helical gear is concentrically positioned about the first drive opening.

4. The apparatus of claim 3, wherein the helical gear is configured to rotate the shaft assembly relative to the interface assembly.

5. The apparatus of claim 1, wherein the proximal portion of the shaft assembly further includes a second coupling feature projecting radially therefrom about the longitudinal axis, wherein the second coupling feature is configured to move relative to the first coupling feature, wherein the interface assembly further includes a second drive assembly having a second slot with a second proximal slot opening, wherein the second slot is configured to distally receive the second coupling feature of the shaft assembly through the second proximal slot opening to removably couple the second coupling feature to the second drive assembly, wherein the second drive assembly is configured to actuate the second coupling feature to thereby further actuate the end effector.

6. The apparatus of claim 5, wherein the second drive assembly further includes a second drive opening extending longitudinally therethrough, wherein the second drive opening is configured to distally receive the end effector and the shaft assembly such that the end effector is configured to travel through the second drive opening.

7. The apparatus of claim 6, wherein the first drive opening and the second drive opening are coaxial to coaxially receive the shaft assembly along the longitudinal axis.

8. The apparatus of claim 6, wherein the second slot is positioned about the second drive opening such that the second slot extends radially inward in communication with the second drive opening.

9. The apparatus of claim 6, wherein the second drive assembly further includes a through slot extending longitudinally therethrough from a proximal through opening to a distal through opening, wherein the through slot is configured to receive the first coupling feature such that the first coupling feature passes through the through slot and the distal through opening to the first drive assembly for removably coupling the first coupling feature to the first drive assembly.

10. The apparatus of claim 9, wherein the second slot and the through slot are positioned about the second drive opening.

11. The apparatus of claim 10, wherein the second drive assembly comprises a tubular member, wherein the tubular member is concentrically positioned about the second drive opening.

12. The apparatus of claim 11, the second slot is configured to receive the second coupling feature as a second bayonet fitting.

13. The apparatus of claim 5, wherein the shaft assembly further includes an outer shaft and an inner shaft extending proximally from the outer shaft, wherein the inner shaft is translatable relative to the outer shaft, wherein the first coupling feature is positioned on the outer shaft, wherein the second coupling feature is positioned on the inner shaft proximal to the first coupling feature.

14. The apparatus of claim 13, wherein the end effector further includes a first jaw and a second jaw pivotable relative to the first jaw, wherein the tubular member is configured to move the second jaw relative to the first jaw.

15. The apparatus of claim 13, wherein the proximal portion of the shaft assembly further includes a third coupling feature and a fourth coupling feature projecting radially therefrom about the longitudinal axis, wherein the interface assembly further includes a third drive assembly and a fourth drive assembly, wherein the third and fourth drive assemblies are configured to removably couple with the third and fourth coupling features, respectively, such that the third and fourth drive assemblies are configured to respectively actuate the third and fourth coupling features to thereby further actuate the end effector.

16. An apparatus for operating on tissue, comprising:
(a) an end effector;
(b) a shaft assembly extending proximally from the end effector along a longitudinal axis, wherein the shaft assembly includes a proximal end portion having a first coupling feature projecting radially outward therefrom about the longitudinal axis and a second coupling feature projecting radially outward therefrom about the longitudinally axis, wherein the shaft assembly further includes an outer member and an inner member, wherein the outer member is configured to movably receive the inner member and wherein the first and second coupling features extend from the outer and inner members, respectively, and wherein the second coupling feature is configured to move relative to the first coupling feature to thereby actuate the inner member relative to the outer member; and
(c) an interface assembly configured to removably couple with the shaft assembly for use with a robotic system, the interface assembly including:
(i) a proximal end,
(ii) a distal end,
(iii) a first drive assembly having a first slot with a first proximal slot opening, wherein the first slot is configured to distally receive the first coupling feature of the shaft assembly through the first proximal slot opening to removably couple the first coupling feature to the first drive assembly, wherein the first drive assembly is configured to actuate the first coupling feature to thereby actuate the end effector, and
(iv) a second drive assembly having a second slot with a second proximal slot opening, wherein the second slot is configured to distally receive the second coupling feature of the shaft assembly through the second proximal slot opening to removably couple the second coupling feature to the second drive assembly, wherein the second drive assembly is configured to actuate the second coupling feature to thereby further actuate the end effector,
wherein the shaft assembly is axially insertable into the proximal end of the interface assembly upon removably coupling the first coupling feature to the first drive assembly such that the end effector is configured to travel through the proximal end of the interface assembly and out through the distal end of the interface assembly.

17. The apparatus of claim 16, wherein the second coupling feature is positioned proximal relative to the first coupling feature.

18. An apparatus for operating on tissue, comprising:
(a) an end effector;
(b) a shaft assembly extending proximally from the end effector along a longitudinal axis, wherein the shaft assembly includes a proximal end portion having a first coupling feature projecting radially therefrom about the longitudinal axis; and
(c) an interface assembly configured to removably couple with the shaft assembly for use with a robotic system, the interface assembly including:
(i) a proximal end,
(ii) a distal end, and
(iii) a first drive assembly having a first slot with a first proximal slot opening, wherein the first slot is configured to distally receive the first coupling feature of the shaft assembly through the first proximal slot opening to removably couple the first coupling feature to the first drive assembly, wherein the first drive assembly is configured to actuate the first coupling feature to thereby actuate the end effector,
wherein the shaft assembly is axially insertable into the proximal end of the interface assembly upon removably coupling the first coupling feature to the first drive assembly such that the end effector is configured to travel through the proximal end of the interface assembly and out through the distal end of the interface assembly, wherein the shaft assembly further includes an outer shaft and an inner shaft extending proximally from the outer shaft, wherein the inner shaft is movable relative to the outer shaft, and wherein the first coupling feature extends from the outer shaft or inner shaft and is configured to actuate the outer and inner shafts relative to each other.

19. The apparatus of claim 18, wherein the first coupling feature extends from the outer shaft.

\* \* \* \* \*